(12) United States Patent
Boudreau et al.

(10) Patent No.: US 7,157,439 B2
(45) Date of Patent: Jan. 2, 2007

(54) HOXD3, HOXA3, AND HOXB3 COMPOSITIONS AND METHODS FOR IMPROVED WOUND HEALING

(75) Inventors: Nancy Boudreau, San Francisco, CA (US); David M. Young, Larkspur, CA (US); Cornelia Myers, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 443 days.

(21) Appl. No.: 10/746,592

(22) Filed: Dec. 23, 2003

(65) Prior Publication Data

US 2004/0228920 A1    Nov. 18, 2004

Related U.S. Application Data

(63) Continuation-in-part of application No. 10/305,667, filed on Nov. 26, 2002, which is a continuation-in-part of application No. PCT/US02/19020, filed on Jun. 14, 2002.

(60) Provisional application No. 60/307,632, filed on Jul. 24, 2001, provisional application No. 60/298,688, filed on Jun. 14, 2001.

(51) Int. Cl.
  *A61K 31/70*   (2006.01)
  *A61K 9/127*   (2006.01)
  *A61K 39/21*   (2006.01)
  *C07H 21/04*   (2006.01)
  *C07K 1/04*    (2006.01)

(52) U.S. Cl. .................. 514/44; 536/23.5; 530/350; 424/450; 424/207.1; 424/233.1; 435/320.1; 435/459

(58) Field of Classification Search ............. None
See application file for complete search history.

*Primary Examiner*—Richard Schnizer
(74) *Attorney, Agent, or Firm*—Medlen & Carroll LLP

(57) ABSTRACT

The present invention provides methods and compositions useful in localized transfer of genetic material or proteins. Moreover, the present invention provides methods and compositions for improving and/or controlling wound healing by applying a wound care device comprising HoxD3 and/or HoxA3 and/or HoxB3. In addition, the present invention provides methods and compositions for improved wound healing in subjects having impaired healing capabilities, such as diabetic subjects.

18 Claims, 14 Drawing Sheets

Control 14 days

+HoxD3 14 days

A 7 days

B 10 days

C 17 days 21 days 42 days

Control      +HoxA3      +HoxD3

SEQUENCE LISTING

<160> NUMBER OF SEQ ID NOS: 24

<210> SEQ ID NO 1
<211> LENGTH: 1251
<212> TYPE: DNA
<213> ORGANISM: Homo sapiens

<400> SEQUENCE: 1

| | | | | | |
|---|---|---|---|---|---|
| atgcagaagg | ctgcttacta | tgaaaaccca | ggactgtttg | gaggctatgg | ctacagcaaa | 60 |
| actacggaca | cttacggcta | cagcaccccc | caccagcccc | acccaccccc | tgctgctgcc | 120 |
| agctccctgg | acactgacta | tccaggttct | gcctgctcca | tccagagctc | tgcccctctg | 180 |
| agagcccag | cccacaaagg | agctgaactc | aatggcagct | gcatgcggcc | gggcactggg | 240 |
| aacagccagg | gtgggggtgg | tggcagccag | cctcctggtc | tgaactcaga | gcagcagcca | 300 |
| ccacaacccc | ctcctccacc | accgaccctg | cccccatctt | cacccaccaa | tcctggaggt | 360 |
| ggagtgcctg | ccaagaagcc | caaggtgggg | cccaatgctt | ctagctcctc | agccaccatc | 420 |
| agcaagcaga | tcttcccctg | gatgaaagag | tctcgacaga | actccaagca | gaagaacagc | 480 |
| tgtgccactg | caggagagag | ctgcgaggac | aagagcccgc | caggcccagc | atccaagcgg | 540 |
| gtacgcacg | catacacgag | cgcgcagctg | gtggaattgg | aaaaggaatt | ccacttcaac | 600 |
| cgctacttgt | gccggccgcg | ccgcgtggag | atggccaacc | tgctgaatct | cacggaacgc | 660 |
| cagatcaaga | tctggttcca | gaaccggcgc | atgaagtaca | agaaggacca | gaaggccaag | 720 |
| ggcatcctgc | actcgccggc | tagccagtcc | cctgagcgca | gcccaccgct | cggcggcgcc | 780 |
| gctggccacg | tggcctactc | cggccagctg | ccgccagtgc | ccggcctggc | ctacgacgcg | 840 |
| ccctcgccgc | ctgctttcgc | caaatcacag | cccaatatgt | acggcctggc | cgcctacacg | 900 |
| gcgccactca | gcagctgcct | gccacaacag | aagcgctacg | cagcgccgga | gttcgagccc | 960 |
| catcccatgg | cgagcaacgg | cggcggcttc | gccagcgcca | acctgcaggg | cagcccggtg | 1020 |
| tacgtgggcg | gcaacttcgt | cgagtccatg | gcgcccgcgt | ccgggcctgt | cttcaacctg | 1080 |
| ggccacctct | cgcacccgtc | gtcggccagc | gtggactaca | gttcgccgc | gcagattcca | 1140 |
| ggcaaccacc | accatggacc | ttgcgaccct | catcccacct | acacagatct | ctcggcccac | 1200 |
| cactcgtctc | agggacgact | gccggaggct | cccaaactga | cgcatctgta | g | 1251 |

<210> SEQ ID NO 2
<211> LENGTH: 416
<212> TYPE: PRT
<213> ORGANISM: Homo sapiens

<400> SEQUENCE: 2

Met Gln Lys Ala Ala Tyr Tyr Glu Asn Pro Gly Leu Phe Gly Gly Tyr
1               5                   10                  15

```
Gly Tyr Ser Lys Thr Thr Asp Thr Tyr Gly Tyr Ser Thr Pro His Gln
             20                  25                  30

Pro Tyr Pro Pro Pro Ala Ala Ala Ser Ser Leu Asp Thr Asp Tyr Pro
         35                  40                  45

Gly Ser Ala Cys Ser Ile Gln Ser Ser Ala Pro Leu Arg Ala Pro Ala
 50                  55                  60

His Lys Gly Ala Glu Leu Asn Gly Ser Cys Met Arg Pro Gly Thr Gly
 65                  70                  75                  80

Asn Ser Gln Gly Gly Gly Gly Ser Gln Pro Pro Gly Leu Asn Ser
                 85                  90                  95

Glu Gln Gln Pro Pro Gln Pro Pro Pro Pro Pro Thr Leu Pro Pro
                100                 105                 110

Cys Ser Pro Thr Asn Pro Gly Gly Val Pro Ala Lys Lys Pro Lys
             115                 120                 125

Gly Gly Pro Asn Ala Ser Ser Ser Ala Thr Ile Ser Lys Gln Ile
 130                 135                 140

Phe Pro Trp Met Lys Glu Ser Arg Gln Asn Ser Lys Gln Lys Asn Ser
145                 150                 155                 160

Cys Ala Thr Ala Gly Glu Ser Cys Glu Asp Lys Ser Pro Pro Gly Pro
                165                 170                 175

Ala Ser Lys Arg Val Arg Thr Ala Tyr Thr Ser Ala Gln Leu Val Glu
             180                 185                 190

Leu Glu Lys Glu Phe His Phe Asn Arg Tyr Leu Cys Arg Pro Arg Arg
             195                 200                 205

Val Glu Met Ala Asn Leu Leu Asn Leu Thr Glu Arg Gln Ile Lys Ile
             210                 215                 220

Trp Phe Gln Asn Arg Arg Met Lys Tyr Lys Lys Asp Gln Lys Ala Lys
225                 230                 235                 240

Gly Ile Leu His Ser Pro Ala Ser Gln Ser Pro Glu Arg Ser Pro Pro
                245                 250                 255

Leu Gly Gly Ala Ala Gly His Val Ala Tyr Ser Gly Gln Leu Pro Pro
             260                 265                 270

Val Pro Gly Leu Ala Tyr Asp Ala Pro Ser Pro Ala Phe Ala Lys
             275                 280                 285

Ser Gln Pro Asn Met Tyr Gly Leu Ala Ala Tyr Thr Ala Pro Leu Ser
290                 295                 300

Ser Cys Leu Pro Gln Gln Lys Arg Tyr Ala Ala Pro Glu Phe Glu Pro
305                 310                 315                 320

His Pro Met Ala Ser Asn Gly Gly Phe Ala Ser Ala Asn Leu Gln
             325                 330                 335

Gly Ser Pro Val Tyr Val Gly Asn Phe Val Glu Ser Met Ala Pro
             340                 345                 350

Ala Ser Gly Pro Val Phe Asn Leu Gly His Leu Ser His Pro Ser Ser
             355                 360                 365

Ala Ser Val Asp Tyr Ser Cys Ala Ala Gln Ile Pro Gly Asn His His
 370                 375                 380

His Gly Pro Cys Asp Pro His Pro Thr Tyr Thr Asp Leu Ser Ala His
385                 390                 395                 400

His Ser Ser Gln Gly Arg Leu Pro Glu Ala Pro Lys Leu Thr His Leu
                405                 410                 415
```

<210> SEQ ID NO 3
<211> LENGTH: 21
<212> TYPE: DNA

```
-continued

<213> ORGANISM: Artificial Sequence
<220> FEATURE:
<223> OTHER INFORMATION: Synthetic

<400> SEQUENCE: 3
agggtcagca ggccctggag c                                              21

<210> SEQ ID NO 4
<211> LENGTH: 26
<212> TYPE: DNA
<213> ORGANISM: Artificial Sequence
<220> FEATURE:
<223> OTHER INFORMATION: Synthetic

<400> SEQUENCE: 4
agagcgggga aggggttcc cgaact                                          26

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
gctgcttact atgaaaaccc agg                                            23

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
cgtaagtgtc cgtagttttg ctgt                                           24

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
tcttaaccac cagatcattc cttct                                          25

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
ccatagtgcg agcaaatggg                                                20

<210> SEQ ID NO 9
<211> LENGTH: 1023
<212> TYPE: DNA
<213> ORGANISM: Homo sapiens

<400> SEQUENCE: 9
atgtcctttc ccaacagctc tcctgctgct aatactttt tagtagattc cttgatcagt     60
gcctgcagga gtgacagttt ttattccagc agcgccagca tgtacatgcc accacctagc   120
```

```
gcagacatgg ggacctatgg aatgcaaacc tgtggactgc tcccgtctct ggccaaaaga      180
gaagtgaacc accaaaatat gggtatgaat gtgcatcctt atatacctca agtagacagt      240
tggacagatc cgaacagatc ttgtcgaata gagcaacctg ttacacagca agtccccact      300
tgctccttca ccaccaacat taaggaagaa tccaattgct gcatgtattc tgataagcgc      360
aacaaactca tttcggccga ggtcccttcg taccagaggc tggtccctga gtcttgtccc      420
gttgagaacc ctgaggttcc cgtccctcga tattttagac tgagtcagac ctacgccacc      480
gggaaaaccc aagagtacaa taatagcccc gaaggcagct ccactgtcat gctccagctc      540
aaccctcgtg gcgcggccaa gccgcagctc tccgctgccc agctgcagat ggaaaagaag      600
atgaacgagc ccgtgagcgg ccaggagccc accaaagtct cccaggtgga gagccccgag      660
gccaaaggcg gccttcccga agagaggagc tgcctggctg aggtctccgt gtccagtccc      720
gaagtgcagg agaaggaaag caagaggaa atcaagtctg atacaccaac cagcaattgg      780
ctcactgcaa agagtggcag aaagaagagg tgcccttaca ctaagcacca aacgctggaa      840
ttagaaaaag agttcttgtt caatatgtac ctcacccgcg agcgccgcct agagatcagt      900
aagagcgtta acctcaccga caggcaggtc aagatttggt tcaaaaccg ccgaatgaaa      960 ctcaagaaga tgagccgaga gaaccggatc cgagaactga ccgccaacct cacgttttct     1020
tag                                                                   1023
```

<210> SEQ ID NO 10
<211> LENGTH: 340
<212> TYPE: PRT
<213> ORGANISM: Homo sapiens

<400> SEQUENCE: 10

```
Met Ser Phe Pro Asn Ser Ser Pro Ala Ala Asn Thr Phe Leu Val Asp
1               5                   10                  15

Ser Leu Ile Ser Ala Cys Arg Ser Asp Ser Phe Tyr Ser Ser Ser Ala
            20                  25                  30

Ser Met Tyr Met Pro Pro Pro Ser Ala Asp Met Gly Thr Tyr Gly Met
        35                  40                  45

Gln Thr Cys Gly Leu Leu Pro Ser Leu Ala Lys Arg Glu Val Asn His
    50                  55                  60

Gln Asn Met Gly Met Asn Val His Pro Tyr Ile Pro Gln Val Asp Ser
65                  70                  75                  80

Trp Thr Asp Pro Asn Arg Ser Cys Arg Ile Glu Gln Pro Val Thr Gln
                85                  90                  95

Gln Val Pro Thr Cys Ser Phe Thr Thr Asn Ile Lys Glu Glu Ser Asn
            100                 105                 110

Cys Cys Met Tyr Ser Asp Lys Arg Asn Lys Leu Ile Ser Ala Glu Val
        115                 120                 125

Pro Ser Tyr Gln Arg Leu Val Pro Glu Ser Cys Pro Val Glu Asn Pro
    130                 135                 140

Glu Val Pro Val Pro Arg Tyr Phe Arg Leu Ser Gln Thr Tyr Ala Thr
145                 150                 155                 160

Gly Lys Thr Gln Glu Tyr Asn Asn Ser Pro Glu Gly Ser Ser Thr Val
                165                 170                 175

Met Leu Gln Leu Asn Pro Arg Gly Ala Ala Lys Pro Gln Leu Ser Ala
            180                 185                 190

Ala Gln Leu Gln Met Glu Lys Lys Met Asn Glu Pro Val Ser Gly Gln
        195                 200                 205
```

```
Glu Pro Thr Lys Val Ser Gln Val Glu Ser Pro Glu Ala Lys Gly Gly
        210                 215                 220
Leu Pro Glu Glu Arg Ser Cys Leu Ala Glu Val Ser Val Ser Ser Pro
225                 230                 235                 240
Glu Val Gln Glu Lys Glu Ser Lys Glu Glu Ile Lys Ser Asp Thr Pro
                245                 250                 255
Thr Ser Asn Trp Leu Thr Ala Lys Ser Gly Arg Lys Lys Arg Cys Pro
            260                 265                 270
Tyr Thr Lys His Gln Thr Leu Glu Leu Glu Lys Glu Phe Leu Phe Asn
        275                 280                 285
Met Tyr Leu Thr Arg Glu Arg Arg Leu Glu Ile Ser Lys Ser Val Asn
    290                 295                 300
Leu Thr Asp Arg Gln Val Lys Ile Trp Phe Gln Asn Arg Arg Met Lys
305                 310                 315                 320
Leu Lys Lys Met Ser Arg Glu Asn Arg Ile Arg Glu Leu Thr Ala Asn
                325                 330                 335
Leu Thr Phe Ser
            340

<210> SEQ ID NO 11
<211> LENGTH: 1126
<212> TYPE: DNA
<213> ORGANISM: Homo sapiens

<400> SEQUENCE: 11
cacaatctct cttcttcaaa ttctttcccc aaaatgtcct ttcccaacag ctctcctgct      60
gctaatactt ttttagtaga ttccttgatc agtgcctgca ggagtgacag ttttttattcc    120 agcagcgcca gcatgtacat gccaccacct agcgcagaca tggggaccta tggaatgcaa    180
acctgtggac tgctcccgtc tctggccaaa agagaagtga accaccaaaa tatgggtatg    240
aatgtgcatc cttatatacc tcaagtagac agttggacag atccgaacag atcttgtcga    300
atagagcaac tgttacaca gcaagtcccc acttgctcct tcaccaccaa cattaaggaa      360
gaatccaatt gctgcatgta ttctgataag cgcaacaaac tcatttcggc cgaggtccct    420
tcgtaccaga ggctggtccc tgagtcttgt cccgttgaga accctgaggt tcccgtccct    480 cgatattta gactgagtca gacctacgcc accgggaaaa cccaagagta caataatagc      540
cccgaaggca gctccactgt catgctccag ctcaaccctc gtggcgcggc caagccgcag    600
ctctccgctg cccagctgca gatggaaaag aagatgaacg agcccgtgag cggccaggag    660
cccaccaaag tctcccaggt ggagagcccc gaggccaaag gcggccttcc gaagagagg      720 agctgcctgg ctgaggtctc cgtgtccagt cccgaagtgc aggagaagga aagcaaagag    780
gaaatcaagt ctgatacacc aaccagcaat tggctcactg caaagagtgg cagaaagaag    840 aggtgcccctt acactaagca ccaaacgctg aattagaaa aagagttctt gttcaatatg     900
tacctcaccc gcgagcgccg cctagagatc agtaagagcg ttaacctcac cgacaggcag    960
gtcaagattt ggtttcaaaa ccgccgaatg aaactcaaga agatgagccg agagaaccgg   1020
atccgagaac tgaccgccaa cctcacgttt tcttaggtct gaggccggtc tgaggccgga   1080
tcagaggcca ggattggaga gggggcaccg cgttccaggg cccagt                  1126

<210> SEQ ID NO 12
<211> LENGTH: 2329
<212> TYPE: DNA
<213> ORGANISM: Homo sapiens
```

<400> SEQUENCE: 12

```
ggcacgaggg cctccacaga tatcaaaaga aacctgaaga gcctacaaaa aaaaaaagag        60
ataaagacaa aattcaagaa aacacacaca tacataattg tggtcacctg gagcctgggg       120
gccggcccag ctctctcagg attcagcaga cattggaggt ggcagtgaag gatacagtgg       180
tagtcaatgt tatttgagca gggtcagcag gccctggagc ttcctgagtg cacaatgcag       240
aaggctgctt actatgaaaa cccaggactg tttggaggct atggctacag caaaactacg       300
gacacttacg gctacagcac cccccaccag ccctacccac ccctgctgc tgccagctcc        360
ctggacactg actatccagg ttctgcctgc tccatccaga gctctgcccc tctgagagcc       420
ccagcccaca aaggagctga actcaatggc agctgcatgc ggccgggcac tgggaacagc       480
cagggtgggg gtggtggcag ccagcctcct ggtctgaact cagagcagca gccaccacaa       540
cccctcctc caccaccgac cctgccccca tcttcaccca ccaatcctgg aggtggagtg        600
cctgccaaga gcccaaagg tgggcccaat gcttctagct cctcagccac catcagcaag        660
cagatcttcc cctggatgaa agagtctcga cagaactcca agcagaagaa cagctgtgcc       720
actgcaggag agagctgcga ggacaagagc ccgccaggcc cagcatccaa gcgggtacgc       780
acggcataca cgagcgcgca gctggtggaa ttggaaaagg aattccactt caaccgctac       840
ttgtgccggc cgcgccgcgt ggagatggcc aacctgctga atctcacgga acgccagatc       900
aagatctggt tccagaaccg cgcatgaag tacaagaagg accagaaggc caagggcatc        960
ctgcactcgc cggctagcca gtcccctgag cgcagcccac cgctcggcgg cgccgctggc      1020
cacgtggcct actccggcca gctgccgcca gtgcccggcc tggcctacga cgcgccctcg      1080
ccgcctgctt tcgccaaatc acagcccaat atgtacggcc tggccgccta cggcgccca      1140
ctcagcagct gcctgccaca acagaagcgc tacgcagcgc cggagttcga gccccatccc      1200
atggcgagca cgcggcgg cttcgccagc gccaacctgc agggcagccc ggtgtacgtg        1260
ggcggcaact tcgtcgagtc catggcgccc gcgtccgggc ctgtcttcaa cctgggccac      1320
ctctcgcacc cgtcgtcggc cagcgtggac tacagttgcg ccgcgcagat tccaggcaac      1380
caccaccatg accttgcga ccctcatccc acctacacag atctctcggc ccaccactcg       1440
tctcagggac gactgccgga ggctcccaaa ctgacgcatc tgtagcggcc gccgccagcc      1500
cgaactcgcg gcaaaattac ctctcttgct gtagtggtgg ggtagagggt ggggcccgcg      1560
gggcagttcg ggaacccct tccccgctct tgccctgccg ccgcctcccg ggtctcaggc       1620
ctccagcggc ggaggcgcag gcgaccgggc ctcccctcca tgggcgtcct ttgggtgact      1680
cgccataaat cagccgcaag gatccttccc tgtaaatttg acagtgccac atactgcgga      1740
ccaagggact ccaatctggt aatggtgtcc caaaggtaag tctgagaccc atcggcggcg      1800
cgccctgcag agggaccaga gcttggagag tcttgggcct ggcccgcgtc tagcttagtt      1860
tcagagacct taatttatat tctccttcct gtgccgtaag gattgcatcg gactaaacta      1920
tctgtatttta ttatttgaag cgagtcattt cgttccctga ttatttatcc ttgtctgaat     1980
gtatttatgt gtatatttgt agatttatcc agccgagctt aggaattcgc ttccaggccg      2040
tgggggccac atttcacctc cttagtcccc ctggtctgaa ctagttgaga gagtagtttt      2100
gaacagtcgt aaccgtggct ggtgtttgta gttgacataa aggattaaga ccgcaaattg      2160
tccttcatgg gtagagtcag gaagcccggt ggcgtggcac aacacacttt ggtcatttct      2220
caaaaaccac agtcctcacc acagtttatt gatttcaaat tgtctggtac tattggaaca      2280
```

-continued

| aatatttaga ataaaaaaat ttcccagtca aaaaaaaaaa aaaaaaaa | 2329 |

<210> SEQ ID NO 13
<211> LENGTH: 5834
<212> TYPE: DNA
<213> ORGANISM: Homo sapiens

<400> SEQUENCE: 13

| gtgatttgaa accaggtggg ggggagaccc tttttttttt tttttttttt taagttctgg | 60 |
| ctgttctgag catgttatag gactttcatt tcccatcaaa accttgtgct gacccaatga | 120 |
| ttgactgatt gatccactta ttaattcacc tattcaacaa gcatttattg cactaactac | 180 |
| atgcagggca ctgtgctgga tgttaggaac agtagacaaa tgacacagcc cctgcctgca | 240 |
| aggagcttac agtttagtgg gcgaatcagc caacaaaatg tctgaggcta taagtacttt | 300 |
| tccacacaga agaaaggtaa atgggcaatc ttgaagaaag taaattgtat ctggaggtag | 360 |
| agggaagccc tttccctcag ctacagttga gctaaaaaga aggaaactct tcttacattt | 420 |
| aggaaaaatt ccttctgata cttccagagg ttcaaataag ttgaacttca taaaatctgc | 480 |
| caggcgcagt ggctcatgcc tgtaattcca gcactttggg aggccaagac gggaggatca | 540 |
| caagagccca ggaactcaag accagcctgg gcaacattgt aagaccctgt ctctacaaaa | 600 |
| aaaaaaaaaa aaaaaactaa gagctggcgc agtggctcac acctgtaatc ccagcactta | 660 |
| gggaggccca gcgggttgat cacctgaggt cagagttcaa gaccaacctg accaacatgg | 720 |
| tgaaaccctg tctctactaa aaatataaaa aattagccag gtgtggtggc aggtgcctgt | 780 |
| aatcccagct actcaggagg ctgaggcagg agaattgctt gaacccagag gcgtaggttg | 840 |
| cagtaagctg agatcatgac actgcactcc agccttggca acaggagcga aattccatct | 900 |
| aaaacaaaac aaaacaaaac aaaacactaa gacatgtagc caggcatggt gggcacctgt | 960 |
| agctactgca gaatagctgg gactttgaaa tactctgaaa tagctattaa taccaggcta | 1020 |
| aagtgggagg atcgcttgag cccagtaaat tgaggctgca gtgagccatg ttcatgccac | 1080 |
| tgcactccag cctgggcaac aagcaagaca ctgtattaat aaataaatag ataagtaaat | 1140 |
| aaactcagat ccagcacctt gcccatctcc ccgccgtgaa gtgggtagga agcagagagc | 1200 |
| atgggctagt ccttctatat tgactggtct tgccaatgac actccctctg ggcctcttg | 1260 |
| cttttcttct gacaggtcac ctggagcctg ggggccggcc cagctctctc aggattcagc | 1320 |
| agacattgga ggtggcagtg aaggatacag tggtagtcaa tgttatttga gcagggtcag | 1380 |
| caggccctgg agcttcctga gtcacaatg cagaaggctg cttactatga aaacccagga | 1440 |
| ctgtttggag gctatggcta cagcaaaact acggacactt acggctacag caccccccac | 1500 |
| cagccctacc cacccccctgc tgctgccagc tccctgaca ctgactatcc aggttctgcc | 1560 |
| tgctccatcc agagctctgc ccctctgaga gccccagccc acaaaggagc tgaactcaat | 1620 |
| ggcagctgca tgcggccggg cactgggaac agccagggtg ggggtggtgg cagccagcct | 1680 |
| cctggtctga actcagagca gcagccacca caacccccctc ctccaccacc gaccctgccc | 1740 |
| ccatgttcac ccaccaatcc tggaggtgga gtgcctgcca agaagcccaa aggtgggccc | 1800 |
| aatgcttcta gctcctcagc caccatcagc aagcagatct tccctggat gaaagagtct | 1860 |
| cgacagaact ccaagcagaa gaacagctgt gccactgcag gtagctccct gaggtggcct | 1920 |
| actgccagac caagcccccct ccagattgac ccaaggaagc ctagtcaggg ctggaaatgc | 1980 |
| aaccttggag gtcatatgtc taaactccta ctcacgtcaa aatgttcttt tttttagtgt | 2040 |
| tcctgattgg ggtcatgacc ttgcagtgac agggtgctcc cttccattcc aggctgctgg | 2100 |

```
tgctgttgct ggacaggtct tatagctatt aatagagagt gcttccttat atgggcatat    2160
ctgttttcct gggctgctaa ttataactcc attccctctt ccacccaaca gctcttcaag    2220
atttgaagat aggtattaca atccccaagc ctaggtgatt atatagccca tcacacga     2280 atctcattcc cttaaactca taaaaactaa agtcttagaa agtaccatac taagtacttt    2340
ctaagcatta tctaatttaa tttttcaaag aaccttttga ggtaggtata tgataacatc    2400
cccattttac agataagaaa actgttagag aggataggca acttgcccaa gattctgaaa    2460
ctgcaaagtg gtggatttga atccagtcag tctggcttta ggggctgcta agcataacca    2520
tgagtctcta tttggccacc tcagcccaat tctcccactc cagcaaatcc ataatgggga    2580
ggtgcctgtc ctagtaggag aggatattct gggagacagt aacagccttg gatttctcta    2640
actggaaggg gagcccctcc agttgggcct tctctaggtc cacccagggc atgtagaaga    2700
taggcatggc caggaactct gagggctgtt ccttctctct gcttagactg cttggttcct    2760
gaaattttct gaccttgtgg tatctgatgt ggtttatctt caggtagatg aacttgcttc    2820
caggtccagg gcaagtttgg ggcctggggt gtggcttgct atcagggatc tggtttgcct    2880
gatgttttct ggggctgctg ctcctaggga gagggtatta tcctgcctgc aacctccttt    2940
tcctgcccct ccttcctcag ctgcaggctc aggccctccc tcccaggaga atccatttg    3000 tcttccctgg gagggagtgg acaagcagct gagaggtggc agggtagtaa aagccagtgt    3060
tgaggctgct gctcctagca ctgtgaatac tcaaaatgct tccagcctgg ccttggactc    3120
cctaaaatac ccaggcagtg ttttttttg tttgtttgtt tggttggttt ttttttattt    3180
tttatttttt tgtttgtcac ctccctggct ttgagtgcag ttgggctgca gtggggcgcc    3240
aagatctcca tccccatact ttgctggggg ttggtggggg gctttgccca gaggccagct    3300
cctaagcaag gcaggctgga gctatttcct cttcctttcc ttctccatac cccaccctg    3360 gcagcagagc tgggaggag tgttcaaagg agtctggccc ttctttgaca gagggaggcc    3420
ttaccagctg ctcctggtct ctcattaaac tctttcatgg cctttgggtg gtatgggtt    3480 gatggactag gctgcagggg agagggtggg cagagtgaac tggatctcag aaggctgatg    3540
gaggtttcag gtgcgactga taggtaggcc tagtaggggg ttggtaggta ggtgaattcc    3600
cccttggaat catacctctc aaacggccct tcccctcccc agccaggatt ggaggtgggg    3660
ggagggagga ggaaaagaga accagggaag caccctctc cagtcctgag ggtccccacc    3720
caactcactc agcgccctcc ctctctccct ccctgcccag gagagagctg cgaggacaag    3780
agcccgccag gcccagcatc caagcgggta cgcacggcat acacgagcgc gcagctggtg    3840
gaattggaaa aggaattcca cttcaaccgc tacttgtgcc ggccgcgccg cgtggagatg    3900
gccaacctgc tgaatctcac ggaacgccag atcaagatct ggttccagaa ccggcgcatg    3960
aagtacaaga aggaccagaa ggccaagggc atcctgcact cgccggctag ccagtcccct    4020
gagcgcagcc caccgctcgg cggcgccgct ggccacgtgg cctactccgg ccagctgccg    4080
ccagtgcccg gcctggccta cgacgcgccc tcgccgctg cttcgccaa atcacagccc    4140 aatatgtacg gcctggccgc ctacacggcg ccactcagca gctgcctgcc acaacagaag    4200
cgctacgcag cgccggagtt cgagcccat cccatggcga gcaacggcgg cggcttcgcc    4260
agcgccaacc tgcagggcag cccggtgtac gtgggcggca acttcgtcga gtccatggcg    4320
cccgcgtccg ggcctgtctt caacctgggc cacctctcgc accgtcgtc ggccagcgtg    4380 gactacagtt gcgccgcgca gattccaggc aaccaccacc atggaccttg cgaccctcat    4440
```

```
cccacctaca cagatctctc ggcccaccac tcgtctcagg gacgactgcc ggaggctccc    4500
aaactgacgc atctgtagcg gccgccgcca gcccgaactc gcggcaaaat tacctctctt    4560
gctgtagtgg tggggtagag ggtgggccc gcggggcagt tcgggaaccc ccttccccgc     4620
tcttgccctg ccgccgcctc ccgggtctca ggcctccagc ggcggaggcg caggcgaccg    4680
ggcctcccct ccatgggcgt cctttgggtg actcgccata aatcagccgc aaggatcctt    4740
ccctgtaaat ttgacagtgc cacatactgc ggaccaaggg actccaatct ggtaatggtg    4800
tccaaaggta agtctgagac ccatcggcgg cgcccctgca gagggaccag agcttggaga    4860
gtcttgggcc tggcccgcgt ctagcttagt ttcagagacc ttaatttata ttctccttcc    4920
tgtgccgtaa ggattcgatc ggactaaact atctgtattt attatttgaa gcgagtcatt    4980
tcgttccctg attatttatc cttgtctgaa tgtatttatg tgtatatttg tagatttatc    5040
cagccgagct taggaattcg cttccaggcc gtggggccca catttcacct ccttagggcc    5100
cctggtctga actagttgag agagtagttt tgaacagtcg taaccgtggc tggtgtttgt    5160
agttgacata aaggattaag accgcaaatt gtccttcatg ggtagagtca ggaagcccgg    5220
tggcgtggca caacacactt tggtcatttc tcaaaaacca cagtcctcac cacagtttat    5280
tgatttcaaa ttgtctggta ctattggaac aaatatttag aataaaaaaa tttcccagtc    5340
agaagtgtat ctgtgttaat catgcacact tcgaagcaga tcactatgcc tttatctcgc    5400
acaatcccca tggaaggccc cgaaacagac tgacactttg aaaaaaatat tttatttatt    5460
tggagtctag tgcataaatt ggttctcggg atacttgatt actttccagc tattgaaatt    5520
aggggagggg gaaatgagga tgcaaaccta agaaggttct gggcgggatg atttgggcag    5580
ggcttttga aagcagcgcc tgctttgctg tttttactgc cttctttcta gacacaatcg     5640
acttttacac tgggggcccc agagctcact tttctgcatt aagtaacaaa aataaaactt    5700
tgaaagaaaa ctgacaatca aagaaaaaac acaagagaag ttgtaagaag aattgagcta    5760
tgaaaaagct aaggtgtaga aaaagaaacc atcatttgga gacgcgtacc taagctttt     5820
ctctaggaaa tgct                                                       5834
```

<210> SEQ ID NO 14
<211> LENGTH: 1335
<212> TYPE: DNA
<213> ORGANISM: Homo sapiens

<400> SEQUENCE: 14

```
atgcaaaaag cgacctacta cgacagctcg gcgatctacg gtggctaccc ctaccaggca     60
gccaacgggt tcgcttataa tgccaatcag cagccgtacc cggcgtccgc cgctttgggc    120
gccgacggcg agtaccaccg acccgcctgc tccctccagt ctccctccag cgccggggc     180
cacccccaagg cacacgaact gagtgaggcg tgcctgcgca ccctgagcgc cccacctagc    240
cagcctccaa gctgggagag accgcccctg caccccgccgc cgcccccaggc gcgcccccct    300
gccccacagc cgcctcagcc cgcacctcag cccctgcac ctacccctgc gcgccccg      360
cctcccctctt ctgcctcccc tcctcagaat gccagcaaca ccctaccccc tgccaacgcg    420
gccaagagcc cctgctcaa ctcacccaca gtggccaaac aaatcttccc ctggatgaaa    480
gagtctcgac aaaacacaaa gcagaaaacc agcagctcca gctcaggcga agctgcgct    540
ggcgacaaga gccgccgggg gcaggcttcg tccaagcgcg cgcgcacggc ctacacgagc    600
gcgcagctgg tggagctgga gaaagagttc cacttcaacc gctacctgtg ccggccgcgc    660
cgggtggaga tggccaatct gctgaacctc actgagcgcc agatcaagat ctggttccag    720
```

```
aatcgccgca tgaagtacaa aaaggatcag aagggcaagg gcatgctaac gtcatcgggg      780
ggccagtctc caagtcgcag ccccgtgccc cccggagccg gtggctatct gaactctatg      840
cattcgctgg tcaacagcgt cccgtatgag ccccagtcgc cccgcccttt ctccaagccc      900
ccccagggta cctacgggct gccccccgcc tcctaccctg cgtccctgcc cagctgcgca      960
cccccgccac cccacagaa gcgctacacg gcggcagggg cgggcgcagg ggcaccccc     1020 gactatgacc cgcacgctca tggcctgcag ggcaacggca gctatgggac cccacacata     1080
cagggaagcc ccgtcttcgt gggggcagc tatgtggagc ccatgagcaa ctccgggcca     1140
gccctctttg gtctaactca cctcccccac gctgcctcgg gcgccatgga ctatgggggt     1200
gccgggccgc tgggcagcgg ccaccaccac gggccgggc ctggggagcc gcaccccacc     1260
tacacggacc ttaccggcca ccatccttct cagggaagaa ttcaggaagc acccaagctc     1320
acccacctgt gatag                                                     1335
```

<210> SEQ ID NO 15
<211> LENGTH: 443
<212> TYPE: PRT
<213> ORGANISM: Homo sapiens

<400> SEQUENCE: 15

```
Met Gln Lys Ala Thr Tyr Tyr Asp Ser Ser Ala Ile Tyr Gly Gly Tyr
1               5                   10                  15

Pro Tyr Gln Ala Ala Asn Gly Phe Ala Tyr Asn Ala Asn Gln Gln Pro
            20                  25                  30

Tyr Pro Ala Ser Ala Ala Leu Gly Ala Asp Gly Glu Tyr His Arg Pro
        35                  40                  45

Ala Cys Ser Leu Gln Ser Pro Ser Ser Ala Gly Gly His Pro Lys Ala
    50                  55                  60

His Glu Leu Ser Glu Ala Cys Leu Arg Thr Leu Ser Ala Pro Pro Ser
65                  70                  75                  80

Gln Pro Pro Ser Leu Gly Glu Pro Pro Leu His Pro Pro Pro Gln
                85                  90                  95

Ala Ala Pro Pro Ala Pro Gln Pro Pro Gln Pro Ala Pro Gln Pro Pro
            100                 105                 110

Ala Pro Thr Pro Ala Ala Pro Pro Pro Ser Ser Ala Ser Pro Pro
        115                 120                 125

Gln Asn Ala Ser Asn Asn Pro Thr Pro Ala Asn Ala Ala Lys Ser Pro
    130                 135                 140

Leu Leu Asn Ser Pro Thr Val Ala Lys Gln Ile Phe Pro Trp Met Lys
145                 150                 155                 160

Glu Ser Arg Gln Asn Thr Lys Gln Lys Thr Ser Ser Ser Ser Gly
                165                 170                 175

Glu Ser Cys Ala Gly Asp Lys Ser Pro Pro Gly Gln Ala Ser Ser Lys
            180                 185                 190

Arg Ala Arg Thr Ala Tyr Thr Ser Ala Gln Leu Val Glu Leu Glu Lys
        195                 200                 205

Glu Phe His Phe Asn Arg Tyr Leu Cys Arg Pro Arg Arg Val Glu Met
    210                 215                 220

Ala Asn Leu Leu Asn Leu Thr Glu Arg Gln Ile Lys Ile Trp Phe Gln
225                 230                 235                 240

Asn Arg Arg Met Lys Tyr Lys Lys Asp Gln Lys Gly Lys Gly Met Leu
                245                 250                 255
```

```
Thr Ser Ser Gly Gly Gln Ser Pro Ser Arg Ser Pro Val Pro Pro Gly
                260                 265                 270

Ala Gly Gly Tyr Leu Asn Ser Met His Ser Leu Val Asn Ser Val Pro
            275                 280                 285

Tyr Glu Pro Gln Ser Pro Pro Phe Ser Lys Pro Pro Gln Gly Thr
        290                 295                 300

Tyr Gly Leu Pro Pro Ala Ser Tyr Pro Ala Ser Leu Pro Ser Cys Ala
305                 310                 315                 320

Pro Pro Pro Pro Gln Lys Arg Tyr Thr Ala Ala Gly Ala Gly Ala
                325                 330                 335

Gly Gly Thr Pro Asp Tyr Asp Pro His Ala His Gly Leu Gln Gly Asn
            340                 345                 350

Gly Ser Tyr Gly Thr Pro His Ile Gln Gly Ser Pro Val Phe Val Gly
            355                 360                 365

Gly Ser Tyr Val Glu Pro Met Ser Asn Ser Gly Pro Ala Leu Phe Gly
        370                 375                 380

Leu Thr His Leu Pro His Ala Ala Ser Gly Ala Met Asp Tyr Gly Gly
385                 390                 395                 400

Ala Gly Pro Leu Gly Ser Gly His His Gly Pro Gly Pro Gly Glu
                405                 410                 415

Pro His Pro Thr Tyr Thr Asp Leu Thr Gly His His Pro Ser Gln Gly
            420                 425                 430

Arg Ile Gln Glu Ala Pro Lys Leu Thr His Leu
        435                 440

<210> SEQ ID NO 16
<211> LENGTH: 3259
<212> TYPE: DNA
<213> ORGANISM: Homo sapiens

<400> SEQUENCE: 16
tctcactagc ctcagagcac tctcagaagt tcagaaacta agaccagaaa agagaagatt      60
tttagacagc tcatgaaacg gtctgcgcgg ggcggccatt ggcggcggag tgtcacgtga     120 ccgcggggc gtgccaatgt gcgccctcac gggtgtcaaa cccctgtcag agtgtgcgat     180
caagatcgtg aaacaacgcg atgcaaaaag cgacctacta cgacagctcg gcgatctacg     240
gtggctaccc ctaccaggca gccaacgggt tcgcttataa tgccaatcag cagccgtacc     300
cggcgtccgc cgctttgggc gccgacggcg agtaccaccg accgcctgc tccctccagt     360 ctccctccag cgccgggggc caccccaagg cacacgaact gagtgaggcg tgcctgcgca     420
ccctgagcgc cccacctagc cagcctccaa gcctgggaga ccgcccctg cacccgccgc     480 cgccccaggc cgcgcccct gccccacagc cgcctcagcc cgcacctcag cccccctgcac     540 ctaccccctgc cgcgcccccg cctccctctt ctgcctcccc tcctcagaat gccagcaaca     600 accctaccc tgccaacgcg ccaagagcc cctgctcaa ctcacccaca gtggccaaac     660
aaatcttccc ctggatgaaa gagtctcgac aaaacacaaa gcagaaaacc agcagctcca     720
gctcaggcga agctgcgct ggcgacaaga gcccgccggg gcaggcttcg tccaagcgcg     780
cgcgcacggc ctacacgagc gcgcagctgg tggagctgga gaaagagttc cacttcaacc     840
gctacctgtg ccgccgcgc cggtggaga tggccaatct gctgaacctc actgagcgcc     900
agatcaagat ctggttccag aatcgccgca tgaagtacaa aaaggatcag aagggcaagg     960
gcatgctaac gtcatcgggg ggccagtctc caagtcgcag cccccgtgccc ccggagccg    1020 gtggctatct gaactctatg cattcgctgg tcaacagcgt cccgtatgag cccccagtcgc   1080
```

| | | | | |
|---|---|---|---|---|
| ccccgccctt | ctccaagccc | ccccagggta | cctacgggct | gccccccgcc tcctaccctg | 1140 |
| cgtccctgcc | cagctgcgca | ccccgccac | ccccacagaa | gcgctacacg gcggcagggg | 1200 |
| cgggcgcagg | gggcaccccc | gactatgacc | cgcacgctca | tggcctgcag ggcaacggca | 1260 |
| gctatgggac | cccacacata | cagggaagcc | ccgtcttcgt | gggggcagc tatgtggagc | 1320 |
| ccatgagcaa | ctccgggcca | gccctctttg | gtctaactca | cctcccccac gctgcctcgg | 1380 |
| gcgccatgga | ctatgggggt | gccgggccgc | tgggcagcgg | ccaccaccac gggccggggc | 1440 |
| ctggggagcc | gcaccccacc | tacacggacc | ttaccggcca | ccatccttct cagggaagaa | 1500 |
| ttcaggaagc | acccaagctc | acccacctgt | gatagtgggc | ttggggctac gcgccaggag | 1560 |
| agtctccccc | cacccacctt | ttttctttgg | ttgctttttt | tttttttttt aggttcttcc | 1620 |
| tgcccttccc | ttccttcctt | ttctctcttc | tccgcccgc | actccgtttc ccggtttccc | 1680 |
| ccctcgttgg | taaggcgttt | ttatagttta | tgtgacgtag | caatcttggt tgctggaatg | 1740 |
| gctgtatcat | agcgatattt | atctcttcct | gctcctcgat | aggccactgg ccctgcaccc | 1800 |
| tttaccttct | ccactctttg | atcagaaaca | gggtatatga | acaaattttc tagtcgagtt | 1860 |
| ttcaatgtga | atttgttctt | acattatggc | tcccgagggg | aagcgattac ttttttttaat | 1920 |
| tttaaatttt | tttttttaat | tgcacttctt | gtaaagagtg | agaaaaaaaa tcaaaggcgc | 1980 |
| tttgaaacag | gggctctctg | tgcaaggatg | actaagtgta | cgtctttccg tgtgtgtatg | 2040 |
| ctggtgaaca | gtcagattta | tttatatttt | tttgcaagca | ttgaataatc taagttttaa | 2100 |
| atattattta | tccccatccg | ttcgtattta | tattaaagaa | ttctgtaccc tgatggttca | 2160 |
| gaagggttct | tgggcctttt | gttcaattgt | gtattggcgt | acttagaatt tttttttattt | 2220 |
| gaaagagaaa | tataattcct | ttaaacggta | acgatgcaat | aaaaccagag aagatccagc | 2280 |
| ttttgaaaac | agtgatttag | gtttgtaaca | tccggcaaaa | ctgaaaaaaa aaatctgtaa | 2340 |
| acgcgaaaaa | tactagattt | gttttgagag | ttcttcattc | cttgctgctc acattctgag | 2400 |
| aaacaaaaag | aaataaagtt | tttattctga | ataatatccg | tgttaagaag gggttctttg | 2460 |
| gccgaagacg | tgggtctgcg | tggaattcag | gccgaggcga | gccggcagag caggccggac | 2520 |
| gcagcagccc | tctggctcca | gcatggggcc | tggccaggct | attcgcctgg aagctcggcg | 2580 |
| aattctcagg | atggcggctg | gggctccagg | cggctgcggc | agctctggta acgccgtgcg | 2640 |
| gcgggccagc | tgggctgccc | ggttcccagc | tgctgcggag | gcaggctgag ggcgcagggg | 2700 |
| ctgccgagtg | ctgtgcacgg | aagaaacaaa | gacatcccgg | cccaaggcgc agcgggagcg | 2760 |
| cacaggtgcc | ccgcggccca | gccgggggat | aacgcagggc | ggtcttctgc tccatgctct | 2820 |
| tcctcgggtc | aaagcggacc | aactaacgcc | taaacctcgg | tattagccag ccgcgcagag | 2880 |
| gatgccgagc | actttccggg | agcaatcgga | ctcctggtct | cctctgggga tgcttcgcgg | 2940 |
| tctgttatcg | cgtcaggagg | aaagaattgc | tccaaaaatc | tgcacgcgga gcgaaacagt | 3000 |
| ttgaaaggga | ctgaggctca | cccaggtctc | cagcaaacgg | aggactgaac tggggagagt | 3060 |
| caccctgagc | cagcccttcc | ctggactgcc | ggaatcccag | cattagcttc ctgctgaatg | 3120 |
| tagtatttgg | cattctctga | atttatttcc | tctccttccc | ccacccagct ttctttttat | 3180 |
| ggccccaggg | ggagggggag | agagcaagga | gatcggtatc | tttgtaataa aactgcaatt | 3240 |
| ttataaaaaa | aaaaaaaaa | | | | 3259 |

<210> SEQ ID NO 17
<211> LENGTH: 25
<212> TYPE: DNA

<213> ORGANISM: Artificial Sequence
<220> FEATURE:
<223> OTHER INFORMATION: Synthetic

<400> SEQUENCE: 17
tgcgatcaag atcgtgaaac aacgc                                            25

<210> SEQ ID NO 18
<211> LENGTH: 25
<212> TYPE: DNA
<213> ORGANISM: Artificial Sequence
<220> FEATURE:
<223> OTHER INFORMATION: Synthetic

<400> SEQUENCE: 18
agactctcct ggcgcgtagc cccaa                                            25

<210> SEQ ID NO 19
<211> LENGTH: 26
<212> TYPE: DNA
<213> ORGANISM: Artificial Sequence
<220> FEATURE:
<223> OTHER INFORMATION: Synthetic

<400> SEQUENCE: 19
cgatgcagaa agccacctac tacgac                                           26

<210> SEQ ID NO 20
<211> LENGTH: 23
<212> TYPE: DNA
<213> ORGANISM: Artificial Sequence
<220> FEATURE:
<223> OTHER INFORMATION: Synthetic

<400> SEQUENCE: 20
cgccgacccc gggggctct tct                                               23

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
ggaattcggc caccatgcag a                                                21

<210> SEQ ID NO 22
<211> LENGTH: 1296
<212> TYPE: DNA
<213> ORGANISM: Homo sapiens

<400> SEQUENCE: 22
atgcagaaag ccacctacta cgacaacgcc gcggctgctc tcttcggagg ctattcctcg      60
taccctggca gcaatggctt cggcttcgat gtcccccccc aaccccccat tcaggccgcc     120
acgcacctgg agggcgacta ccagcgctca gcttgctcgc tgcagtccct gggcaacgct     180
gccccacatg ccaagagcaa ggagctcaac ggcagctgca tgaggccggg tctggccccc     240
gagaccctgt cggccccgcc tggctcaccc cgcccagtg ccgcacctac cagtgccact      300
agcaacagca gtaatggggg cgggcccagc aaaagtggtc cccaaagtg cggtcccggc      360 accaactcca ccctcaccaa acagatattc ccctggatga agagtcgag gcaaacgtcc      420 aagctgaaaa acaactcccc cggcacagca gagggctgtg gtggcggcgg cggtggcggc      480

```
ggcggcggag gcagtggtgg cagcgggggc ggtggcggcg cggcggggg agggacaag      540 agccccccgg ggtcggcggc gtccaagcgg gcgcggacgg cgtacacgag cgcgcagctg    600
gtggagctgg agaaggagtt ccattttaac cgctacctgt gccggcctcg ccgtgtagag    660
atggccaacc tgctgaacct cagcgagcgg cagatcaaga tctggttcca gaaccggcgc    720
atgaagtaca agaaggacca gaaggccaag ggattggcct cgtcgtcggg gggcccatct    780
ccagccggca gccccccgca gcccatgcag tccacggccg gcttcatgaa cgccttacac    840
tccatgaccc ccagctacga gagcccgtcc ccacccgcct cggtaaagc ccaccagaat     900 gcctacgcgc tgccctccaa ctaccagccc cctctcaaag gctgcggcgc ccgcagaag     960 taccctccga ccccggcgcc cgagtatgag ccgcacgtcc tccaagccaa cgggggcgcc   1020
tacgggacgc ccaccatgca gggcagtccg gtgtacgtgg gcggggcgg ctacgcggat    1080 ccgctgccgc ccctgccgg cccctcctc tatggcctca accacctttc ccatcaccct     1140
tccgggaacc tggactacaa cggggcgccc cctatggcgc ccagccagca ccacggaccc   1200
tgcgaacccc accccaccta cacagacctc tcctctcacc acgcgcctcc tcctcagggt   1260
agaatccaag aagcgcccaa attaacacac ctgtga                              1296
```

<210> SEQ ID NO 23
<211> LENGTH: 431
<212> TYPE: PRT
<213> ORGANISM: Homo sapiens

<400> SEQUENCE: 23

```
Met Gln Lys Ala Thr Tyr Tyr Asp Asn Ala Ala Ala Leu Phe Gly
 1               5                  10                  15

Gly Tyr Ser Ser Tyr Pro Gly Ser Asn Gly Phe Gly Phe Asp Val Pro
                20                  25                  30

Pro Gln Pro Pro Phe Gln Ala Ala Thr His Leu Glu Gly Asp Tyr Gln
            35                  40                  45

Arg Ser Ala Cys Ser Leu Gln Ser Leu Gly Asn Ala Ala Pro His Ala
        50                  55                  60

Lys Ser Lys Glu Leu Asn Gly Ser Cys Met Arg Pro Gly Leu Ala Pro
65                  70                  75                  80

Glu Thr Leu Ser Ala Pro Pro Gly Ser Pro Pro Ser Ala Ala Pro
                85                  90                  95

Thr Ser Ala Thr Ser Asn Ser Ser Asn Gly Gly Gly Pro Ser Lys Ser
            100                 105                 110

Gly Pro Pro Lys Cys Gly Pro Gly Thr Asn Ser Thr Leu Thr Lys Gln
        115                 120                 125

Ile Phe Pro Trp Met Lys Glu Ser Arg Gln Thr Ser Lys Leu Lys Asn
    130                 135                 140

Asn Ser Pro Gly Thr Ala Glu Gly Cys Gly Gly Gly Gly Gly Gly
145                 150                 155                 160

Gly Gly Gly Gly Ser Gly Gly Ser Gly Gly Gly Gly Gly Gly
                165                 170                 175

Gly Gly Asp Lys Ser Pro Pro Gly Ser Ala Ala Ser Lys Arg Ala Arg
            180                 185                 190

Thr Ala Tyr Thr Ser Ala Gln Leu Val Glu Leu Glu Lys Glu Phe His
        195                 200                 205

Phe Asn Arg Tyr Leu Cys Arg Pro Arg Arg Val Glu Met Ala Asn Leu
    210                 215                 220
```

```
Leu Asn Leu Ser Glu Arg Gln Ile Lys Ile Trp Phe Gln Asn Arg Arg
225                 230                 235                 240

Met Lys Tyr Lys Lys Asp Gln Lys Ala Lys Gly Leu Ala Ser Ser Ser
            245                 250                 255

Gly Gly Pro Ser Pro Ala Gly Ser Pro Pro Gln Pro Met Gln Ser Thr
        260                 265                 270

Ala Gly Phe Met Asn Ala Leu His Ser Met Thr Pro Ser Tyr Glu Ser
    275                 280                 285

Pro Ser Pro Pro Ala Phe Gly Lys Ala His Gln Asn Ala Tyr Ala Leu
290                 295                 300

Pro Ser Asn Tyr Gln Pro Leu Lys Gly Cys Gly Ala Pro Gln Lys
305                 310                 315                 320

Tyr Pro Pro Thr Pro Ala Pro Glu Tyr Glu Pro His Val Leu Gln Ala
                325                 330                 335

Asn Gly Gly Ala Tyr Gly Thr Pro Thr Met Gln Gly Ser Pro Val Tyr
                340                 345                 350

Val Gly Gly Gly Tyr Ala Asp Pro Leu Pro Pro Ala Gly Pro
        355                 360                 365

Ser Leu Tyr Gly Leu Asn His Leu Ser His His Pro Ser Gly Asn Leu
        370                 375                 380

Asp Tyr Asn Gly Ala Pro Pro Met Ala Pro Ser Gln His His Gly Pro
385                 390                 395                 400

Cys Glu Pro His Pro Thr Tyr Thr Asp Leu Ser Ser His His Ala Pro
                405                 410                 415

Pro Pro Gln Gly Arg Ile Gln Glu Ala Pro Lys Leu Thr His Leu
                420                 425                 430

<210> SEQ ID NO 24
<211> LENGTH: 2603
<212> TYPE: DNA
<213> ORGANISM: Homo sapiens

<400> SEQUENCE: 24
ctgggtaggg cagggggaac cgacaggccg gtgtccccag ccgcaaaaga gctgctgaac      60
tgtccgttta atgctgctg ggagactcgt aaaaaaatca tcgtggacct ggaggatgag     120 agggcgagc tttatttcgg tcggattgcg cgtgtggtggt ttagctgcaa ggggatgccg     180
cagccccagt tgaggggaa atagttctt aaaaagcata tgccccccta aggaatgtct      240
ctaaagaacc aaatcaaagc tgctctttgg aaggtatgaa tagaatttaa aaaaaaaga     300 tttctatgga gcttaaagtt cacagccatt ctgtgtagac aagagctaag aaaaatgtga     360
gaattataca gaaaaccatt aatcacttct tttctttaaa tacgtatcct ctctcctttg     420
ttattattca acagcaaatc tccttggacc ggctgttggg ggaaaaaagt gttagccgtc     480
tctcccggat ctgcaagggg gaaaaaattt ggaaccataa agttgaaaac ttttttctct     540
cagtttggaa gaagcccttc gtcatgaatg ggatctgcag agttcgggcg agaggaggcg     600
agaggcgcaa aggaggggag atttgtcgcc tgccgctcgc tctggggctc gatgtgaata     660
tatattatgt ctgcctgttc tccctcgtc ggtggctaag gtcagccgct tggaacagac     720
cccggaggag gggggcagag agggaggtg ggggggggg gtccggcgt gtcacgtgac     780 ccccagggtt gccaatgtcc ggtcctgagg gtatcaggcc tttccaagtt gccacccact     840
gcccaggcct cacccagcga tgcagaaagc cacctactac gacaacgccg cggctgctct     900
cttcggaggc tattcctcgt accctggcag caatggcttc ggcttcgatg tccccccca      960
```

-continued

```
accccccattt caggccgcca cgcacctgga gggcgactac cagcgctcag cttgctcgct    1020
gcagtccctg ggcaacgctg ccccacatgc caagagcaag gagctcaacg gcagctgcat    1080
gaggccgggt ctggccccg agaccctgtc ggccccgcct ggctcacccc cgcccagtgc     1140
cgcacctacc agtgccacta gcaacagcag taatggggc gggcccagca aaagtggtcc     1200
cccaaagtgc ggtcccggca ccaactccac cctcaccaaa cagatattcc cctggatgaa    1260
agagtcgagg caaacgtcca agctgaaaaa caactccccc ggcacagcag agggctgtgg    1320
tggcggcggc ggtggcggcg gcggcggagg cagtggtggc agcggggcg gtggcggcgg     1380 cggcgggga ggggacaaga gccccccggg gtcggcggcg tccaagcggg cgcggacggc     1440
gtacacgagc gcgcagctgg tggagctgga gaaggagttc cattttaacc gctacctgtg    1500
ccggcctcgc cgtgtagaga tggccaacct gctgaacctc agcgagcggc agatcaagat    1560
ctggttccag aaccggcgca tgaagtacaa gaaggaccag aaggccaagg gattggcctc    1620
gtcgtcgggg ggcccatctc cagccggcag ccccccgcag cccatgcagt ccacggccgg    1680
cttcatgaac gccttacact ccatgacccc cagctacgag agcccgtccc cacccgcctt    1740
cggtaaagcc caccagaatg cctacgcgct gcctccaac taccagcccc ctctcaaagg     1800
ctgcggcgcc ccgcagaagt accctccgac cccggcgccc gagtatgagc cgcacgtcct    1860
ccaagccaac ggggcgcct acgggacgcc caccatgcag ggcagtccgg tgtacgtggg     1920
cgggggcggc tacgcggatc cgctgccgcc ccctgccggc ccctccctct atggcctcaa    1980
ccacctttcc catcacccct ccgggaacct ggactacaac ggggcgcccc ctatggcgcc    2040
cagccagcac cacggaccct gcgaaccca ccccacctac acagacctct cctctcacca    2100
cgcgcctcct cctcagggta gaatccaaga agcgcccaaa ttaacacacc tgtgatggga   2160
aagggcgaac gaggattagg ggatggggag gaagagagag actgtggagc tctgggggc    2220 aacctggagg tctgaaaaga ggagccagag aaggtggtac ccaggcttcc tggtcagaac   2280
cggcctggag ctccttccct tccccctggc ctgagaggtt gcttttaagt cttccacccc   2340
ttgttccatc tgcctgccaa cccatccgaa aggaatccac atcatattgg agatgacccc   2400
atcaacccca gggctccagc actaccaagt tggaattcca cgcccgggag tggggtagag   2460
gaagacgaga caggacgagg cagaaaagca cattttaaaa accagacaag atggctaggc   2520
catcaccaac caacggactt accttacatc tttgtaggta attccccca aatcttgatt    2580 ttttttttcc tcaattatcc ttt                                           2603
```

HOXD3, HOXA3, AND HOXB3 COMPOSITIONS AND METHODS FOR IMPROVED WOUND HEALING

This application is a Continuation-in-Part of U.S. Ser. No. 10/305,667, filed on Nov. 26, 2002, which is a Continuation-in-Part and claims benefit of international patent application PCT/US02/19020, filed on Jun. 14, 2002, which claims benefit of provisional patent application U.S. Ser. No. 60/298,688, filed on Jun. 14, 2001, and provisional patent application U.S. Ser. No. 60/307,632, filed on Jul. 24, 2001.

The invention was made in part with Government support from the National Institutes of Health, Grants K08 GM00674-01, P50 GM27345, and RO1 CA85249. As such, the Government has certain rights in the invention.

FIELD OF THE INVENTION

The present invention provides methods and compositions useful in localized transfer of genetic material or proteins. Moreover, the present invention provides methods and compositions for improving and/or controlling wound healing by applying a wound care device comprising HoxD3 and/or HoxA3 and/or HoxB3. In addition, the present invention provides methods and compositions for improved wound healing in subjects having impaired healing capabilities, such as diabetic subjects.

BACKGROUND OF THE INVENTION

Various methods are available for the transfer of genetic information and proteins to cells. However, there remains a need in the art to provide localized, high efficiency transfer of genetic information and proteins to cells and tissues, such that long-term benefits are provided. In particular, methods and compositions are needed for settings such as wound healing.

For example, during the process of healing, infection can occur. Indeed, infections represent a significant health risk to various patients, including hospitalised individuals, as well as those with underlying disease conditions and/or immune defects. In particular, wounds and infections represent a serious risk to diabetic patients. These patients often experience slow and/or incomplete wound healing, ulceration of the extremities, and are prone to infection. In diabetic patients, ulcers are often large, open wounds that can involve both soft tissue and the underlying bone. The problem is widespread, as approximately 15% of all diabetics develop ulcers. Infections within these ulcers are difficult to successfully treat, due to poor circulation at these sites (e.g., limiting the potential for systemically administered antimicrobial treatments to reach the wound sites). In extreme cases, limb amputation becomes necessary. Indeed, these amputations account for half of all amputations done in the U.S. Thus, wounds and ulcers of diabetic patients often represent life threatening conditions for diabetic subjects.

Current treatment of diabetic wounds or ulcers consists of debridement, packing the wound with gauze, and placing the patient on systemic antimicrobials. However, no evidence exists that an adequate amount of drug reaches the wound site with this treatment. Indeed, there remains a need for compositions and methods for improved wound healing for administration to diabetic individuals.

Wound repair is a complex process involving the continual communication and interaction between fibroblasts, endothelial cells, keratinocytes, inflammatory cells and the extracellular matrix (ECM). Efficient wound repair requires adequate formation of granulation tissue to maintain a supply of nutrients in the wound area (Arbiser, J. Am. Acad. Dermatol., 34:486–497 [1996]; and Gallit and Clark, Curr. Op. Cell. Biol., 6:717–725 [1994]), and for extracellular matrix deposition (collagen synthesis). When collagen synthesis is impaired or inhibited, wounds heal slowly and incompletely (Streit et al., EMBO 19:3272–3282 [2000]; and Goodson and Hunt, J. Surg. Res., 22:221–227 [1997]). Thus, what is needed are means to facilitate wound healing, particularly in individuals with impaired and/or incomplete wound healing capabilities, such as diabetic individuals.

SUMMARY OF THE INVENTION

The present invention provides methods and compositions useful in localized transfer of genetic material or proteins. Moreover, the present invention provides methods and compositions for improving and/or controlling wound healing by applying a wound care device comprising HoxD3 and/or HoxA3 and/or HoxB3. In addition, the present invention provides methods and compositions for improved wound healing in subjects having impaired healing capabilities, such as diabetic subjects.

Thus, the present invention provides methods of treating a wound, comprising the step of applying a wound care device comprising HoxD3 DNA to a wound. Some embodiments comprise HoxD3 DNA as set forth in SEQ ID NO:1. In preferred embodiments, the applying is done under conditions such that wound healing is accelerated, under conditions such that wound closure is accelerated, under conditions such that angiogenesis in the wound is enhanced or under conditions such that type I collagen expression in the wound is enhanced. In some embodiments, the wound care device further comprises a cellulosic material.

The present invention also provides methods of treating a wound, comprising the step of applying a wound care device comprising HoxD3 protein to a wound. Some embodiments comprise HoxD3 protein as set forth in SEQ ID NO:2. In preferred embodiments, the applying is done under conditions such that wound healing is accelerated, under conditions such that wound closure is accelerated, under conditions such that angiogenesis in the wound is enhanced or under conditions such that type I collagen expression in the wound is enhanced. In some embodiments, the wound care device further comprises a cellulosic material.

In still further embodiments, the present invention provides methods of treating a wound having impaired healing capabilities, comprising the step of applying a wound care device comprising HoxD3 DNA to a wound. Some embodiments comprise HoxD3 DNA as set forth in SEQ ID NO:1. In preferred embodiments, the wound having impaired healing capabilities is a diabetic wound. In other preferred embodiments, the applying is done under conditions such that wound healing is accelerated, under conditions such that wound closure is accelerated, under conditions such that angiogenesis in the wound is enhanced, or under conditions such that type I collagen expression in the wound is enhanced. In some embodiments, the wound care device further comprises a cellulosic material.

The present invention also provides methods of treating a wound having impaired healing capabilities, comprising the step of applying a wound care device comprising HoxD3 protein to a wound. Some embodiments comprise HoxD3 protein as set forth in SEQ ID NO:2. In preferred embodiments, the wound having impaired healing capabilities is a diabetic wound. In preferred embodiments, the applying is done under conditions such that wound healing is accelerated, under conditions such that wound closure is accelerated, under conditions such that angiogenesis in the wound is enhanced or under conditions such that type I collagen expression in the wound is enhanced. In some embodiments, the wound care device further comprises a cellulosic material.

Also provided by the present invention are methods for gene transfer to a localized area, comprising the step of applying a cellulosic material comprising a plasmid encoding at least one protein of interest to a localized area. In some embodiments, cellulosic material comprises methylcellulose. In preferred embodiments, the localized area is a wound, while in particularly preferred embodiments, the wound is a diabetic wound. In some embodiments, the wound is an ulcer. In preferred embodiments, the protein of interest is a protein involved in wound healing. In some embodiments, the protein of interest is HoxD3, while in related embodiments, the protein of interest is HoxD3 as set forth in SEQ ID NO:2. In other embodiments, the plasmid comprises HoxD3 DNA as set forth in SEQ ID NO:1.

Moreover, the present invention provides methods of treating a wound, comprising the step of applying a wound care device comprising a HoxD10 inhibitor to a wound. In preferred embodiments, the applying is done under conditions such that wound healing is accelerated, under conditions such that wound closure is accelerated, under conditions such that angiogenesis in the wound is enhanced, or under conditions such that type I collagen expression in the wound is enhanced. In some embodiments, the wound care device further comprises a cellulosic material. In preferred embodiments, the HoxD10 inhibitor is selected from the group consisting of HoxD10 antisense molecules, HoxD10 dominant negative mutants, HoxD10 RNAi molecules, HoxD10-reactive antibodies, and HoxD10 artificial substrates.

The present invention also provides methods of treating a wound having impaired healing capabilities, comprising the step of applying a wound care device comprising a HoxD10 inhibitor to a wound. In preferred embodiments, the wound is a diabetic wound. In particularly preferred embodiments, the applying is done under conditions such that wound healing is accelerated, under conditions such that wound closure is accelerated, under conditions such that angiogenesis in the wound is enhanced or under conditions such that type I collagen expression in the wound is enhanced. In some embodiments, the wound care device further comprises a cellulosic material. In preferred embodiments, the HoxD10 inhibitor is selected from the group consisting of HoxD10 antisense molecules, HoxD10 dominant negative mutants, HoxD10 RNAi molecules, HoxD10-reactive antibodies, and HoxD10 artificial substrates.

Also provided by the present invention are compositions comprising a cellulosic material and a gene encoding at least one protein of interest. In some embodiments, the protein of interest is HoxD3 as set forth in SEQ ID NO:2. In some embodiments, the HoxD3 is a recombinant HoxD3 protein. In further embodiments, the recombinant HoxD3 protein is a fusion protein.

The present invention also provides compositions comprising a cellulosic material and at least one protein of interest. In some embodiments, the protein of interest is HoxD3 as set forth in SEQ ID NO:2. In some embodiments, the HoxD3 is a recombinant HoxD3 protein. In further embodiments, the recombinant HoxD3 protein is a fusion protein.

In some embodiments, the present invention provides compositions comprising a cellulosic material and an inhibitor of HoxD10, wherein the inhibitor is an inhibitor of HoxD10 DNA, an inhibitor of HoxD10 RNA, or an inhibitor of HoxD10 protein. In preferred embodiments, the inhibitor of HoxD10 is selected from the group consisting of HoxD10 antisense molecules, HoxD10 dominant negative mutants, HoxD10 RNAi molecules, HoxD10-reactive antibodies, and HoxD10 artificial substrates.

The present invention further provides compositions comprising cellulosic material and HoxA3 nucleic acid. In various embodiments, the HoxA3 nucleic acid comprises DNA or RNA, while the cellulosic material comprises methylcellulose. In preferred embodiments, the HoxA3 nucleic acid comprises a nucleic acid encoding a protein set forth in SEQ ID NO:15, a biologically active portion thereof or a biologically active variant thereof. In a subset of these embodiments, the HoxA3 nucleic acid comprises a nucleic acid set forth in SEQ ID NO:14. In particularly preferred embodiments, the HoxA3 nucleic acid is located in an expression vector. In various embodiments, the expression vector is selected from the group consisting of a plasmid vector, a recombinant viral vector and a recombinant bacterial vector. Also provided are embodiments in which the composition further comprises HoxD3 nucleic acid. In preferred embodiments, the HoxD3 nucleic acid comprises a nucleic acid encoding a protein set forth in SEQ ID NO:2, a biologically active portion thereof or a biologically active variant thereof. In various embodiments, the HoxD3 nucleic acid comprises a nucleic acid set forth in SEQ ID NO:1.

Also provided by the present invention are compositions comprising cellulosic material and HoxA3 protein. In various embodiments, the cellulosic material comprises methylcellulose. In preferred embodiments, the HoxA3 protein comprises a protein set forth in SEQ ID NO:15, a biologically active portion thereof or a biologically active variant thereof. In some embodiments, the HoxA3 protein is a recombinant HoxA3 protein. In a subset of these embodiments, the recombinant HoxA3 protein is a fusion protein comprising an affinity tag. Also provided are embodiments in which the composition further comprises HoxD3 protein. In preferred embodiments, the HoxD3 protein comprises a protein set forth in SEQ ID NO:2, a biologically active portion thereof or a biologically active variant thereof.

Moreover, the present invention provides methods comprising: providing; a subject with a wound, and a composition comprising HoxA3 nucleic acid or HoxA3 protein; and applying said composition to said wound. In various embodiments, the HoxA3 nucleic acid comprises DNA or RNA. In some preferred embodiments, the HoxA3 nucleic acid comprises a nucleic acid encoding a protein set forth in SEQ ID NO:15, a biologically active portion thereof or a biologically active variant thereof. In other preferred embodiments, the HoxA3 protein comprises a protein set forth in SEQ ID NO:15 or a biologically active portion thereof, a biologically active portion thereof or a biologically active variant thereof. Also provided are embodiments of the present invention in which the applying is under conditions such that wound healing is accelerated, the applying is under conditions such that wound closure is accelerated, the applying is under conditions such that angiogenesis in said wound is enhanced, and/or the applying is under conditions such that type I collagen expression in said wound is enhanced. In some embodiments, the composition further comprises a cellulosic material. In various embodiments, the cellulosic material comprises methylcellulose. In preferred embodiments, the composition is located in a wound care device. Also provided are embodiments in which the wound has impaired healing capabilities. In preferred embodiments, the wound having impaired healing capabilities is a diabetic wound. In some embodiments, the wound is an ulcer. Also provided are embodiments in which the composition further comprises HoxD3 nucleic acid or HoxD3 protein. In various embodiments, the HoxD3 nucleic acid comprises a nucleic acid encoding a protein set forth in SEQ ID NO:2, a biologically active portion thereof or a biologically active variant thereof. In other embodiments, the HoxD3 protein comprises a protein set forth in SEQ ID NO:2, a biologically active portion thereof or a biologically active variant thereof. In a subset of these embodiments, the HoxD3 nucleic acid comprises a nucleic acid set forth in SEQ ID NO:1.

The present invention provides compositions comprising cellulosic material and HoxB3 nucleic acid. In some embodiments, the HoxB3 nucleic acid comprises a nucleic acid encoding a protein set forth in SEQ ID NO:23, a biologically active portion thereof, or a biologically active variant thereof. In a subset of these embodiments, the HoxB3 nucleic acid comprises a nucleic acid set forth in SEQ ID NO:22. In some preferred embodiments, the HoxB3 nucleic acid is located in an expression vector. In additional embodiments, the composition further comprises one or both of HoxD3 nucleic acid and HoxA3 nucleic acid. In some embodiments, the HoxD3 nucleic acid comprises a nucleic acid encoding a protein set forth in SEQ ID NO:2, a biologically active portion thereof, or a biologically active variant thereof, and the HoxA3 nucleic acid comprises a nucleic acid encoding a protein set forth in SEQ ID NO:15, a biologically active portion thereof, or a biologically active variant thereof.

Furthermore, the present invention provides compositions comprising cellulosic material and HoxB3 protein. In some embodiments, the HoxB3 protein comprises a protein set forth in SEQ ID NO:23, a biologically active portion thereof, or a biologically active variant thereof. In some embodiments, the HoxB3 protein is a recombinant HoxB3 protein. In a subset of these embodiments, the recombinant HoxB3 protein is a fusion protein comprising an affinity tag. In additional embodiments, the composition further comprises one or both of HoxD3 protein and HoxA3 protein. In some preferred embodiments, the HoxD3 protein comprises a protein set forth in SEQ ID NO:2, a biologically active portion thereof, or a biologically active variant thereof, and the HoxA3 protein comprises a protein set forth in SEQ ID NO:15, a biologically active portion thereof, or a biologically active variant thereof.

The present invention also provides methods comprising: providing a subject with a wound, and a composition comprising HoxB3 nucleic acid or HoxB3 protein; and applying the composition to the wound. In some embodiments, the HoxB3 nucleic acid comprises a nucleic acid encoding a protein set forth in SEQ ID NO:23, a biologically active portion thereof or a biologically active variant thereof, while the HoxB3 protein comprises a protein set forth in SEQ ID NO:23, a biologically active portion thereof or a biologically active variant thereof. In some preferred embodiments, the applying is under conditions such that wound closure is accelerated, and/or the applying is under conditions such that angiogenesis in the wound is enhanced. In some preferred embodiments, the composition further comprises a cellulosic material. In preferred embodiments, the wound has impaired healing capabilities, and in a subset of these, the wound having impaired healing capabilities is a diabetic wound. Moreover, in some embodiments the composition further comprises one or both of HoxD3 nucleic acid and HoxA3 nucleic acid, or one or both of HoxD3 protein and HoxA3 protein.

DEFINITIONS

Figure 1:
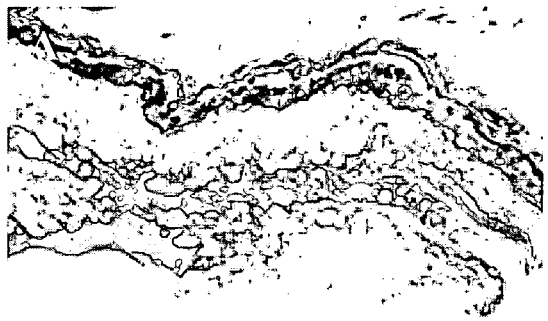
FIG. 1 provides photographs of trichrome-stained tissue sections showing collagen deposition in db/db wounds 14 days after creation of 1 cm open wounds. Panel A provides a low power image of a db/db wound treated with control DNA. As indicated in this Panel, there is limited collagen deposition (shown in blue). Panel B provides a higher power image of Panel A. Panel C provides a low power image of a HoxD3 DNA treated wound. As indicated in this Panel, there is more extensive collagen deposition in the HoxD3 DNA treated wound, as compared to the control. Panel D provides a higher power image of Panel C, showing extensive collagen deposition and the presence of small microvessels in the treated wound.
Figure 1:
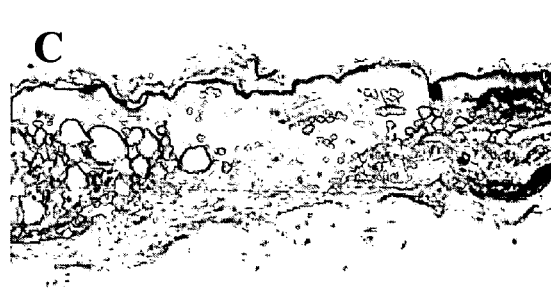
Figure 1:
Figure 1:
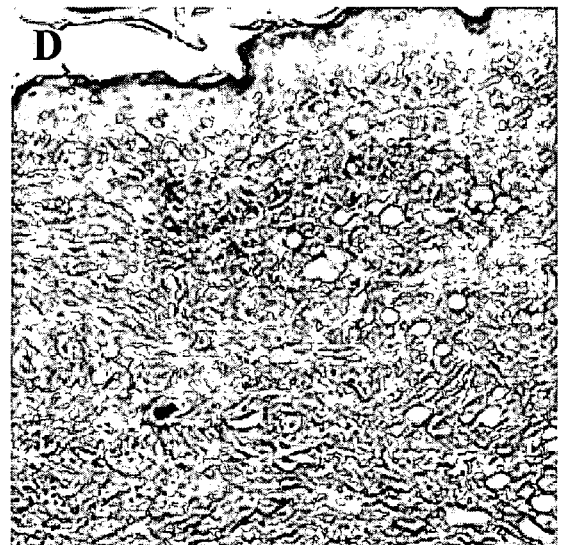

To facilitate an understanding of the present invention, a number of terms and phrases are defined below:

The term "gene" refers to a nucleic acid (e.g., DNA) sequence that comprises coding sequences necessary for the production of a polypeptide or precursor or RNA (e.g., tRNA, siRNA, rRNA, etc.). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends, such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

In particular, the term "HoxD3 gene" refers to the full-length HoxD3 nucleotide sequence. However, it is also intended that the term encompass fragments of the HoxD3 nucleotide sequence, as well as other domains (e.g., functional domains) within the full-length HoxD3 nucleotide sequence. Furthermore, the terms "HoxD3 gene," "HoxD3 nucleotide sequence," and "HoxD3 polynucleotide sequence" encompass DNA, cDNA, and RNA sequences.

The term "plasmid" as used herein, refers to a small, independently replicating, piece of DNA. Similarly, the term "naked plasmid" refers to plasmid DNA devoid of extraneous material typically used to affect transfection. As used herein, a "naked plasmid" refers to a plasmid substantially free of calcium-phosphate, DEAE-dextran, liposomes, and/or polyamines.

As used herein, the term "purified" refers to molecules (polynucleotides or polypeptides) that are removed from their natural environment, isolated or separated. "Substantially purified" molecules are at least 50% free, preferably at least 75% free, and more preferably at least 90% free from other components with which they are naturally associated.

The term "recombinant DNA" refers to a DNA molecule that is comprised of segments of DNA joined together by means of molecular biology techniques. Similarly, the term "recombinant protein" refers to a protein molecule that is expressed from recombinant DNA.

The term "fusion protein" as used herein refers to a protein formed by expression of a hybrid gene made by combining two gene sequences. Typically this is accomplished by cloning a cDNA into an expression vector in frame with an existing gene. The fusion partner may act as a reporter (e.g., βgal) or may provide a tool for isolation purposes (e.g., GST).

Suitable systems for production of recombinant proteins include but are not limited to prokaryotic (e.g., *Escherichia coli*), yeast (e.g., *Saccaromyces cerevisiae*), insect (e.g., baculovirus), mammalian (e.g., Chinese hamster ovary), plant (e.g., safflower), and cell-free systems (e.g., rabbit reticulocyte).

As used herein, the term "coding region" refers to the nucleotide sequences that encode the amino acid sequences found in the nascent polypeptide as a result of translation of an mRNA molecule. The coding region is bounded in eukaryotes, on the 5' side by the nucleotide triplet "ATG" that encodes the initiator methionine and on the 3' side by one of the three triplets which specify stop codons (i.e., TAA, TAG, and TGA).

Where amino acid sequence is recited herein to refer to an amino acid sequence of a naturally occurring protein molecule, "amino acid sequence" and like terms, such as "polypeptide" or "protein," are not meant to limit the amino acid sequence to the complete, native amino acid sequence associated with the recited protein molecule. The term "wild-type" refers to a gene or gene product that has the characteristics of that gene or gene product when isolated from a naturally occurring source. A wild type gene is that which is most frequently observed in a population and is thus arbitrarily designed the "normal" or "wild-type" form of the gene.

In contrast, the terms "modified," "mutant," and "variant" refer to a gene or gene product that displays modifications in sequence and or functional properties (i.e., altered characteristics) when compared to the wild-type gene or gene product. It is noted that naturally occurring mutants can be isolated; these are identified by the fact that they have altered characteristics when compared to the wild-type gene or gene product.

As used herein, the term "homeobox" refers to a conserved DNA sequence originally detected by DNA hybridization in many of the genes that give rise to homeotic and segmentation mutants in *Drosophila*. In particular, the homeobox consists of about 180 nucleotides coding for a sequence of about 60 amino acids, sometimes termed the homeodomain, which is involved in binding to DNA.

The terms "HoxD3," "Hox D3," "homeobox D3," "Hox4A," and "Hox-4.1," as used herein refer to a human homeobox gene (e.g., *Homo sapiens*—GenBank Accession No. D1117) and its gene product, as well as its vertebrate counterparts, including wild type and mutant products. The human HoxD3 coding region is set forth as SEQ ID NO:1, while the human HoxD3 protein sequence is set forth as SEQ ID NO:2. Moreover, the human HoxD3 cDNA sequence is set forth as SEQ ID NO:12, and the human HoxD3 gene is set forth as SEQ ID NO:13. Vertebrate counterparts of HoxD3 include mammalian HoxD3 (e.g., *Mus musculus*—GenBank Accession No. NM_010468), avian HoxD3 (e.g., *Gallus gallus*—GenBank Accession No. AF067959), reptilian HoxD3, amphibian HoxD3, piscean HoxD3, marsipobranchian HoxD3, and leptocardian HoxD3. Preferred embodiments of the present invention comprise mammalian HoxD3. HoxD3 variants, which differ from the wild type HoxD3 sequences in fewer than 1% of the residues, may also be suitable for use in the methods and compositions of the present invention.

As used herein, the terms "HoxA3," "Hox A3," "homeobox A3," "Hox1E" and "Hox-1.5-like" refer to a human homeobox gene (e.g., *Homo sapiens*—GenBank Accession No. AC004079) and its gene product, as well as its vertebrate counterparts, including wild type and mutant products. The human HoxA3 coding region is set forth as SEQ ID NO:14, while the human HoxA3 protein sequence is set forth as SEQ ID NO:15. Moreover, the human HoxA3 cDNA sequence is set forth in SEQ ID NO:16. Vertebrate counterparts of HoxA3 include mammalian HoxA3 (e.g., *Mus musculus*—GenBank Accession Nos. XM_13275), avian HoxA3, reptilian HoxA3, amphibian HoxA3, piscean HoxA3 (e.g., *Danio rerio*—GenBank Accession No. NM_131534; and *Heterodontus francisci*—GenBank Accession No. AF224262), marsipobranchian HoxA3, and leptocardian HoxA3. Preferred embodiments of the present invention comprise the "a isoform" of a mammalian HoxA3. HoxA3 variants, which differ from the wild type HoxA3 sequences in fewer than 1% of the residues, may also be suitable for use in the methods and compositions of the present invention. In particular, HoxA3 variants including but not limited to those of GenBank Accession Nos. NM_030661, NM_153631, and NM_153632, as well as non-naturally occurring variants generated by recombinant or other means (e.g. amino acid substitution, deletion, or addition) are contemplated to find use in the compositions and methods of the present invention.

As used herein, the terms "HoxB3," "Hox B3," "homeobox B3," "Hox2,""Hox2G," and "Hox-2.7," refer to a human homeobox gene (e.g., *Homo sapiens*—GenBank Accession No. NM_002146) and its gene product, as well as its vertebrate counterparts, including wild type and mutant products. The human HoxB3 coding region is set forth as SEQ ID NO:22, while the human HoxB3 protein sequence is set forth as SEQ ID NO:23. Moreover, the human HoxB3 cDNA sequence is set forth in SEQ ID NO:24. Vertebrate counterparts of HoxB3 include mammalian HoxB3 (e.g., *Mus musculus*—GenBank Accession No. NM_010458), avian HoxB3 (e.g., *Gallus gallus*—GenBank Accession No. X74506), reptilian HoxB3, amphibian HoxB3 (e.g., *Pleurodeles waltl*—AY383550), piscean HoxB3 (e.g., *Danio rerio*—GenBank Accession No. AJ537509), marsipobranchian HoxB3, and leptocardian HoxB3. HoxB3 variants that differ from the wild type HoxB3 sequences in fewer than 1% of the residues, may also be suitable for use in the methods and compositions of the present invention. In particular, naturally occurring HoxB3 variants, including but not limited to those of GenBank Accession No. NM_002146, as well as non-naturally occurring variants, generated by recombinant or other means (e.g. amino acid substitution, deletion, or addition) are contemplated to find use in the compositions and methods of the present invention.

The terms "HoxD10" and "Hox4D" refer to another human homeobox gene (GenBank Accession No. NM_002148) and its gene product, as well as its vertebrate counterparts. The human HoxD10 coding region is set forth as SEQ ID NO:9, while the human HoxD10 protein sequence is set forth as SEQ ID NO:10, and the human HoxD10 cDNA sequence is set forth as SEQ ID NO:11. Preferred embodiments of the present invention comprise mammalian HoxD10. HoxD10 variants, which differ from the wild type HoxD10 sequences in fewer than 1% of the residues, may also be suitable for use in the methods and compositions of the present invention.

As used herein, the term "HoxD10 inhibitor" refers to any molecule, which reduces the expression of or activity of HoxD10. HoxD10 inhibitors suitable for use in the methods and compositions of the present invention include but are not limited to antisense molecules, RNAi molecules, HoxD10-reactive antibodies, dominant negative mutants, and artificial substrates.

The term "antisense molecule" refers to polynucleotides and oligonucleotides capable of binding to an mRNA molecule. In particular, an antisense molecule is a DNA or RNA sequence complementary to an mRNA sequence of interest. In preferred embodiments, the term HoxD10 antisense molecule refers to a single-stranded DNA or RNA sequence that binds to at least a portion of a HoxD10 mRNA molecule to form a duplex which then blocks further transcription and/or translation.

As used herein, the terms "complementary" and "complementarity" refer to polynucleotides related by base-pairing rules. For example, for the sequence "5'-AGT-3'," the complementary sequence is "3'-TCA-5'."

The term "RNAi" refers to a double stranded RNA molecule, with each stand consisting of at least 20 nucleotides, which direct the sequence-specific degradation of mRNA through a process known as RNA interference. Thus RNAi can be used to block gene expression posttranscriptionally (Zamore et al., Cell 101: 25–33 [2000]).

The term "antibody" refers to polyclonal and monoclonal antibodies. Polyclonal antibodies which are formed in the animal as the result of an immunological reaction against a protein of interest or a fragment thereof, can then be readily isolated from the blood using well-known methods and purified by column chromatography, for example. Monoclonal antibodies can also be prepared using known methods (See, e.g., Winter and Milstein, Nature, 349, 293–299 [1991]). As used herein, the term "antibody" encompasses recombinantly prepared, and modified antibodies and antigen-binding fragments thereof, such as chimeric antibodies, humanized antibodies, multifunctional antibodies, bispecific or oligo-specific antibodies, single-stranded antibodies and F(ab) or F(ab)$_2$ fragments (See, e.g., EP-B1-0 368 684, U.S. Pat. No. 4,816,567, U.S. Pat. No. 4,816,397, WO 88/01649, WO 93/06213, WO 98/24884). The term "reactive" in used in reference to an antibody indicates that the antibody is capable of binding an antigen of interest. For example, a HoxD10-reactive antibody is an antibody, which binds to Hox10 or to a fragment of HoxD10.

The term "dominant negative mutant" refers to molecules that lack wild type activity, but which effectively compete with wild type molecules for substrates, receptors, etc., and thereby inhibit the activity of the wild type molecule. In preferred embodiments, the term "HoxD10 dominant negative mutant" refers to a HoxD10 mutant protein which competes with the wild type HoxD10 protein for DNA substrates, but which fails to induce downstream effects.

As used herein, the term "artificial substrate" refers to synthetic substance upon which a molecule of interest acts. In some embodiments, the term "HoxD10 artificial substrate" refers to molecules that bind HoxD10 to the exclusion of native HoxD10 substrates. Preferred "HoxD10 substrates" include but are not limited to DNA fragments to which HoxD10 binds. The term "DNA fragment" refers to pieces of DNA that are not part of the genome.

The term "portion" when used in reference to a nucleotide sequence refers to fragments of that sequence, which range in size from 10 nucleotides to the entire nucleotide sequence minus one nucleotide.

As used herein, the term "biologically active" refers to a molecule having structural, regulatory and or biochemical functions of a wild type homeobox molecule. In some instances, the biologically active molecule is a homolog of a mammalian homeobox molecule, while in other instance the biologically active molecule is a portion of a mammalian homeobox molecule. Other biologically active molecules, which find use in the compositions and methods of the present invention include but are not limited to mutant (e.g., variants with at least one deletion, insertion or substitution) mammalian homeobox molecules. Biological activity is determined for example, by restoration or introduction of Hox (e.g., HoxA3 or HoxD3) activity in cells which lack Hox activity, through transfection of the cells with a Hox expression vector containing a Hox gene, derivative thereof, or portion thereof. Methods useful for assessing HoxA3 activity include but are not limited to RT-PCR for induction of uPAR or MMP14 expression in transfected EC, assessment of angiogenesis of transfected EC grafted onto CAM, and migration of transfected EC in fibrin gels. Similarly, methods useful for assessing HoxD3 activity include but are not limited to Northern analysis or RT-PCR for induction of type I collagen or MMP-2 expression in transfected EC cells, and migration of transfected EC on fibrinogen surfaces.

The term "conservative substitution" as used herein refers to a change that takes place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17–21, 2nd ed, WH Freeman and Co. [1981]). Whether a change in the amino acid sequence of a peptide results in a functional homolog can be readily determined by assessing the ability of the variant peptide to function in a fashion similar to the wild-type protein. Peptides having more than one replacement can readily be tested in the same manner. In contrast, the term "nonconservative substitution" refers to a change in which an amino acid from one family is replaced with an amino acid from another family (e.g., replacement of a glycine with a tryptophan). Guidance in determining which amino acid residues can be substituted, inserted, or deleted without abolishing biological activity can be found using computer programs (e.g., LASERGENE software, DNASTAR Inc., Madison, Wis.).

The terms "mammals" and "mammalian" refer animals of the class mammalia, which nourish their young by fluid secreted from mammary glands of the mother, including human beings. The class "mammalian" includes placental animals, marsupial animals, and monotrematal animals.

Preferred embodiments of the present invention include but are not limited to a mammalian HoxD3 gene or gene product (e.g., mice, rats, pigs, monkeys, humans, etc.). In a particularly preferred embodiment of the present invention, the term "HoxD3 DNA" refers to the open reading frame or coding region of HoxD3 gene from *Homo sapiens* (SEQ ID NO:1), while the term "HoxD3 protein" refers to the amino acid sequence encoded by the HoxD3 DNA of *Homo sapiens* (SEQ ID NO:2).

As used herein the term "animal" refers to any member of the kingdom Animalia, which includes living things, which have cells differing from plant cells with regard to the absence of a cell wall and chlorophyll and the capacity for spontaneous movement. Preferred embodiments of the present invention are primarily directed to vertebrate (backbone or notochord) members of the animal kingdom.

The term "diabetic" as used here refers to organisms which have a disorder characterized by the insufficient production or utilization of insulin. Insulin is a pancreatic hormone that is needed to convert glucose for cellular metabolism and energy production. In preferred embodiments of the present invention, the term "diabetic patient" refers to patients suffering from diabetes mellitus. The term "diabetic" encompasses both patients with type I diabetes Ouvenile onset) and patients with type II diabetes (adult onset). "Type I diabetes" also referred to as "insulin-dependent diabetes" is a form of diabetes mellitus that usually develops during childhood or adolescence and is characterized by a severe deficiency in insulin secretion resulting from atrophy of the islets of Langerhans and causing hyperglycemia and a marked tendency towards ketoacidosis. "Type II diabetes" also referred to as "non-insulin-dependent diabetes" is a form of diabetes mellitus that develops especially in adults (most often in obese individuals) and that is characterized by hyperglycemia resulting from both insulin-resistance and an inability to produce more insulin.

The terms "patient" and "subject" refer to a mammal or an animal who is a candidate for receiving medical treatment.

As used herein, the term "wound" refers to a disruption of the normal continuity of structures caused by a physical (e.g., mechanical) force, a biological (e.g., thermic or actinic force, or a chemical means. In particular, the term "wound" encompasses wounds of the skin. The term "wound" also encompasses contused wounds, as well as incised, stab, lacerated, open, penetrating, puncture, abrasions, grazes, burns, frostbites, corrosions, wounds caused by ripping, scratching, pressure, and biting, and other types of wounds. In particular, the term encompasses ulcerations (i.e., ulcers), preferably ulcers of the skin.

As used herein, the term "wound healing" refers to a regenerative process with the induction of an exact temporal and spatial healing program comprising wound closure and the processes involved in wound closure. The term "wound healing" encompasses but is not limited to the processes of granulation, neovascularization, fibroblast, endothelial and epithelial cell migration, extracellular matrix deposition, re-epithelialization, and remodeling.

The term "wound closure" refers to the healing of a wound wherein sides of the wound are rejoined to form a continuous barrier (e.g., intact skin).

The term "granulation" refers to the process whereby small, red, grainlike prominences form on a raw surface (that of wounds or ulcers) as healing agents.

The term "neovascularization" refers to the new growth of blood vessels with the result that the oxygen and nutrient supply is improved. Similarly, the term "angiogenesis" refers to the vascularization process involving the development of new capillary blood vessels.

The term "cell migration" refers to the movement of cells (e.g., fibroblast, endothelial, epithelial, etc.) to the wound site.

The term "extracellular matrix deposition" refers to the secretion by cells of fibrous elements (e.g., collagen, elastin, reticulin), link proteins (e.g., fibronectin, laminin), and space filling molecules (e.g., glycosaminoglycans). As used herein, the term "type I collagen" refers to the most abundant collagen, which forms large well-organized fibrils having high tensile strength.

The term "re-epithelialization" refers to the reformation of epithelium over a denuded surface (e.g., wound).

The term "remodeling" refers to the replacement of and/or devascularization of granulation tissue.

The term "impaired healing capabilities" comprises wounds, which are characterized by a disturbed wound healing process. Examples of wounds with impaired healing capabilities are wounds of diabetic patients and alcoholics, wounds which are infected by microorganisms, ischemic wounds, wounds of patients suffering from deficient blood supply or venous stasis, and ulcers. Particularly preferred wounds are diabetic wounds.

The term "diabetic wounds" refers to wounds of mammals and humans suffering from diabetes. An example of a diabetic wound is an ulcer (e.g., *Ulcus cruris arteriosum* or *Necrobiosis lipoidica*).

As used herein, the term "ulcer" (i.e., "ulceration") refers to a local defect or excavation of the surface of an organ or tissue, produced by sloughing of necrotic tissue. The term encompasses various forms of ulcers (e.g., diabetic, neuropathic, arterial, decubitus, dental, perforating, phagedenic, rodent, trophic, tropical, varicose, venereal, etc.), although in preferred embodiments, surface (i.e., skin) ulcers are involved in the present invention. Especially preferred ulcers are diabetic ulcers.

The term "protein involved in wound healing" refers to any protein directly or indirectly involved in curing an injury to the body. For example, proteins involved in wound healing include but are not limited to HoxD3 protein, collagen, PDGF, VEGF, bFGF, and TGFβ.

In some embodiments, the present invention provides methods and compositions for "accelerating wound healing," whereby different aspects of the wound healing process are "enhanced." As used herein, the term "enhanced" indicates that the methods and compositions provide an increased wound healing rate. In preferred embodiments, the term "enhanced" indicates that the wound healing rate and/or a wound healing process occurs at least 10% faster than is observed in untreated or control-treated wounds. In particularly preferred embodiments, the term "enhanced" indicates that the wound healing rate and/or a wound healing process occurs at least 15% faster than is observed in untreated or control-treated wounds. In still further preferred embodiments, the term "enhanced" indicates that the wound healing rate and/or a wound healing process occurs at least 20% (e.g., 50%, 100%, . . . ) faster than wounds untreated or control-treated wounds.

The term "control" refers to subjects or samples which provide a basis for comparison for experimental subjects or samples. For instance, the use of control subjects or samples permits determinations to be made regarding the efficacy of experimental procedures. In some embodiments, the term "control subject" refers to animals, which receive a mock treatment (e.g., βgal plasmid DNA).

As used herein, the terms "gene transfer" and "transfer of genetic information" refer to the process of moving a gene or genes from one place to another. In preferred embodiments of the present invention, the term "gene transfer" refers to the transfer of a polynucleotide to cells and/or tissues of an animal to achieve a therapeutic effect. In some embodiments, the polynucleotide may be in the form of a plasmid, a gene fragment or an oligonucleotide. In some embodiments, "gene transfer" is temporary or transient, in other embodiments "gene transfer" is sustained, and in still further embodiments, the gene transfer is long-lived, permanent or stable.

As used herein, "gene transfer" may affect the transfection of cells and/or tissues. The term "transfection" refers to the introduction of foreign DNA into eukaryotic cells.

As used herein, the terms "localized" and "local" refer to the involvement of a limited area. Thus, in contrast to "systemic" treatment, in which the entire body is involved, usually through the vascular and/or lymph systems, localized treatment involves the treatment of a specific, limited area. Thus, in some embodiments, discrete wounds are treated locally using the methods and compositions of the present invention.

As used herein, the term "topically" means application to the surface of the skin, mucosa, viscera, etc. Similarly, the terms "topically active drug" and "topically active agent" refer to a substance or composition, which elicits a pharmacologic response at the site of application (e.g., skin), but is not necessarily an antimicrobial agent.

As used herein, the terms "systemically active drug" and "systemically active agent" are used broadly to indicate a substance or composition that will produce a pharmacologic response at a site remote from the point of application.

As used herein, the term "cellulosic material" refers to any composition that comprises cellulose or cellulose-like material. "Cellulose" $(C_6H_{10}O_5)_x$ refers to a polymer of glucose with over 3500 repeat units in a chain with β glycoside linkages. In preferred embodiments, the cellulose-like material of the present invention is methylcellulose. In a particularly preferred embodiment, the cellulose-like material is carboxymethylcellulose. However, any cellulosic material finds use with the present invention, as long as the material is suitable for immobilizing plasmid DNA at a desired site. In addition, the preferred cellulosic material of the present invention is sufficiently small in size to fit in wound sites as appropriate and has hydration-limiting properties.

As used herein, the term "medical devices" includes any material or device that is used on, in, or through a patient's body in the course of medical treatment for a disease or injury. Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like.

As used herein, "wound care devices" include, but are not limited to conventional materials such as dressings, plasters, compresses or gels containing the pharmaceuticals that can be used in accordance with the present invention. Thus, it is possible to administer the wound care devices comprising HoxD3 (and/or HoxA3) genes or proteins topically and locally in order to exert an immediate and direct effect on wound healing. The topical administration of wound care devices can be effected, for example, in the form of a solution, an emulsion, a cream, an ointment, a foam, an aerosol spray, a gel matrix, a sponge, drops or washings. Suitable additives or auxiliary substances are isotonic solutions, such as physiological sodium chloride solutions or sodium alginat, demineralized water, stabilizers, collagen containing substances such as Zyderm II or matrix-forming substances such as povidone. To generate a gel basis, formulations, such as aluminum hydroxide, polyacrylacid derivatives (e.g., Carbopol®), and cellulose derivatives (e.g., carboxymethyl cellulose) are suitable. These gels can be prepared as hydrogels on a water basis or as oleogels with low and high molecular weight paraffines or vaseline and/or yellow or white wax. As emulsifier alkali soaps, metal soaps, amine soaps or partial fatty acid esters of sorbitants can be used, whereas lipids can be added as vaseline, natural and synthetic waxes, fatty acids, mono-, di-, triglycerides, paraffin, natural oils (e.g., cocos oil), or synthetic fats (e.g., Miglyol®). The wound care devices comprising HoxD3 genes or proteins according to the invention can also, where appropriate, be administered topically and locally, in the region of the wound, in the form of liposome complexes or gold particle complexes. This form of administration is preferred for vectors which are applicable in gene therapy and which contain a nucleic acid, which can be used in accordance with the invention.

Furthermore, the treatment can be effected using a transdermal therapeutic system (TTS), which enables the pharmaceuticals of the present invention to be released in a temporally controlled manner. To improve the penetration of the administered drug through the membrane, additives such as ethanol, urea or propylene glycol can be added in addition to polymeric auxiliaries, such as Eudragit®. TTS have been disclosed, for example, in EP 0 944 398 A1, EP 0 916 336 A1, EP 0 889 723 A1 or EP 0 852 493 A1 (all of which are herein incorporated by reference).

The wound care devices comprising HoxD3 (and/or HoxA3) genes or proteins according to the invention can also encompass a cell (e.g., a keratinocyte) expressing a polypeptide of the invention, which is then secreted into the wound site. A suitable carrier for administering those modified cells would be a micro carrier consisting of biocompatible materials, such as, for example a dextran matrix (U.S. Pat. No. 5,980,888, herein incorporated by reference). However, a preferred embodiment of the invention encompasses the step of applying cellulosic material comprising a plasmid encoding at least one protein of interest to the wound (e.g., skin wound).

The terms "sample" and "specimen" in the present specification and claims are used in their broadest sense. On the one hand, they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid (CSF), semen, saliva, and wound exudates, as well as solid tissue. However, these examples are not to be construed as limiting the sample types applicable to the present invention.

DESCRIPTION OF THE INVENTION

The present invention provides methods and compositions useful in localized transfer of genetic material or proteins. Moreover, the present invention provides methods and compositions for improving and/or controlling wound healing by applying a wound care device comprising HoxD3 and/or HoxA3 and/or HoxB3. In addition, the present invention provides methods and compositions for improved wound healing in subjects having impaired healing capabilities, such as diabetic subjects.

I. Overview of Skin and External Wound Healing

Skin is a highly versatile organ that serves as a self-renewing and self-repairing interface between the vertebrate body and the environment. The skin covers the entire external surface of the body. In humans, this includes the external auditory meatus, the lateral aspect of the tympanic membrane, and the vestibule of the nose. The skin is continuous with, but distinct from, the mucosae of the alimentary, respiratory, and urogenital tracts, as specialized skin cells at the mucocutaneous junctions connects the skin and the mucosae. In addition to its protective functions, skin is capable of absorption, and excretion, and is also an important primary site of immunosurveillance against the entry of antigens and initiation of the primary immune response. Skin also performs many biochemical synthetic processes that have both local and systemic effects, and in this sense can be regarded as an endocrine organ.

There are two major types of skin—the thin, hairy (hirsute) skin (which covers most of the body), and thick, hairless (glabrous) skin (which forms the surfaces of the palms of the hands, soles of the feet, and flexor surfaces of the digits). Both types of skin are composed of three basic layers, namely, the epidermis, the dermis, and the hypodermis. The primary differences in the two types of skin are in thickness of their epidermal and dermal components, and in the presence of hairs with their attendant sebaceous glands and arrector pili muscles (pilobaceous units).

The epidermis, a stratified keratinous squamous epithelium primarily composed of keratinocytes, can be further divided into several strata (from deep to superficial), namely the stratum basale, stratum spinosum, stratum granulosum, stratum lucidum (where present), and stratum corneum. Epidermal appendages (e.g., pilosebaceous units, sudoriferous gland, and nails) are formed by ingrowth or other modification of the general epidermis, often referred to as the interfollicular epidermis. In addition to keratinocytes, the mature epidermis also contains various other cells, including melanocytes (i.e., pigment-forming cells), Langerhans cells (i.e., immunocompetent antigen-presenting cells derived form bone marrow), and lymphocytes. The epidermis also includes Merkel cells, which are thought to be modified keratinocytes.

The population of keratinocytes undergoes continuous renewal, with a mitotic layer of cells at the base of the epidermis replacing those shed at the surface. In order to maintain a constant thickness, the rate of cell production must equal the rate of cell loss. Thus, at any one time in the basal layer of the epidermis there are a variety of keratinocytes in different states of differentiation. These keratinocytes can be classified into three types according to their clonal proliferative capacity: 1) stem cells, which have extensive growth capacity; 2) differentiated paraclones, which have limited growth capacity; and 3) intermediate meroclones, which are thought to constitute long-lived progenitor cells (Trainer et al., 1997 Hum. Mol. Genet. 6:1761–7 [1997]; and Barrandon et al., Proc. Natl. Acad. Sci. USA 84:2302–6 [1987]).

When a wound occurs to the skin, the cells must work to close the breach and re-establish the barrier to the environment. The process of wound healing typically consists of three phases during which the injured tissue is repaired, regenerated, and new tissue is reorganized into a scar. These three phases can be classified as: a) an inflammation phase which begins from day 0 to 3 days; b) a cellular proliferation phase from 3 to 12 days; and c) a remodeling phase from 3 days to about 6 months.

In the inflammation phase, inflammatory cells, mostly neutrophils, enter the site of the wound followed by lymphocytes, monocytes, and later macrophages. Stimulated neutrophils release proteases and reactive oxygen species into the surrounding medium, with potential adverse effects on both the adjacent tissues and the invading microorganisms.

The proliferative phase consists of laying down new granulation tissue, and the formation of new blood vessels in the injured area. Fibroblasts, endothelial cells, and epithelial cells migrate in the wound site. These fibroblasts produce the collagen that is necessary for wound repair.

In re-epithelialization, epithelial cells migrate from the free edges of the tissue across the wound. This event is succeeded by the proliferation of epithelial cells at the periphery of the wound. In general, re-epithelialization is enhanced by the presence of occlusive wound dressings which maintain a moisture barrier.

Remodeling, the final phase of wound healing, is effected by both the replacement of granulation tissue with collagen and elastin fibers and the devascularization of the granulation tissue. Eventually, in most cases, a scar forms over the wounded area.

II. Gene Transfer and Wound Healing

The present invention provides generally applicable methods and compositions for improving and/or controlling wound healing, as well as the transfer of genetic material to a localized area. In some embodiments of the invention, at least one nucleic acid, which can be used in accordance with the invention is contained in an expression cassette in a vector, preferably in a vector which is applicable in gene therapy. The invention also comprises the use of a vector expressing a fusion protein useable according to the invention. The vector which is applicable in gene therapy preferably contains tissue-specific, wound-specific, skin-specific, cell cycle-specific, cell type-specific, metabolism-specific or constitutively active regulatory sequences which are functionally linked to the previously described nucleic acid.

The expression vectors used for preparing a polypeptide, which can be used in accordance with the invention, can be prokaryotic or eukaryotic. Examples of prokaryotic expression vectors are the pGEM vectors or pUC derivatives, which are used for expression in *E. coli*. Examples of eukaryotic expression vectors are the vectors p426Met25 and p426GAL1 (Mumberg et al., Nucl. Acids Res., 22, 5767–5768 [1994]), which are used for expression in *Saccharomyces cerevisiae*, the baculovirus vectors, as disclosed in EP-B1-0 127 839 or EP-B 1-0 549 721, which are used for expression in insect cells, and the vectors Rc/CMV, Rc/RSV, and SV40, which are used for expression in mammalian cells. These and additional suitable vectors are widely available.

In general, the expression vectors also contain promoters which are suitable for the respective host cell, such as the trp promoter for expression in *E. coli* (See, e.g., EP-BI-0 154 133), the Met 25, GAL 1 or ADH2 promoters for expression in yeast (Russel et al., J. Biol. Chem. 258, 2674–2682 [1983]; and Mumberg, supra), and the baculovirus polyhedrin promoter for expression in insect cells (See, e.g., EP-B 1-0 127 839). Promoters that permit constitutive, regulatable, tissue-specific, cell type-specific, cell cycle-specific or metabolism-specific expression in eukaryotic cells are suitable, for expression in mammalian cells. Regulatable elements in accordance with the present invention include but are not limited to promoters, activator sequences, enhancers, silencers and/or repressor sequences.

Examples of suitable regulatable elements which permit constitutive expression in eukaryotes are promoters which are recognized by RNA polymerase III or viral promoters or enhancers such as the CMV enhancer, CMV promoter (See, e.g., Example 6 and 7), SV40 promoter, LTR promoters (e.g., MMTV-derived as described by Lee et al., Nature 214, 228–232 [1981]), and other viral promoter and activator sequences which are derived from, for example, HBV, HCV, HSV, HPV, EBV, HTLV or HIV. Conversely, examples of regulatable elements that permit inducible expression in eukaryotes are the tetracycline operator in combination with an appropriate repressor (Gossen et al., Curr. Opin. Biotechnol. 5, 516–20 [1994]).

The expression of nucleic acids that can be used in accordance with the present invention preferably takes place under the control of tissue-specific promoters, with skin-specific promoters, such as the human K10 promoter (Bailleul et al., Cell 62: 697–708 [1990]), the human K14 promoter (Vassar et al., Proc. Natl. Acad. Sci. USA 86: 1563–67 [1989]) or the bovine cytokeratin IV promoter (Fuchs et al., The Biology of Wool and Hair (eds. Rogers et al.) Chapman and Hall, London/N.Y., pp. 287–309 [1988]) being particularly preferred. Other examples of regulatable elements that permit tissue-specific expression in eukaryotes are promoters or activator sequences from promoters or enhancers of genes, which encode proteins that are only expressed in particular cell types.

Additionally, examples of regulatable elements that permit cell cycle-specific expression in eukaryotes are promoters of the following genes: cdc25A, cyclin A, cyclin E, cdc2, E2F, B-myb and DHFR (Zwicker and Müller, Trends Genet. 13, 3–6 [1997]). Examples of regulatable elements that permit metabolism-specific expression in eukaryotes are promoters that are regulated by hypoxia, by glucose deficiency, by phosphate concentration or by heat shock. An example of a regulatable element which permits keratinocyte-specific expression in skin is the FiRE element (Jaakkola et al., Gen. Ther., 7: 1640–1647 [2000]). The FiRE element is an AP-1-driven, FGF-inducible response element of the syndecan-1 gene (Jaakkola et al., FASEB J., 12: 959–9 [1998]). Examples for regulatable elements that allow spatial and temporal expression are nucleic acids coding for a fusion between the site-specific recombinase Cre and a modified estrogen receptor. The expression of this fusion protein is controlled by a tissue-specific promoter. The resulting cytoplasmic fusion protein can translocate into the nucleus upon administration of the estrogen analogue tamoxifen and induce recombination (Feil et al., Proc Natl Acad Sci 93: 10887–90 [1996]).

In order to permit the nucleic acids which can be used in accordance with the present invention to be introduced into a eukaryotic or prokaryotic cell by means of transfection, transformation or infection, and thereby enabling the polypeptide to be expressed, the nucleic acid can be present as part of a plasmid, or as a part of a viral or non-viral vector. Particularly suitable viral vectors in this context are: baculoviruses, vaccinia viruses, adenoviruses, adeno-associated viruses and herpesviruses. Particularly suitable non-viral vectors in this context are: liposomes, virosomes, cationic lipids and polylysine-conjugated DNA. Examples of viral vectors that are applicable in gene therapy include but are not limited to adenoviral vectors or retroviral vectors (Lindemann et al., Mol. Med. 3: 466–76 [1997]; Springer et al., Mol. Cell. 2: 549–58 [1998]).

Eukaryotic expression vectors are suitable for use in gene therapy when present in isolated form, since naked DNA can penetrate into skin cells when applied topically (Hengge et al., J. Clin. Invest. 97: 2911–6 [1996]; and Yu et al., J. Invest. Dermatol. 112: 370–5 [1999]). Vectors which are applicable in gene therapy can also be obtained by complexing the nucleic acid which can be used in accordance with the present invention with liposomes, since this makes it possible to achieve a very high efficiency of transfection, particularly of skin cells (Alexander and Akhurst, Hum. Mol. Genet. 4: 2279–85 [1995]).

In lipofection, small, unilamellar vesicles consisting of cationic lipids are prepared by subjecting the liposome suspension to ultrasonication. The DNA is bound ionically on the surface of the liposomes, specifically in a relationship, which is such that a positive net charge remains and 100% of the plasmid DNA is complexed by the liposomes. In addition to the DOTMA (1,2-dioleoyloxypropyl-3-trimethylammonium bromide) and DPOE (dioleoylphosphatidylethanolamine) lipid mixtures originally utilized for this purpose (Felgner et al., Proc Natl Acad Sci U S A. 84:7413–7 [1987]), a large number of new lipid formulations have by now been synthesized and tested for their efficiency in the transfection of various cell lines (Behr et al., Proc. Natl. Acad. Sci. USA 86, 6982–6986 [1989]; Felgner et al., (1994) J. Biol. Chem. 269, 2550–2561 [1994]; Gao and Huang, Biochim. Biophys. Acta 1189, 195–203 [1991]). Examples of the new lipid formulations are DOTAP N-[1-(2,3-dioleoyloxy)propyl]-N,N,N-trimethylammonium ethyl sulfate or DOGS (TRANSFECTAM; dioctadecylamido-glycylspermine). The Cytofectin GS 2888 cationic lipids have also proved to be very well suited for transfecting keratinocytes in vitro and in vivo (U.S. Pat. No. 5,777,153; and Lewis et al., Proc. Natl. Acad. Sci. USA, 93: 3176–3181 [1996]). Auxiliary substances which increase the transfer of nucleic acids into the cell can, for example, comprise proteins or peptides which are bound to DNA or synthetic peptide-DNA molecules which make it possible to transport the nucleic acid into the nucleus of the cell (Schwartz et al., Gene Therapy 6, 282 [1999]; and Brandén et al., Nature Biotech. 17, 784 [1999]). Auxiliary substances also encompass molecules which enable nucleic acids to be released into the cytoplasm of the cell (Planck et al., J. Biol. Chem. 269, 12918 [1994]; Kichler et al., Bioconj. Chem. 8, 213 [1997]).

Liposomes are a pharmaceutically acceptable carrier within the meaning of the present invention. Liposomes comprise multilamellar vesicles (MLVs), small unilamellar vesicles (SUVs) and large unilamellar vesicles (LUVs). Methods for preparing liposome-nucleic acid complexes are known to the skilled person (e.g., Straubinger et al., Methods of Immunology, 101: 512–527 [1983]; and Szoka et al., Proc. Natl. Acad. Sci. USA, 75: 4194–4198 [1978]). The term "liposomes" encompasses, for example, liposomal compositions which are disclosed in U.S. Pat. No. 5,422,120, WO 95/13796, WO 94/23697, WO 91/14445 and EP 524,968 B1. Liposomes can be used with nucleic acids according to the present invention, as well as for polypeptides according to the present invention or for both as a pharmaceutical carrier. Preferably liposomes are used as pharmaceutical carriers for the nucleic acids of the present invention. A therapeutically active substance can also be conjugated to the liposome or it can be conjugated to a hydrogel polymer, wherein the hydrogel polymer (or a component of the hydrogel polymer) is conjugated to a liposome or can be enclosed by a liposome. Another especially suitable form vector can be obtained by applying the nucleic acid usable according to the invention to gold particles and applying these topically with the aid of the so called "gene gun" by shooting them into the skin or cells (See, e.g., Wang et al., J. Invest. Dermatol., 112: 775–81 [1999], and Tuting et al., J. Invest. Dermatol., 111: 183–8 [1998]). Devices for performing intradermal injection using pressure have also been disclosed (See, e.g., U.S. Pat. No. 5,630,796).

For the use of the previously described nucleic acid in gene therapy it is also advantageous if the part of the nucleic acid which encodes the polypeptide contains one or more non-coding sequences, including intron sequences, preferably between the promoter and the start codon for the polypeptide and/or a polyA sequence, in particular the naturally occurring polyA sequence or an SV40 virus polyA sequence at the 3' end of the gene since this thereby makes it possible to stabilize the mRNA (Jackson, Cell 74, 9–14 [1993]; and Palmiter et al., Proc. Natl. Acad. Sci. USA 88, 478–482 [1991]).

However, in some particular preferred embodiments, the present invention provides methods and compositions involving the use of cellulosic materials and plasmid DNA to transfer genetic material to a localized site of interest. In particularly preferred embodiments, methylcellulose pellets or films are used as a supporting matrix for plasmid DNA to be transferred to cells surrounding the pellet. In some embodiments, the methylcellulose has limited hydration capabilities, which allows the plasmid DNA to be released from the matrix in a controlled manner over time and prevents the wound area from becoming overly wet. In other embodiments, alternative matrix materials are used. However, preferred matrices all have the ability to immobilize the plasmid DNA to a localized area and allow the release of the DNA from the matrix to the cells over time. Indeed, during the development of the present invention surgical sponges were tested for their suitability for the transfer of genetic information, as were naked plasmid DNA constructs (e.g., without any supporting matrix). As indicated in Example 9, these experiments were unsuccessful. Although an understanding of the mechanism is not necessary in order to use the present invention, it is believed that the use of surgical sponges resulted in a treatment site that was too hydrated, leading to a more rapid release of the plasmid DNA from the matrix and decreasing the contact of the plasmid DNA with the cells at the treatment site. For naked DNA, it is believed that the conditions at the wound site were sufficiently hostile, such that the plasmids were not efficiently taken-up by the cells. Thus, a matrix such as a cellulosic composition (e.g., methylcellulose) is preferred in treatment of localized areas as the genetic material is efficiently taken up by the cells, resulting in the expression of the gene of interest. In a particularly preferred embodiment, the cellulosic material is carboxymethylcellulose.

In the compositions and methods exemplified herein, pellets containing various concentrations of plasmid DNA were used. For example, in some experiments, 25 μg of plasmid DNA were used, while in other experiments, 50 μg of plasmid DNA were used. In preferred embodiments, pellets containing 25 μg of plasmid DNA are prepared and then used either alone (i.e., one pellet per wound or area to be treated) or in multiples (i.e., two or more pellets per wound or area to be treated). The number of pellets used is dependent upon the size of the wound or area to be treated, and upon the stage of wound healing and the desired results. For example, a larger number of pellets may be applied at the onset of treatment, some or all of which are then replaced as treatment continues, with a lesser or greater number of pellets as needed. The plasmid DNA contained in these pellets may be the same or different, and may be at the same or different concentration levels. For example, when detectable plasmid DNA levels have decreased (typically, at about 4 days the plasmid DNA is no longer detectable), "fresh" pellets may be applied to the treatment area as needed. In other embodiments, when the detectable protein levels have decreased (typically at about 7 days the protein expressed by the gene is no longer detectable), "fresh" pellets may be applied to the area as needed.

Any plasmid DNA of interest finds use in the methods and compositions of the present invention. Indeed, various plasmid constructs were used during the development of the present invention, including DNA with reporter (or "signal") capabilities, as well as DNA that encodes proteins associated with wound healing, and other functions. The dose of plasmid DNA can be administered on an as-needed basis. Typically, the dose is approximately 1 μg DNA per $cm^2$ to be treated. However, dose response curves are generated as known in the art on an as needed and/or desired basis, in order to determine the optimum plasmid concentration for use in any particular situation.

The present invention finds use in a number of settings. As exemplified herein, one particularly preferred embodiment involves the use of the present invention to improve wound healing in subjects with impaired natural healing capabilities, such as diabetic subjects. Nonetheless, the present invention finds use in controlling the rate of wound healing (e.g., by modifying the dose of plasmid DNA). Indeed, the present invention finds use in delaying or prolonging wound healing, as well as in accelerating and/or improving wound healing. For example, delaying wound healing is desirable in subjects that tend to experience more fibrosis than observed in most subjects. Thus, the present invention provides means to control the rate of wound healing to maximize the therapeutic benefit for individual patients.

The present invention also finds use in transfer of genetic information corresponding to one or more genes. Thus, in some settings, one gene product is produced by the subject's cells after the transfer of genetic material from the composition of the present invention, while in other settings multiple gene products are produced by the subject's cells. For example, in one embodiment, the gene for HoxA3 is used in conjunction with the gene for HoxD3. As these genes have different functions and effects, the combination maximizes wound healing in suitable cases. In alternative settings, the subject is treated with multiple genes in series. In this case, one gene is used for a suitable length of time and then another gene is used for another suitable length of time (e.g., HoxD3 DNA is used first, followed by HoxA3 DNA and/or a gene encoding an anti-fibrotic). In particularly preferred embodiments the subject is treated with one or more of HoxD3 DNA, HoxA3 DNA, and HoxB3 DNA. Thus, the present invention provides maximum flexibility in the treatment regimen and facilitates optimization of treatment for each subject on an individualized (i.e., case-by-case) basis.

In addition to improving wound healing on external surfaces such as the skin and mucous membranes, the present invention finds use in improving the healing of internal lesions. For example, the present invention finds use in improving wound healing associated with surgical incisions and other localized injury to internal tissues.

Furthermore, the present invention finds use in settings such as inhibition of angiogenesis in tumors. For example, in some embodiments, inhibitory genes are provided that inhibit or prevent blood vessel formation. The compositions of the present invention are placed near or within the tumor area, which results in the release of the genetic information encoding the inhibitory factor and the subsequent expression of the genetic information by the cells in the area. Thus, the tumor development is inhibited or stopped due to the lack of vascularization.

III. Protein Transfer and Wound Healing

The present invention also provides methods and compositions for improving and/or controlling wound healing via transfer of a protein or proteins to a localized area. Indeed, in some embodiments, the present invention provides methods and compositions involving the use of cellulosic materials and at least one recombinant protein to transfer at least one biologically active protein to a localized site of interest. In particularly preferred embodiments, methylcellulose pellets and/or films are used as a supporting matrix for the transfer of protein to cells surrounding the pellet. In some preferred embodiments, the methylcellulose has limited hydration capabilities, which allows the protein to be released from the matrix in a controlled manner over time and prevents the wound area from becoming overly wet. In other embodiments, alternative matrix materials are used. However, preferred matrices have the ability to immobilize the protein to a localized area and to allow the release of the protein from the matrix to the cells over time. It is not intended, however, that application of the protein be limited to cellulosic materials.

Alternatively, the above-described proteins that can be used in the present invention, are produced as fusion proteins, constituting a functional variant of one of the previously described proteins or a functional variant only after the fusion moiety has been eliminated. These fusion proteins include, in particular, fusion proteins that have a content of about 1–300 foreign amino acids, preferably about 1–200 foreign amino acids, particularly preferably about 1–150 foreign amino acids, more preferably about 1–100 foreign amino acids, and most preferably about 1–50 foreign amino acids. Such foreign amino acid sequences may be prokaryotic peptide sequences that can be derived, for example, from *E. Coli* β-galactosidase. Other preferred examples of peptide sequences for fusion proteins are peptides that facilitate detection of the fusion protein; they include but are not limited to green fluorescent protein or variants thereof. It is also possible to add on at least one "affinity tag" or "protein tag" for the purpose of purifying the previously described proteins. For example, suitable affinity tags enable the fusion protein to be absorbed with high specificity and selectivity to a matrix. This attachment step is then followed by stringent washing with suitable buffers without eluting the fusion protein to any significant extent, and specific elution of the absorbed fusion protein. Examples of the protein tags which are known to the skilled person include but are not limited to a $(His)_6$ tag, a Myc tag, a FLAG tag, a hemagglutinin tag, a glutathione-S-transferase (GST) tag, a tag consisting of a an intein flanked by an affinity chitin-binding domain, and a maltose-binding protein (MBP) tag. These protein tags can be located N-terminally, C-terminally and/or internally.

The proteins that can be used in the methods and compositions of the present invention can also be prepared synthetically. Thus, the entire polypeptide, or parts thereof, can, for example, be produced by classical synthesis techniques (e.g., Merrifield technique). Particular preference is given to using polypeptides which have been prepared recombinantly using one of the previously described nucleic acids. Furthermore, proteins of the present invention can be isolated from an organism or from tissue or cells for use in accordance with the present invention. Thus, it is possible, for example, to purify proteins, which can be used in the present invention, from human serum (e.g., Abdullah et al., Arch. Biochem. Biophys., 225:306–312 [1983]). Furthermore, it is possible to prepare cell lines expressing the proteins of the present invention. These cell lines can then be used for isolating the proteins of interest.

In the compositions and methods exemplified herein, pellets containing various quantities of the protein of interest are contemplated. Anywhere from 1 nanogram to 100 micrograms of the protein of interest are incorporated into the methylcellulose pellets of the present invention. One or multiple pellets are used to treat wounds. The number of pellets used is dependent upon the size of the wound or area to be treated and on the stage of wound healing or desired results. For example, a larger number of pellets may be applied at the onset of treatment, some or all of which are then replaced as treatment continues, with a lesser or greater number of pellets as needed. The protein of interest contained in these pellets may be the same or a different protein, and may be at the same or different concentration levels.

The present invention finds use in a number of settings. As exemplified herein, one particularly preferred embodiment involves the use of the present invention to improve wound healing in subjects with impaired healing capabilities, such as diabetic subjects. Nonetheless, the present invention finds use in controlling the rate of wound healing (e.g., by modifying the dose of recombinant protein). Indeed, the present invention finds use in delaying or prolonging wound healing, as well as in accelerating and/or improving wound healing. For example, delaying wound healing is desirable in subjects that tend to experience more fibrosis than is typical. Thus, the present invention provides means to control the rate of wound healing to maximize the therapeutic benefit for individual patients.

Various proteins of interest find use in the methods and compositions of the present invention. Thus, the present invention finds use in transfer of one or more proteins. For example, in one embodiment, recombinant HoxA3 protein is used in conjunction with recombinant HoxD3 protein. As these proteins have different functions and effects, the combination maximizes wound healing in suitable cases. In alternative settings, the subject is treated with multiple proteins in series. In this case, one protein is used for a suitable length of time and then another protein is used for another suitable length of time (e.g., HoxD3 protein is used first, followed by HoxA3 protein and/or a protein with anti-fibrotic activity). In particularly preferred embodiments the subject is treated with one or more of HoxD3 protein, HoxA3 protein, and HoxB3 protein. Thus, the present invention provides maximum flexibility in the treatment regimen and facilitates optimization of treatment for each subject on an individualized (i.e., case-by-case) basis.

In addition to improving wound healing on external surfaces such as the skin and mucous membranes, the present invention finds use in improving the healing of internal lesions. For example, the present invention finds use in improving wound healing associated with surgical incisions and other localized injury to internal tissues.

Furthermore, the present invention finds use in settings such as inhibition of angiogenesis in tumors. For example, in some embodiments, inhibitory proteins are provided that suppress or prevent blood vessel formation. The compositions of the present invention are placed near or within the tumor area, which results in the release of the inhibitory protein to cells in the area. Thus, the tumor development is inhibited or stopped due to the lack of vascularization.

IV. Impaired Healing in Diabetics and Wound Healing with HoxD3

Homeobox (Hox) genes are master transcription factors that are associated with morphogenesis and organogenesis during development and more recently, in adult tissue remodeling (Myers et al., J. Cell. Biol., 148:343–352 [2000]; Boudreau et al., J. Cell. Biol., 139:257–264 [1997]; Boudreau et al., Curr. Op. Cell Biol., 10:640–646 [1998]; van Oostveen et al., Leukemia 13:1675–1690 [1999]; and Cillo et al., Exp. Cell Res., 248:1–9 [1999]). Specifically, HoxD3 was shown to be involved in the specification of the first and second vertebrae as knock out animals display homeotic transformations in the atlas region (Condie et al., Development 119: 579–595 [1993]). It is thought that the depletion of these structures is due to a failure of proliferation of precursor cells responsible for generating these structures. A function of HoxD3 in cell proliferation was also confirmed by the overexpression of HoxD3 in A549 cells, which resulted in the expression of metastasis-associated genes (Omatu et al., Hokkaido Igaku Zasshi 74:367–76, 1999). Moreover, HoxD3 was also found to promote endothelial cell (EC) migration by regulating expression of integrin $\alpha v \beta 3$ and the urokinase plasminogen activator, (uPA) serine proteinase (Boudreau et al. [1997] supra). This change in adhesive properties mediates the EC conversion from a resting to an invasive state. Again the HoxD3 induced change in adhesion properties also stimulates tumor progression as retroviral overexpression of HoxD3 in the chick chorioallantoic membrane assay resulted in the formation of endotheliomas and vascular malformation (Boudreau et al., [1997] supra).

Previous work described the expression of a number of Hox genes in the skin mainly during fetal wound healing (Stelnicki et al., J. Invest. Dermatol., 110:110–115 [1998]; Stelnicki et al., J. Invest. Dermatol., 111: 57–63 [1998]; and Reigeretal., J. Invest. Dermatol., 103:341–346 [1994]). It was noted that many Hox genes, including HoxA4 (HoxD3), HoxA5, HoxA7 and HoxB7, are abundantly expressed in basal keratinocyte layer cells and spread throughout the epidermis during development, suggesting again a role in the regulation of cellular proliferation/adhesion in the developing fetal skin. Interestingly, in the adult human skin, expression of Hox genes is significantly down-regulated after birth and is restricted to the upper epidermal keratinocyte layers and is not present in the dermis (Stelnicki et al., J. Invest. Dermatol., 110: 110–115 [1998]). Further investigation of Hox expression in fetal wounds, which heal without scarring, revealed that PRX-2 and HoxB13 genes were strongly upregulated in fetal, as compared to adult wounds (Stelnicki et al., J. Invest. Dermatol., 111: 57–63 [1998]). However, these studies did not address the expression of Hox genes in the vasculature, nor was re-expression of other Hox genes in adult wound healing investigated.

Thus the present invention, discloses for the first time a direct role for the Hox genes in wound-induced expression of Hox genes, particularly HoxD3. In addition, the present invention discloses for the first time the expression of Hox B3 and HoxD3 genes in adult skin. Moreover, the present invention discloses for the first time, expression of Hox genes in the skin in a cell type other than keratinocytes. In particular, Hox genes were found to be expressed in vascular endothelial cells within the dermis.

The expression of HoxB3 and HoxD3 was evaluated by in situ hybridization in non-diabetic mouse (both wild-type and non-diabetic littermates) skin samples taken at 1, 4, 7, and 14 days post-wounding. In control unwounded skin samples, relatively weak staining of HoxB3 was observed in the epidermis and hair follicles. In addition, HoxB3 was abundantly expressed in vascular endothelial cells lining many medium sized and smaller vessels of arteriole and venous origin. Four days following wounding, granulation tissue had begun to form and keratinocytes in the epidermis and cells in the hair follicles showed intense staining for HoxB3. It was then noted that expression of HoxB3 persisted in the EC of many of the medium and small size vessels. Although HoxB3 expression was also observed in newly forming capillaries in the granulation tissue, expression was somewhat reduced as compared to pre-existing vessels.

By seven days after wounding, keratinocytes and cells in the hair follicle at the wound continued to show strong expression of HoxB3. Many inflammatory cells and fibroblasts were also observed near the wound site, which also showed strong expression of HoxB3. The EC of capillaries within the wound also maintained expression of HoxB3. However, again, expression was relatively weak compared to pre-existing capillaries and larger arterioles further away from the wound site.

By 14 days after wounding, expression of HoxB3 remained high in keratinocytes, hair follicle epithelium and fibroblasts near the wound. Although many small vessels could not be detected in the wound at this time, significant expression of HoxB3 in EC of capillaries near the repairing wound site was observed.

Thus, specific changes in Hox gene expression in endothelial cells during wound repair in normal and healing-impaired mice were observed. Detailed analysis revealed expression of HoxD3 and HoxB3 in activated endothelial cells in normal wound repair as shown by in situ hybridization (See, Example 2). Surprisingly, wound-induced expression of HoxD3 was found to be markedly lower and delayed in onset in healing-impaired diabetic animals (See, Example 12). Moreover, the expression of HoxD3 was also reduced in ulcers from diabetic patients (See, Example 14), as compared to the HoxD3 expression levels observed during normal wound healing (See, Example 13). Surprisingly, these experiments revealed a down-regulation of HoxD3 selectively in wounds having impaired healing capabilities, such as diabetic wounds as compared to normally healing wounds. Thus, it is contemplated that HoxD3 is essential for normal wound healing. Moreover, a similar pattern and magnitude of expression of HoxB3 in wild-type and genetically diabetic mice was observed. This indicates that impaired wound healing is not likely related to insufficient levels of HoxB3, but rather is selectively due to reduced expression of HoxD3.

The ability of HoxD3 to influence expression of type I collagen mRNA was examined during development of the present invention. Human microvascular endothelial cells were stably transfected with cDNA plasmids expressing either HoxD3 or HoxB3 or control empty vectors. Northern blot analysis for the Col1A1 mRNA was performed, and showed that endothelial cells transfected with HoxD3, but not HoxB3 or control plasmid, contained levels of Col1A1 mRNA that were 2.5 to 3-fold higher than HoxB3-transfected or control transfected cells respectively (See, Example 5). Thus, HoxD3 is capable of selectively inducing expression of type I collagen in EC.

As HoxD3 is selectively down-regulated in wounds having impaired healing capacities, such as diabetic wounds, wounded diabetic mice were treated with methylcellulose pellets containing HoxD3 plasmid, to determine whether gene transfer of HoxD3 accelerates healing in the diabetic animals. Indeed, the results indicated that restoration of HoxD3 in diabetic wounds improves overall wound healing (See, Example 7, and FIGS. 2 and 3).

In particular, in the experiments described below, diabetic mice were used to assess the improvement of wound healing associated with restored expression of HoxD3. In these experiments, diabetic mice (C57BL/KsJ-db/db) received full thickness wounds (2.5 cm diameter). Methylcellulose pellets containing 25 µg HoxD3 plasmid were applied to the open wounds of one group and another group received CMV βgal (control; "control DNA"). Wounds were measured weekly until closure. The tissues were then processed for Northern blotting and histology. Preliminary results indicated that diabetic control wounds closed in 66 days (on average), while the HoxD3 treated wounds closed in 52 days (on average). The percent difference in wound closure was significant ($p<0.05$) at days 7, 14, 21, 28, 35, 42, and 49.

The effect of HoxD3 on 0.8 cm wounds created bilaterally on diabetic (db/db) mice was also investigated. Wound biopsies were taken on days 7, 10, 14 and 17. In preliminary studies, it was found that by 17 days, five out of six HoxD3-treated wounds and only one out of six control-treated wounds had closed. Based on Northern blot analysis, addition of HoxD3 plasmid to diabetic wounds was found to significantly increase mRNA levels of collagen at 3, 7, and 10 days post-wounding.

Moreover, the existence of a link between HoxD3 expression and type I collagen level was examined in diabetic animals. Surprisingly, it was found that diabetic mice displayed reduced levels of collagen, which could be increased upon administration of HoxD3 (See Example 7 and FIG. 4). In addition, HoxD3 was also found to increase angiogenesis during the wound healing process of diabetic mice (See Example 3, FIG. 5).

The finding that HoxD3 treatment of wounds was beneficial was unexpected given that HoxD3 is not observed to be expressed in adult human skin, and because of the earlier documented relationship between increased HoxD3 expression and tumorigenesis (Myers et al., J. Cell Biol., 148:343–351 [2000]). In particular, increased HoxD3 expression has been shown to promote the development of hemangioma-like structures, which are aberrant structures typically observed as part of benign tumors. Taken together, these results lead away from a therapeutic use of HoxD3. Thus, the surprising finding of reduced expression of HoxD3 in wounds having impaired healing capacities, such as diabetic wounds, offered the unexpected possibility of using a cancer-associated protein for therapeutic purposes.

As discussed above, a deficiency in HoxD3 expression results in markedly reduced type I collagen production in the healing-impaired wounds of diabetic animals. However, the methods and compositions provided by the present invention restore HoxD3 expression in diabetic wounds, leading to enhanced type 1 collagen expression, and improved overall wound healing. Specifically, the present invention provides methods and compositions for the more rapid healing of wounds by increasing HoxD3 expression in vascular endothelial cells and fibroblasts following wounding.

Interestingly, homeobox proteins have the ability to enter into cells in the absence of endocytosis and have the ability to exit cells in the absence of a signal sequence (See, Prochiantz, Curr Opin Cell Biol 12:400–406 [2000]). Once inside the cell, Hox proteins gain access to the nucleus whereby they regulate gene transcription. Proteins with these features are termed translocating proteins or messenger proteins. Residues in the third alpha helix of Hox proteins are required for internalisation (Le Roux et al., Proc. Natl. Acad. Sci. USA, 88:1864–1868 [1991]; and Derossi et al., J. Biol. Chem., 269:10444–10450 [1994]). Thus, the methods and compositions disclosed herein differ substantially from the prior art, as they do not require additional components (e.g., viruses) for distribution of a transcription factor such as HoxD3 protein to the nuclei of cells within a wound. The unexpected use of transcription factors in wound healing therapy offers the possibility of a completely new type of therapy. Previously, the only proteins used to improve diabetic wound repair were soluble secreted growth factors (e.g., PDGF, bFGF, etc.), which triggered several signalling pathways and multiple downstream effects. In contrast, the HoxD3 protein of the present invention is a nuclear transcription factor, and as such is a signalling cascade end point. Thus, the methods and compositions of the present invention comprising HoxD3, are contemplated to provide a more precise therapeutic tool. In sum, by increasing levels of HoxD3 in wounds having impaired healing capabilities (e.g., diabetic wounds), through the administration of genetic information or protein, the present invention provides the means to promote angiogenesis and collagen synthesis in wounds having impaired healing capacities.

V. HoxA3 and Wound Healing

The Hox genes in group 3, HoxA3, HoxB3, and HoxD3, exhibit nearly identical expression patters and possess approximately 50% identity in protein coding sequences. Nonetheless targeted inactivation studies have demonstrated that HoxA3 and HoxD3 have unique functions in vivo. Specifically, mice lacking HoxA3 die after birth with deficiencies in pharyngeal tissues derived from the mesenchymal neural crest (Chisaka and Capecchi, Nature, 350:473–479 [1991]), while mice lacking HoxD3 survive despite having malformations in the somitic, mesodermally-derived tissues of the axial skeleton (Condie and Capecchi, Dev. Biol., 119:579–595 [1993]). The uniqueness of the single mutant phenotypes suggested that HoxA3 and HoxD3 have qualitatively different functions. However, the observation that vertebral defects in HoxD3 mutant mice were exacerbated by removing HoxA3 function, suggested that there is also a functional overlap between these genes and thus, a quantitative aspect to their combined activities (Condie and Capecchi, [1993] supra; and Manley and Capecchi, Dev. Biol., 195:1–15 [1998]).

In fact, during embryogenesis HoxD3 and HoxA3 were shown to be functionally interchangeable if expressed within the proper context. Specifically, when HoxD3 was expressed from the HoxA3 locus of HoxA3 null mice, HoxD3 was capable of rescuing the otherwise lethal HoxA3 null phenotype (Greer et al., Nature, 403:661–664 [2000], herein incorporated by reference). However, it was not clear whether these two Hox genes would also be equivalent in adult tissues. Studies of compound mutants of Hox9 genes revealed markedly different effects on embryonic and adult mammary gland development indicating that Hox genes may perform multiple roles that change with time (Chen and Capecchi, Proc. Natl. Acad. Sci., 96:541–546 [1999]).

With this in mind, the influence of HoxA3 in adult microvascular endothelial cells was examined during the development of the present invention. As described in more detail below in Examples 15–23, HoxA3 has been shown for the first time to promote EC migration in culture and angiogenesis in vivo. The present studies also indicate that in EC, the HoxA3 gene may cooperate with the paralogous HoxD3 gene to promote EC migration. In particular, HoxD3 was shown to induce expression of the latent MMP-2 pro-enzyme, while HoxA3 induces expression of MMP-14.

MMP-14 not only activates latent MMP-2, but can also directly function as a potent matrix degrading enzyme (See, Werb, Cell, 91:439–442 [1997]). In addition, HoxA3 upregulates expression of uPAR, the receptor for uPA, whose expression is induced by HoxD3 (Boudreau et al., J. Cell Biol., 139:257–264 [1997]). Thus, during development of the present invention, HoxA3 and HoxD3 have been shown to mediate expression of distinct, yet functionally related genes, which can act in a cooperative manner to promote EC migration. Nonetheless, an understanding of the mechanism(s) is not necessary in order to make and use the present invention.

Several reports have emphasized additional interactions between uPAR, integrins and MMPs. For instance, uPAR can directly ligate the $\alpha v \beta 3$ integrin to enhance cell-cell interactions (Tarui et al., J. Biol. Chem., 276:3983–90 [2000]). The $\alpha v \beta 3$ integrin can also bind and localize active MMP-14 and MMP-2 on invading cells (Brooks et al., Cell, 92:391–400 [1998]; and Hofiann et al., Int. J. Cancer, 87:12–19 [2000]), while MMP-14 is able to modify the $\beta 3$ integrin subunit resulting in its activation and enhanced ability to bind MMP-2 (Deryugina et al., Int. J. Cancer, 86:15–23 [2000]). Thus, when the paralogous HoxA3 and HoxD3 genes or gene products are applied together to a wound, they are expected to act synergistically to induce an angiogenic phenotype in EC. Nonetheless, an understanding of the mechanism(s) is not necessary in order to make and use the present invention.

It is also worth noting however, that HoxA3 infrequently generates hemangioma-like lesions. Recent studies investigating components of the plasminogen/plasminogen activator system elegantly demonstrated the need for tight regulation of proteolysis in order for newly formed vessels to stabilize and mature (Bajou et al., J. Cell Biol., 152:777–784 [2001]). Since HoxA3 targets uPAR and MMP-14, and can act to localize and regulate serine or metallo-proteinase activity in endothelial cells, HoxA3 is contemplated to prevent diffuse proteolysis, which if left unchecked, could lead to the formation of irregular and cavernous cystic structures characteristic of hemangiomas (Werb, Cell, 91:439–442 [1997]); Ossowski and Aguire-Ghiso, Curr. Opin. Cell Biol., 12:613–620 [2000]; Montesano et al., Cell, 62:435–445 [1990]; and Takahashi et al., J. Clin. Invest., 93:2357–2364 [1994]). Nonetheless, an understanding of the mechanism(s) is not necessary in order to make and use the present invention.

Figure 9:
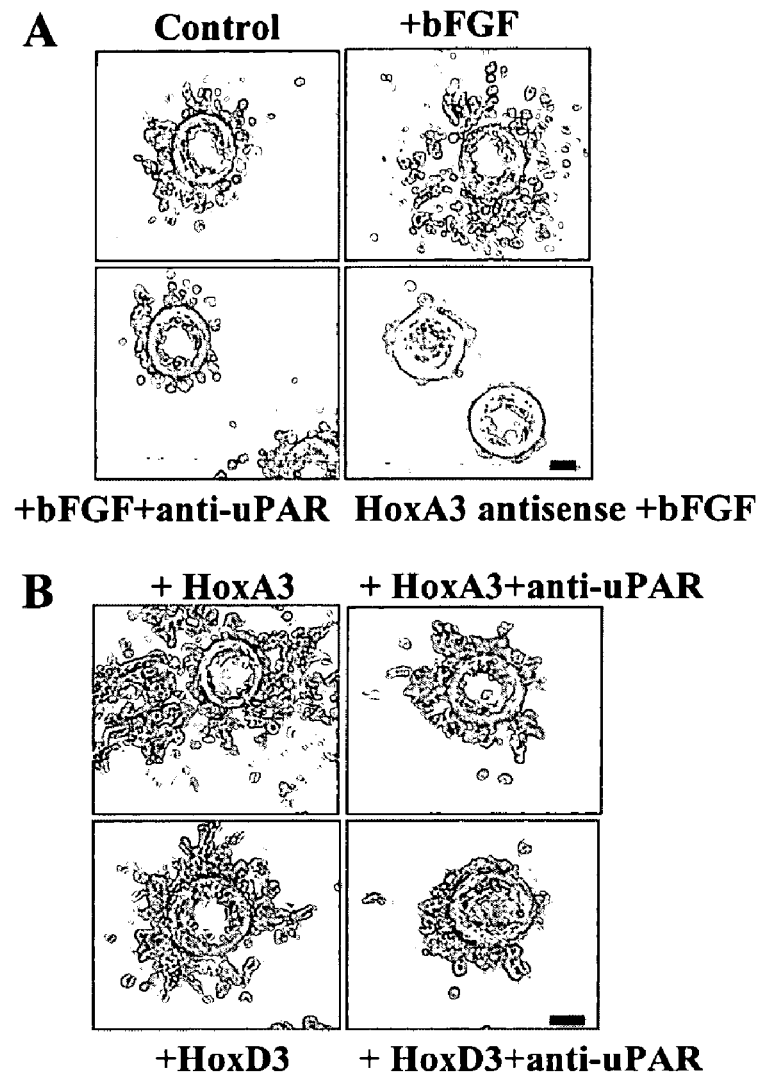
FIG. 9 indicates that HoxA3 promotes EC migration in fibrin. The photomicrographs in panels A and B show the degree of migration observed for each condition, 72 hours following embedding into three-dimensional fibrin gels (Bar=10 µM). Panel C shows the extent of migration of control, HoxA3 and HoxD3-transfected HMEC-1 cells after 5 hours in modified Boyden chambers coated with 20 mg/ml fibrinogen. Data are expressed as the mean+/−standard deviation (n=3), and ** denotes statistical significance p<0.05.
Figure 9:
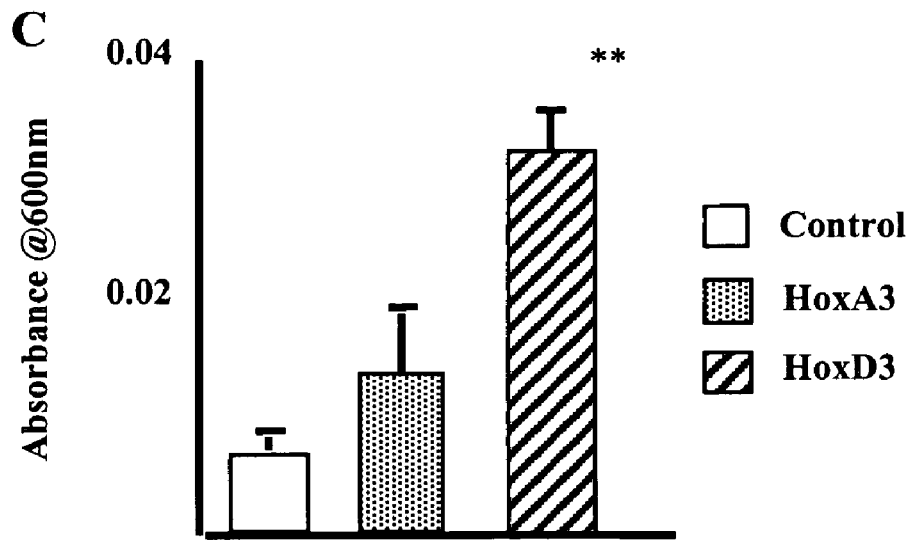

Differences in EC behaviour induced by HoxA3 and HoxD3 were also apparent in tissue culture studies disclosed herein. As shown in FIG. 9, HoxA3-transfected EC possess a greater ability to migrate into three-dimensional fibrin gels, whereas HoxD3-transfected EC possess a greater ability to migrate on fibrinogen. The findings that HoxA3-induced migration was impaired in the presence of function blocking antibodies against uPAR are consistent with previous reports which demonstrated that while migration into a pure fibrin matrix was not effected by antibodies against $\alpha v \beta 3$, antibodies against uPAR could abolish invasion (Kroon et al., Am. J. Pathol., 154:1731–1742 [1999]). Thus, some embodiments of the present invention comprise both HoxA3 and uPAR function blocking antibodies when it is desirable to utilize some but not all of the HoxA3-induced functions. Furthermore, although the MMP system may also function to mediate migration in fibrin-rich matrices in the absence of the plasminogen activator system (Hiroaka et al., Cell, 95:365–377 [1998]), addition of the MMP inhibitor GM6001 had no impact on HoxA3-depdendent migration the fibrin system described herein. Nonetheless, an understanding of the mechanism(s) is not necessary in order to make and use the present invention.

VI. Selection of Compounds Capable of Modulating HoxA3 Activity

The present invention also provides novel tools and techniques for identifying compounds capable of enhancing or inhibiting various HoxA3 activities associated with wound repair. For instance, the ability of a candidate compound to modulate HoxA3-induced angiogenesis can be assessed by observing blood vessel formation in CAM grafted with control tumors or HoxA3-transfected tumors, in the presence and absence of the candidate compound. Alternatively, the ability of a candidate compound to modulate the HoxA3-induced expression of uPAR or MMP14 can be assessed by comparing uPAR or MMP14 expression levels in control epithelial cells and in HoxA3-transfectants, in the presence and absence of the candidate compound. In addition, the ability of a candidate compound to modulate HoxA3-induced migration of epithelial cells through fibrin or on fibrinogen can be assessed by observing the migration of control epithelial cells and HoxA3-transfectants, in the presence and absence of the candidate compound. Moreover, the ability of a candidate compound to modulate HoxA3-induced migration of keratinocytes on plastic can be assessed by observing the migration of control keratinocytes and HoxA3-transfectants, in the presence and absence of the candidate compound.

The inventors contemplate many other means of screening compounds. The examples provided above are presented merely to illustrate a range of techniques available. One of ordinary skill in the art will appreciate that many other screening methods can be used successfully.

VII. HoxB3 and Wound Healing

Figure 14:
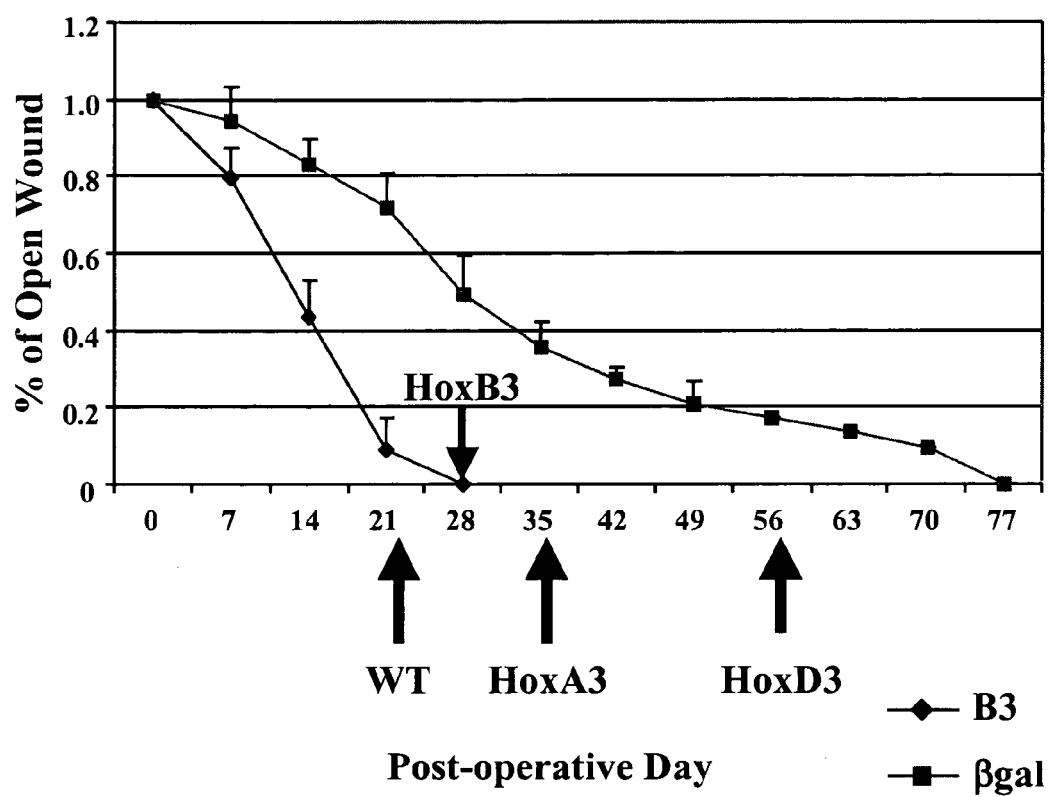
FIG. 14 provides a graph demonstrating that HoxB3 treatment enhances the wound closure rate in diabetic mice. Squares represent the diameter of control-treated (βgal DNA) wounds over time, whereas the diamonds represent the diameter of HoxB3-treated (HoxB3 expression vector) wounds over time. Also shown are the wound closure times of wild type mice, as well as diabetic mice treated with HoxD3, and HoxA3.

As shown herein for the first time, treatment of diabetic wounds with HoxB3 DNA alone significantly enhanced the rate of wound closure, as compared to control DNA-treated diabetic wounds (See, FIG. 14). This finding was unexpected given that the HoxB3 expression level observed in diabetic wounds was on the order of that observed in the wounds of non-diabetic subjects. This was also surprising given that transfection of human microvascular endothelial cells with HoxB3 did not result in an increase in type I collagen expression. Thus, although HoxB3, HoxA3 and HoxD3 apparently play distinct roles in the process of wound healing, all are effective as therapeutic agents for the treatment of diabetic wounds. Furthermore, it is contemplated that wound care devices comprising two or more of HoxB3, HoxA3 and HoxD3 provide even more potent treatments.

VIII. Selection of Compounds Capable of Modulating HoxB3 Activity

The present invention also provides novel methods and compositions for identifying compounds that enhance or inhibit various HoxB3 activities associated with wound repair. For instance, the ability of a candidate compound to modulate HoxB3-enhanced wound closure can be assessed by observing the closure of HoxB3 protein or DNA-treated 2.5 cm wounds on the backs of diabetic (db/db) mice, in the presence and absence of the candidate compound. Alternatively, the ability of a candidate compound to modulate the HoxB3-induced capillary morphogenesis can be assessed by observing capillary morphogenesis of HoxB3-tranfected HMEC-1 cells cultured on reconstituted basement membrane, in the presence and absence of a candidate compound. In addition, the ability of a candidate compound to modulate the HoxB3-induced expression of Ephrin A1 can be assessed by comparing Ephrin A1 expression levels in control epithelial cells and in HoxB3-transfectants, in the presence and absence of the candidate compound. The present invention provides many other means of screening compounds. The examples provided above are presented merely to illustrate a range of techniques available. One of ordinary skill in the art will appreciate that many other screening methods can be used successfully.

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); mM (millimolar); μM (micromolar); N (Normal); mol (moles); mmol (millimoles); μmol (micromoles); nmol (nanomoles); g (grams); mg (milligrams); μg (micrograms); ng (nanograms); 1 or L (liters); ml (milliliters); μl (microliters); cc (cubic centimeters); cm (centimeters); mm (millimeters); μm (micrometers); run (nanometers); ° C. (degrees Centigrade); bp (base pair); kb (kilobase); PCR (polymerase chain reaction); CMV (cytomegalovirus); βgal (beta-galactosidase); cpm (counts per minute); BrdU (bromodeoxyuridine); SDS (sodium dodecyl sulfate); $MgCl_2$ (magnesium chloride); NaCl (sodium chloride); EDTA (ethylene diamine tetraacetic acid); DEPC (diethyl pyrocarbonate); SSC (salt sodium citrate); BSA (bovine serum albumin); FCS (fetal calf serum); PBS (phosphate buffered saline); Tris (tris (hydroxymethyl)aminomethane); $H_2O$ (water); IgG (immunoglobulin); Clonetics (Palo Alto Calif.); Invitrogen (Invitrogen Life Technologies, Carlsbad, Calif.); Roche (F. Hoffmann-La Roche Limited, Basel, Switerland); Sigma (Sigma Chemical Co., St. Louis, Mo.); Jackson (Jackson Laboratory, Bar Harbor, Me.); Boehringer Mannheim (Boehringer Mannheim, Indianapolis, Ind.); Fisher (Fisher Scientific, Pittsburgh, Pa.); Ambion (Ambion, Austin, Tex.); Vector (Vector Laboratories, Burlingame, Calif.); Zymed (Zymed Laboratories, South San Francisco, Calif.); Pharmingen (Pharmingen, San Diego, Calif.); Qiagen (Qiagen, Valencia, Calif.); Life Technologies (Life Technologies, Rockville, Md.); Alpha Innotec (Alpha Innotec, San Leandro, Calif.); and ATCC (American Type Culture Collection, Manassus, Va.).

In some experiments, genetically diabetic C57BL/KsJ-db/db mice, their non-diabetic litter mates, and wild-type C57B1/129 mice obtained from Jackson were used. The animals were housed in the University of California, San Francisco animal care facility, and all procedures were approved by the Committee on Animal Research. All mice were between 8 to 12 weeks at time of wounding.

In preferred embodiments and in the experiments described below, the methylcellulose used is carboxymethylcellulose (sodium salt) (Sigma #C-5013). Water soluble polymer and 1% solution at 25° C. has a viscosity of 1500–3000 cps. To prepare the methylcellulose pellets containing plasmid DNA, 25 μg of plasmid DNA (in a volume of 25 μl of water) was mixed with 25 μl of a 1% solution of methylcellulose (dissolved in sterile water). After brief mixing, 50 μl of this solution was dropped in a bacterial culture plate without spreading, and allowed to dry for 1–2 hours at room temperature. The methylcellulose film formed a spot approximately 1 cm in diameter, which is then peeled off the culture dish and placed directly onto the recently made open wound or other site to be tested. For example, in experiments involving 0.8 cm wounds, one 50 μl pellet was used, while for 2.5 cm wounds, four or five of the 50 μl pellets were placed adjacent to or in the wound. In other embodiments, HoxD3 protein is used in conjunction with the pellets, while in other embodiments, a retroviral vector is used for gene delivery to a target site of interest.

EXAMPLE 1

Wounding

Prior to wounding, wild-type and diabetic mice were anaesthetized with 0.04 cc of ketamine/xylazine (50 mg/cc/ 2.5 mg/cc). The dorsa of the mice were shaved and a 1.5 cm linear incision was made through the *panniculus camosus* and closed with two interrupted 4-0 nylon sutures (e.g., placed 0.5 cm apart). The mice were sacrificed at post wound days 1, 4, 7, and 14, by anaesthetic overdose and bilateral thoracotomies were performed. To ensure consistent sampling of the wounds, a standard 0.5×0.5 cm section from the center of the wound was obtained and processed for RNA, in situ hybridization, and/or immunohistochemistry. A total of 16 wild-type mice (5 mice at day 0; 3 at days 1, 4, and 7 post-wounding; and 2 at day 14 following wounding) were used and 12 diabetic (db/db) mice (3 mice each at days 0, 4, 7, and 14 days post-wounding) were used in the analyses described herein.

EXAMPLE 2

In Situ Hybridization

Since diabetic mice have been reported to show a delay in wound repair and angiogenesis, the expression of both HoxB3 and HoxD3 after production of a linear wound in diabetic mice was investigated. In these experiments, in situ hybridization for HoxB3 or HoxD3 was performed on a minimum of 8 sections (for each Hox gene) from each of the wounded tissues collected (See, Example 1). Wound tissues were fixed in 10% formalin/phosphate buffer overnight at room temperature. Tissues were then dehydrated in ethanol and paraffin embedded. Then, 5 μm sections were place on Vectabond (Vector)-treated slides. Prior to use, the slides were heated at 80° C. for 30 minutes, deparaffinized in xylene, and rehydrated in a graded ethanol series, as known in the art. Tissues were post-fixed in 4% paraformaldehyde for 5 minutes at room temperature. Tissue sections were then treated with RNAse-free proteinase K (Ambion) at 20 μg/mL in 10 mM Tris pH 7.5 and 1 mM EDTA, for 10 minutes at 37° C. Sections were again post-fixed with 4% paraformaldehyde for 5 minutes at room temperature, washed and dehydrated through a graded ethanol series, as known in the art.

Tissue sections were prehybridized in 50% formamide, 3 mM NaCl, 10 mM Tris pH 7.5, 1 M EDTA, 1% blocking reagent (Boehringer Mannheim), 10% dextran sulfate, and 150 mg/ml tRNA for 1 hour at 45° C. The tissues were then hybridized with digoxigenin-labeled riboprobes for HoxB3 or HoxD3, in either the sense or anti-sense orientation. These riboprobes were generated using linearized plasmids and the Genius RNA Labeling kit (Boehringer Mannheim) as known in the art (See, Myers et al., supra; and Boudreau et al. [1997], supra). The riboprobes were diluted in hybridization solution to a concentration of 800 ng/ml, and incubated with tissue sections overnight at 45° C. Following hybridization, the slides were washed with 2×SSPE for 5 minutes at room temperature then 0.2×SSPE for 1 hour at 50° C. Tissue sections were blocked in 2% blocking reagent (Boehringer Mannheim), 100 mM Tris pH 7.5, and 150 mM NaCl, for 45 minutes at room temperature. Sections were then washed with 1% BSA, 0.3% Triton-X100, 100 mM Tris pH 7.5, and 150 mM NaCl, and incubated overnight with a 1:500 dilution of anti-digoxigenin alkaline-phosphatase conjugated antibody (Boehringer Mannheim). The tissue sections were subsequently incubated in 20 μl/ml nitroblue tetrazolium/5-bromo-4-chloro-3-indoyl phosphate substrate (Boehringer Mannheim) until they reached the desired intensity. The reaction was stopped in Tris/EDTA, pH 8, and sections were counterstained with 1% Fast Green and mounted with an aqueous mounting compound known as Crystal Mount (Fisher).

Thus, HoxB3 and HoxD3 expression in linear wounds of wild-type animals were examined. As with HoxB3, expression of HoxD3 was observed in both keratinocytes and hair follicle epithelial cells in unwounded skin. However, in contrast to HoxB3, no significant levels of expression of HoxD3 were observed in the resting EC of small vessels in the sub-dermal layer or in capillaries within the dermal layer. However, occasional low levels of expression were observed in some small arterioles.

Nonetheless, within 1 day after wounding, an increase in intensity of HoxD3 expression in keratinocytes, hair follicle epithelium, fibroblasts, and notably, small and medium sized vessels adjacent to the wound site was observed. Furthermore, an increase in expression in HoxD3 in capillaries immediately adjacent to the wound site was observed, although there was no increase in HoxD3 expression in capillaries further away. The increase in expression of HoxD3 in fibroblasts and EC of vessels near the wound site was maintained at 4 days after wounding. Indeed, high levels of HoxD3 expression were maintained in EC of capillaries in the wound tissue through 7 days after wounding. However, by 14 days post-wounding, expression of HoxD3 in EC had begun to decline.

No difference in intensity or localization in either HoxD3 or HoxB3 expression was observed in unwounded skin of diabetic mice, as compared to unwounded skin of wild-type mice. Furthermore, although a decrease in the extent of new capillaries formed and vessel density was noted in diabetic mice following wounding, no significant changes in intensity or localization of HoxB3 expression in these vessels adjacent or away from the wounds was observed for up to 14 days after wounding.

Expression of HoxD3 in wounded wild-type and diabetic (db/db) mice was also examined. Expression of HoxD3 was observed at four days following wounding and capillaries near the wounds in diabetic mice expressed relatively low levels of HoxD3 as compared to wild-type animals. In addition, expression in control and diabetic (db/db) mice at 7 days following wounding was analyzed. Although both tissues showed similar levels of HoxD3 expression in the epidermis, expression of HoxD3 was markedly reduced in EC of vessels near or within the wounds of diabetic (db/db) mice as compared to wild-type animals. Finally, although the EC of capillaries and fibroblasts within the wounds of wild-type mice express HoxD3, capillary EC in wounds of diabetic (db/db) animals showed little HoxD3.

EXAMPLE 3

Immunohistochemistry

For immunohistochemistry, 5 μm sections embedded in paraffin were deparaffinized in 3 washes of Hemo-De (Fisher) for 5 minutes. Sections were then rehydrated through a graded ethanol series. Tissue sections were then treated with 1 μg/μL of protease K for 10 minutes at 37° C. and then washed under running water for 10 minutes. Sections were blocked for endogenous peroxidase activity with Peroxoblock (Zymed) for 45 seconds at room temperature. Sections were then incubated in 1% goat serum/PBS for 15 minutes at room temperature. Sections were then incubated with 1:250 dilution of rat-anti-mouse CD31 (PE-CAM) antibody (Pharmingen) overnight at 4° C. Sections were incubated with a 1:500 dilution of biotin-conjugated goat anti-rat IgG (Jackson Laboratories) for 1 hour at room temperature and then incubated for 1 hour at room temperature with the Vectastain ABC Reagent (Vector). Slides were developed using the DAB plus kit (Zymed). Sections were dehydrated through ethanol and mounted with Permount.

The production of type I collagen has been shown to be decreased in other diabetic wound models (Darby et al., Intl. J. Biochem. Cell Biol., 29:191–200 [1997]; and Bitar and Labbad, J. Surg. Res., 61:113–119 [1996]). To confirm that linear wounds in db/db diabetic mice, which exhibit reduced HoxD3, also show a reduction in type I collagen deposition and expression, the following experiments were conducted. Paraffin-embedded sections of wild-type or diabetic mouse skin were taken 7 and 14 days after wounding. Trichrome staining showed that collagen deposition was indeed reduced in diabetic mice as compared to wild-type mice.

Figure 5:
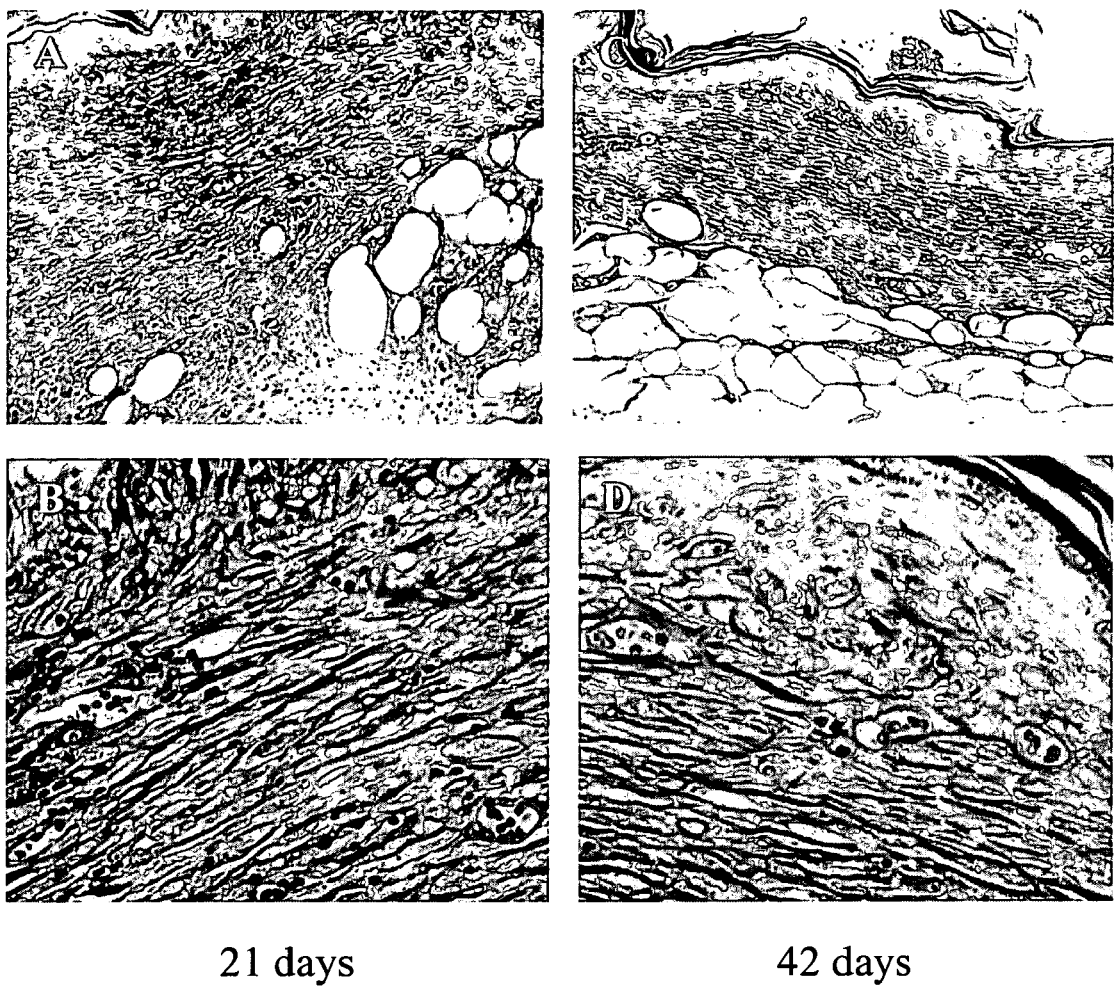
FIG. 5 provides photographs of trichrome-stained tissue sections showing collagen deposition (in blue) in db/db wounds 21 and 42 days after creation of 0.8 cm open wounds. Panel A depicts a healing wound 21 days following application of HoxD3 DNA. Panel B provides a higher magnification of the 21 day wound demonstrating the appearance of organized collagen fibrils and numerous small capillaries. Panel C depicts a healing wound 42 days after HoxD3 DNA transfer. Panel D provides a higher magnification of the 42 day wound demonstrating the appearance of collagen fibrils and small blood vessels.

FIG. 1 provides photographs of trichrome-stained tissue sections showing collagen deposition in db/db wounds 14 days after creation of 1 cm open wounds. Panel A provides a low power image of a db/db wound treated with control DNA. As indicated in this Panel, there is limited collagen deposition (shown in blue). Panel B provides a higher power image of Panel A. Panel C provides a low power image of a HoxD3 treated wound. As indicated in this Panel, there is more extensive collagen deposition in this treated wound, as compared to the control. Panel D provides a higher power image of Panel C, showing extensive collagen deposition and the presence of small microvessels in the treated wound. Similarly, FIG. 5 provides photographs of trichrome-stained tissue sections from db/db wounds treated with HoxD3 DNA 21 and 42 days post-wounding. These later images depict the appearance of collagen fibrils and small blood vessels in healing wounds treated with HoxD3 DNA.

Furthermore, Northern blot analysis of total RNA taken from wild-type or diabetic wounds at 7 days, indicated that the decrease in type I collagen was related to a decrease in expression of Col1A1 mRNA levels. In addition, the burst strengths of the diabetic wounds were less than 30% of the wild-type wounds when tested with a tensiometer (Instron, Canton, Mass.).

EXAMPLE 4

Cell Culture and Transfection

An immortalized human dermal microvascular endothelial cell line HMEC-1 (Ades et al., J. Invest. Dermatol., 99:683–690 [1992]), kindly provided by T. Lawley of Emory University, Atlanta Ga., was used in these experiments. These cells have previously been shown to maintain many properties of primary dermal microvascular cells in culture including the ability to undergo capillary morphogenesis when cultured on basement membrane (Matrigel) and to maintain expression of a number of endothelial cell surface markers (Xu et al., J. Invest. Dermatol., 102:833–837 [1994]). Cells were maintained in media MCBD 131 supplemented with 10% FCS, gentamicin and 1% hydrocortisone (Sigma), and passaged using calcium and magnesium-free PBS supplemented with 0.053 mM EDTA. Cells were transfected with 2 μg DNA using Effectene reagent (Qiagen) and stable transfectants were selected using 50 μg/ml G418. Expression vectors for HoxD3 and HoxB3 were prepared using methods known in the art (See, Myers et al., supra; Boudreau et al. [1997], supra).

Primary cultures of human dermal microvascular endothelial cells were purchased from Clonetics. Recombinant human VEGF and bFGF were purchased from R&D Systems, and Matrigel was obtained from Collaborative Research. Endothelial cell culture on Matrigel basement membranes was performed as previously described (Boudreau et al., J. Cell. Biol., 139:257–264 [1997]). To release cells from Matrigel for protein or mRNA isolation, cultures were suspended in PBS without $Ca^{2+}$ or $Mg^{2+}$, containing 0.5 mM EDTA and incubated on ice for 1 hour to allow the Matrigel to disperse.

EXAMPLE 5

RNA Isolation and Northern Blot Analysis

Mouse wound tissue obtained as described above was excised and snap frozen in liquid nitrogen and subsequently homogenized prior to RNA isolation using TRIZOL Reagent (Life Technologies). For cultured cells, RNA was isolated with RNA Easy spin columns (Qiagen). For Northern blot analysis, a total of 5–10 μg (tissue) or 10–20 μg (cells) of total RNA was electrophoresed through 1% agarose formaldehyde gels using standard methods. Ribosomal RNA was visualized by staining with 1% ethidium bromide. $^{32}$PdCTP-labeled probes were prepared using the Decaprime kit (Ambion) and purified using Sephadex G-25 columns (Boehringer Mannheim). The blots in FIG. 4 were probed with $1\times10^6$ cpm of labeled cDNA probe directed against human Col1A1 (ATCC), and washed 3 times using low stringency conditions of 2% SSC/0.1% SDS for 30 minutes at 45° C. for mouse tissue, while blots containing human cell derived RNA were subject to an additional high stringency wash in 0.2% SSC at 65° C. for 30 minutes. Similarly, the blots in FIG. 8 were probed with Hybridsol I (Oncor) hybridization buffer containing probes for human uPA, uPAR, MMP-2, β3 integrin or MMP-14. The uPA, uPAR, and MMP-2 cDNAs were purchased from ATCC, while the cDNA of the β3 integrin was obtained from D. Cheresh (Scripps). The cDNA probe for human MMP-14 corresponds to GenBank Accession No. NM004995. Membranes were exposed to Kodak BioMax film or Kodak M5 X-Omat film at −70° C. mRNA levels were quantitated by scanning densitometry of the film and normalized to ethidium bromide staining of total ribosomal RNA using Chemlmager 4000 software (Alpha Innotech).

Figure 4:
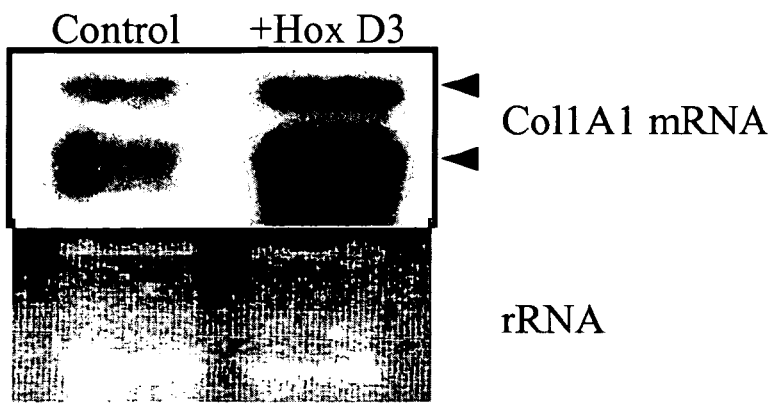
FIG. 4 provides Northern blot analyses of type I collagen RNA expression in control and HoxD3 DNA-treated 0.8 cm wounds. Panel A shows expression of type I collagen (Col1A1) mRNA and corresponding total RNA loading (rRNA) in bilateral wounds from a diabetic (db/db) mouse treated with control or HoxD3 DNA for 7 days. Panel B shows that expression of type I collagen mRNA remains higher in tissues taken from HoxD3 DNA-treated wounds, as compared to bilateral control-treated wounds from the same animals as described for Panel A, after 10 days. The corresponding ribosomal RNA (rRNA) loading controls are shown below. Panel C shows that expression of type I collagen mRNA remains higher in HoxD3 DNA-treated wounds as compared to corresponding control DNA-treated wounds from the same animals as described for Panels A and B, after 17 days.
Figure 4:
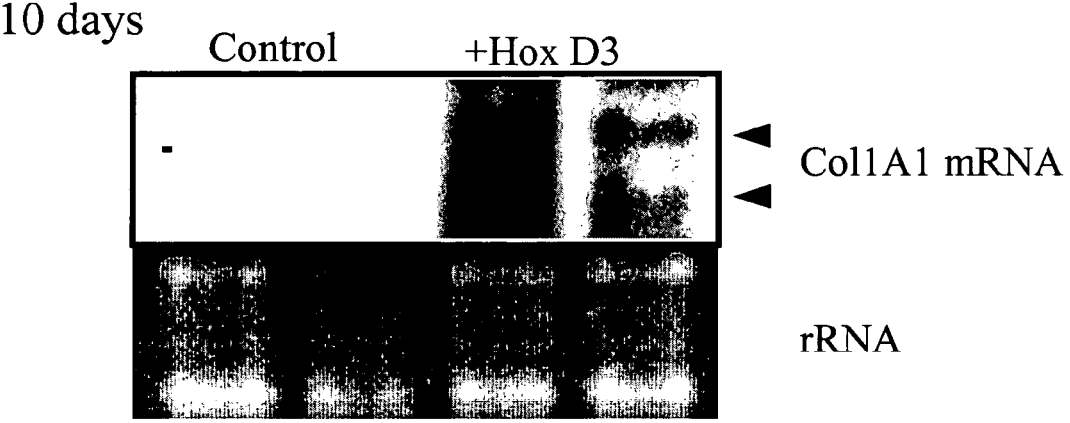
Figure 4:
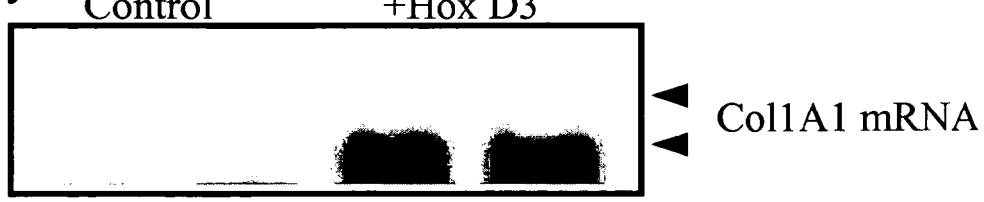

Northern blot analysis for the Col1A1 mRNA showed that endothelial cells transfected with HoxD3, but not HoxB3 or control plasmid, had levels of Col1A1 mRNA which were 2.5 to 3-fold higher than HoxB3-transfected or control-transfected cells respectively (See FIG. 4).

EXAMPLE 6

Construction of HoxD3 Expression Plasmid

In these experiments, construction of the HoxD3 expression plasmid is described. A full-length human HoxD3 clone was isolated using standard PCR, with primers directed against the published sequence (GenBank Accession Number D11117). The DNA sequence of the human HoxD3 clone is provided as SEQ ID NO:1, while the predicted protein sequence of the human HoxD3 clone is provided as SEQ ID NO:2. The forward primer used had the sequence 5'-AGG GTC AGC AGG CCC TGG AGC-3' (SEQ ID NO:3), and the reverse primer had the sequence 5'-AGA GCG GGG AAG GGG GTT CCC GAA CT (SEQ ID NO:4). The 3.4 kb PCR product was inserted into the Topo II cloning vector (Invitrogen). The 3.4 kb insert was then removed with KpnI/BamHI and inserted into the pcDNA3 expression vector under control of the CMV promoter (Invitrogen). Plasmid DNA was then purified using a Qiagen Maxi-prep kit (Qiagen), per the manufacturer's instructions.

EXAMPLE 7

Gene Transfer of Hox D3

In these experiments, gene transfer of HoxD3 to diabetic mice was investigated. As the experiments described above indicate that expression of HoxD3 is decreased in wounds of diabetic (db/db) animals, experiments were conducted using diabetic (db/db) mice with full-thickness wounds administered as described in Example 1. Methylcellulose pellets containing 25 μg HoxD3 plasmid were applied to the wounds. Control (diabetic) animals received methylcellulose pellets containing CMV βgal as a control plasmid.

The wounds were measured weekly until closure. The tissues were then processed for Northern blotting and histology using the methods described in the previous Examples. The results indicated that diabetic control wounds closed in 66 days (on average), while the HoxD3 treated wounds closed in 52 days (on average). The percent of wound closure was significant at day 21 (p=0.02), day 14, and day 28 (p=0.06). In these experiments, five animals were treated with HoxD3 plasmid, while three animals were treated with control DNA.

Figure 2:
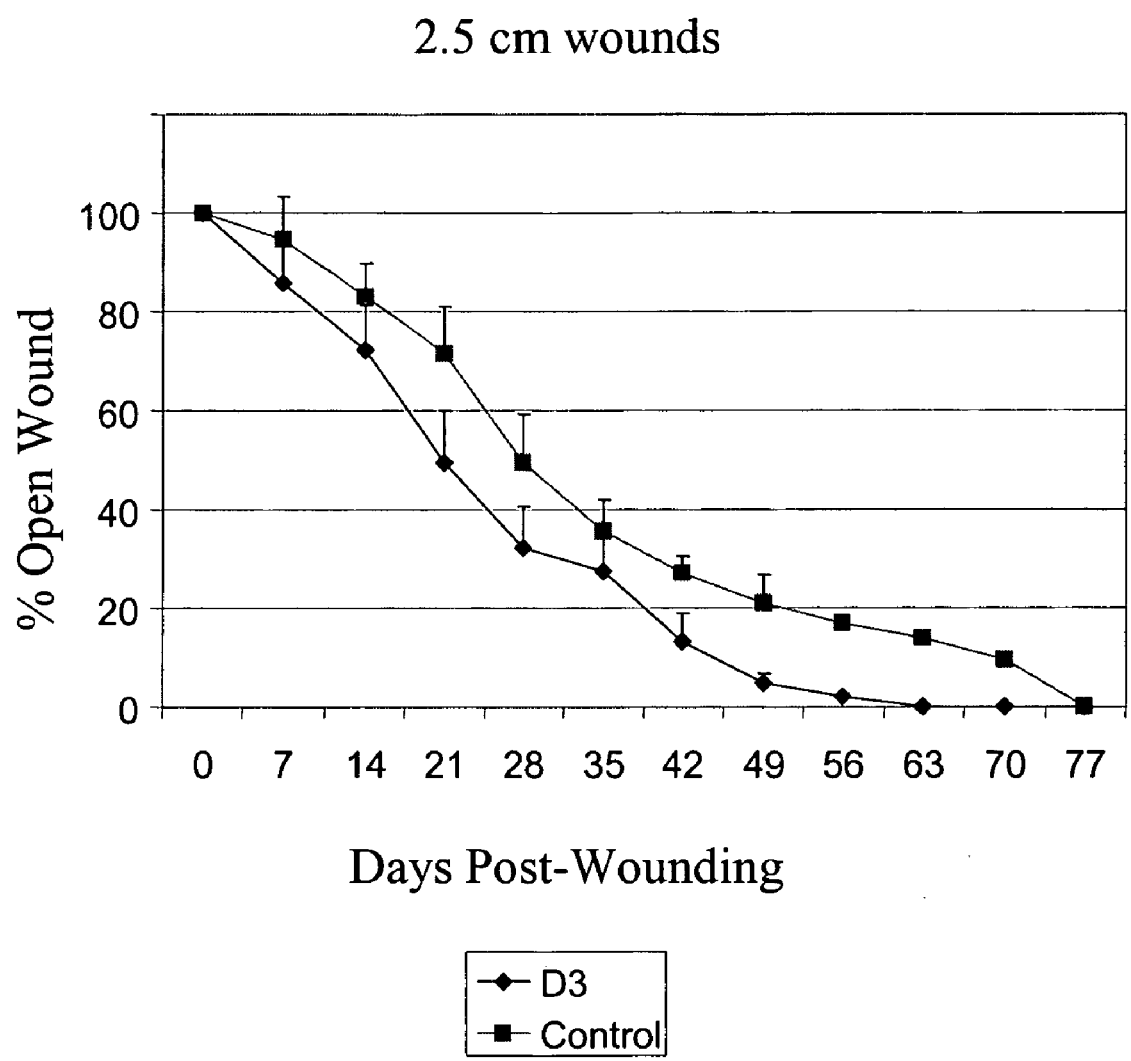
FIG. 2 provides a graph showing closure of 2.5 cm wounds in diabetic (db/db) mice treated with either control DNA or HoxD3 DNA. The observed differences in wound closure are statistically significant at all time points between 7 and 49 days post-wounding.

FIG. 2 provides a graph showing closure of 2.5 cm wounds in diabetic (db/db) mice treated with HoxD3 DNA or control DNA. As indicated in this Figure, mice treated with HoxD3 DNA (indicated by diamonds in this graph) showed a significantly (p=0.02) greater degree of closure at day 21, as compared to mice treated with control DNA (indicated by squares in this graph) treated wounds. The relative difference in closure in HoxD3-treated wounds as compared to control DNA was significant (p=0.05) at 7, 14, 21, 28, 35, 42, and 49 days, as determined using a student's t test.

Figure 3:
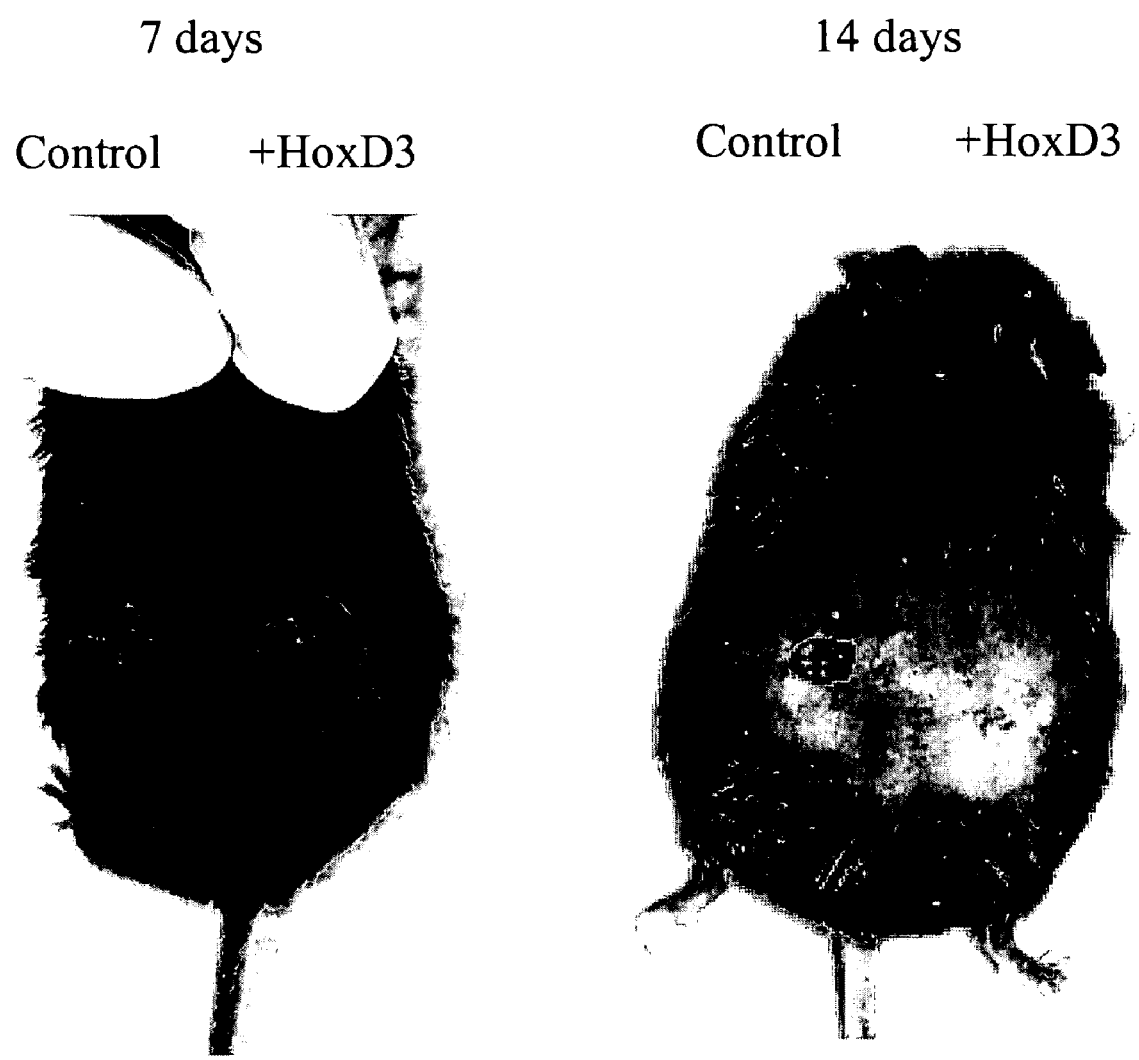
FIG. 3 provides photographs of two animals at 7 and 14 days after wounding (0.8 cm wounds). As indicated by these photographs, the wound closure was significantly improved with the HoxD3 DNA treatment, as compared to the control DNA treatment.

The effects of HoxD3 on 0.8 cm wounds created bilaterally on diabetic (db/db) mice were also investigated. Wound biopsies were taken on days 7, 10, 14 and 17. In preliminary studies, it was found that by 17 days, 5 out of 6 HoxD3 treated wounds and only 1 out of 6 control DNA treated wounds had closed. Based on Northern blot analysis, addition of HoxD3 plasmid to diabetic wounds was found to significantly increase collagen mRNA levels at 3, 7, and 10 days post-wounding. FIG. 3 provides photographs of two mice at day 7 and day 14 after wounding. As indicated, the HoxD3-treated wounds showed a significant difference in closure, as compared to the controls.

FIG. 4 provides Northern blot analyses of type I collagen RNA expression in control and HoxD3 treated 0.8 cm wounds. Panel A shows expression of type I collagen (Col1A1) mRNA and corresponding total RNA loading (rRNA) in bilateral wounds from a diabetic (db/db) mouse treated with control DNA or HoxD3 DNA for 7 days. Panel B shows that expression of type I collagen mRNA remains higher in tissues taken from HoxD3 treated wounds, as compared to bilateral control DNA-treated wounds from the same animals, as described for Panel A, after 10 days. The corresponding ribosomal RNA (rRNA) loading controls are shown below. Panel C shows that expression of type I collagen mRNA remains higher in HoxD3 treated wounds as compared to corresponding control DNA-treated wounds from the same animals as described for Panels A and B, after 17 days.

EXAMPLE 8

Wound Closure and HoxD10

In this Example, experiments conducted to determine the effects of HoxD10 on wound closure are described. Wounds (0.8 cm) were made in wild type C57B1 mice as described above. The wounds were treated with methylcellulose pellets containing 25 μg of CMV βgal cDNA (control) or pellets containing 25 μg of HoxD10 cDNA expression vectors. Open wound size was measured at the time of wounding and at 3, 5, 10 and 11 days following wounding. Closure of HoxD10 treated wounds was significantly impaired (p<0.05) on days 3 and 10, as compared to control treated wounds (n=3). Thus, HoxD10 was shown to delay wound healing.

The use of HoxD10 inhibitors to enhance wound healing is contemplated. In particular, methylcellulose pellets containing HoxD10 RNAi or control pellets containing CMV βgal RNAi are prepared. Eight-millimeter wounds are made on the backs of C57B1 mice and the RNAi-containing methylcellulose pellets are applied to the wounds. Wound size is measured at 0, 3, 5, 10, and 15 days after wounding.

EXAMPLE 9

Use of Naked DNA and Sponges to Transfer DNA

In this Example, experiments conducted using DNA without methylcellulose or another carrier are described. Linear wounds were made on wild-type C57B1 mice, as described above. In initial experiments, 50 μg of CMV βgal plasmid DNA was directly applied by pipet to freshly made linear wounds. After 24 and 48 hours, 1 cm of tissue located peripheral to the injection area was harvested. The tissue was placed in 20% sucrose/PBS for 1 hour, embedded in OCT, and frozen in dry ice and ethanol. Then, 5 μm cryosections were prepared and stained for β-galactosidase activity as known in the art (See e.g., Hengge et al., Nat. Genet., 10:161–166 [1995]). Using this method, no positive staining for β-galactosidase activity was noted.

In subsequent studies, linear wounds were made as described above. Three days later, mice were injected with 50 μg of CMV βgal plasmid DNA, using a 30 gauge needle. DNA was administered either within 1 mm from the edge of the existing wound or alternatively, the wound was reopened in the dermis and the DNA was injected into the wound.

Mice were sacrificed 24 hours following injection. Then, 1 cm of tissue peripheral to the injection area was taken, fixed, and stained as described above. No significant staining was seen using either method of injection.

Finally, polyvinyl sponges (i.e., commonly used as surgical sponges) were soaked in a 100 μl solution containing 50 μg of plasmid CMV βgal plasmid DNA as known in the art (See e.g., Thornton et al., Biochem. Biophys, Res. Commun., 246:654–659 [1998]). Linear wounds were made in mice as described above. The prepared sponges were then inserted directly under the dermis and secured with a vicryl suture. Wounds were closed with 4 sutures. Tissue containing the sponges was harvested at 1, 2, 5, and 7 days following wounding/sponge application and processed as described above (See e.g., Hengge et al. supra). Some scattered positive staining cells (likely fibroblasts) were observed in the day 1 and 2 tissues, but this method did not appear to be an effective means to transduce the DNA. Indeed, this Example indicates that the cellulosic material of the preferred embodiments is a much better method than that described in this Example in which naked DNA and polyvinyl sponges were used.

EXAMPLE 10

Plasmid DNA Uptake and Expression in Chicks

In this Example, experiments were conducted to observe DNA uptake and expression in chicks. As described above, CMV βgal plasmid DNA, c-myc tagged Hox plasmid DNA, and HA-tagged Hox plasmid DNA was incorporated into a 0.5% methylcellulose pellet. The plasmid DNA/methylcellulose mixture was placed onto the chorioallantoic membranes (CAM) of 10 day chick embryos adjacent to pellets containing 50 ng of recombinant VEGF. The CAMs were prepared as described in the art (Brooks et al., Science 264:569–571 [1994]). Expression of β-galactosidase was observed in endothelial, fibroblast, and epithelial cells 48 hours after plasmid DNA/methylcellulose pellet deposition. Expression in chick endothelial cells was confirmed by double immunofluorescence against an endogenous endothelial cell specific marker (e.g., Von Willebrand factor), and the c-myc or HA-tagged Hox protein.

EXAMPLE 11

Effects of Recombinant HoxD3 Protein on Cultured Cells

The use of any suitable gene expression system, including prokaryotic, yeast, insect and mammalian cell expression systems, is contemplated for the production of the recombinant HoxD3 (rHoxD3) protein of the invention. In a preferred embodiment, the rHoxD3 protein is produced with a baculovirus expression system, as known in the art (Ausubel et al., (eds.), Current Protocols in Molecular Biology, Chapter 16.9–16.11, John Wiley and Sons Inc., New York [1997]). In one embodiment, the rHoxD3 protein is expressed with an influenza hemagglutin (HA) epitope tag. rHoxD3 protein is then purified via high performance liquid chromatography (HPLC) or immunoaffinity chromatography.

In this Example, endothelial cells and fibroblasts are cultured in the presence of various concentrations (e.g., ng to μg quantities) of the rHoxD3 protein or a control recombinant protein produced in the same expression system. For these experiments, the use of multiple cell lines is contemplated; including immortalized and primary cells of wild type and diabetic (db/db) mice. Briefly, the effects of rHoxD3 protein on collagen synthesis, proliferation and cell viability are examined after incubation of cultured cells in the presence of rHoxD3. Collagen synthesis is measured by Northern blot as described in Example 5.

To determine the effect of rHoxD3 protein on cell proliferation, the rate of DNA synthesis of cultured cells, is quantitated by measuring bromodeoxyuridine (BrdU) incorporation. After incubation of cells for 4 or 12 hours with 10

μM BrdU, cells are fixed with 70% ethanol and stained with an anti-BrdU kit (Boehringer), followed by staining with 0.5 μg/ml DAPI (4,6 diamidino-2-phenylindole; Sigma). The percentage of BrdU-positive nuclei is determined by counting multiple fields.

To determine the effect of rHoxD3 protein on cell viability, the use of any number of techniques is appropriate. For instance, lactate dehydrogenase (LDH) release from cells is measured to assess toxicity of the recombinant protein preparations (Korzeniewski and Callewaert, J. Immunol. Methods, 64:313–320 [1983]). Alternatively, apoptosis rates are examined by annexin V staining or terminal deoxynucleotidyltransferase-mediated dUTP nick-end labeling (TUNEL) assays, as known in the art (Koopman et al., Blood 84:1415–20 [1994]; Gavrieli et al., J. Cell Biol. 119:493–501 [1992]; and Gorczyca et al., Cancer Res. 53:1945–1951 [1993]).

EXAMPLE 12

Effects of Recombinant HoxD3 Protein on Wounds

For the experiments described in this Example, the transfer of recombinant HoxD3 (rHoxD3) protein to wounds of diabetic mice is contemplated. As the experiments described above indicate that expression of HoxD3 is decreased in wounds of diabetic (db/db) animals, experiments are conducted using diabetic (db/db) mice with full-thickness wounds administered as described in Example 1. Methylcellulose pellets containing various quantities (e.g., 1 ng to 10 μg) of rHoxD3 protein are applied directly to the newly made diabetic mouse wounds. Control (diabetic) animals receive methylcellulose pellets containing a control recombinant protein. The wounds are measured weekly until closure. It is contemplated that the diabetic wounds treated with the rHoxD3 protein pellets close in a shorter period of time than the diabetic wounds treated with the control recombinant protein.

In addition, wound biopsies are taken on days 7, 10, 14 and 17, in order to examine angiogenesis histologically and to assess collagen mRNA expression levels by Northern blot. Tissue sections are processed for histochemistry as described in Example 3. The tri-chrome staining method is used to detect collagen deposition. RNA is isolated and Northern blot analyses are completed on mouse wound tissue as described in Example 5. Briefly, expression of type I collagen (e.g., Col1A1 mRNA) is quantitated by normalization to rRNA. It is contemplated that the degree of collagen deposition in diabetic wounds treated with the recombinant HoxD3 protein pellets is greater than that observed in diabetic wounds treated with the control recombinant protein.

EXAMPLE 13

Kinetics of HoxD3 Expression During Wound Healing In Humans

In order to obtain a temporal description of HoxD3 expression during the wound healing process, 4 mm biopsies of intact skin from 6 patients were taken by hole punch. Additionally, skin biopsies were harvested at 1 hour, 1 day, 5 days, and 15 days after wounding. The biopsies corresponding to a given time point, were pooled. RNA from the biopsied material was isolated by homogenizing the biopsies in RNAclean buffer (AGS, Heidelberg), to which 1/100 part by volume of 2-mercaptoethanol had been added. The RNA was then extracted by treatment with acidic phenol saturated with water twice, followed by extraction in the presence of 1-bromo-3-chloropropane. The RNA was then precipitated with isopropanol and ethanol, and washed with 75% ethanol. After this, a DNase I digestion of the RNA was carried out. For this, 20 μg of RNA (to 50 μl with DEPC-treated water) was incubated at 37° C. for 20 min with 5.7 μl of transcription buffer (Roche), 1 μl of RNase inhibitor (Roche; 40 U/μl) and 1 μl of DNase I (Roche; 10 U/μl). A second digestion step at 37° C. for 20 min was initiated by addition of 1 μl of DNase I. The RNA was then treated with phenol, ethanol-precipitated and washed. All above mentioned steps were carried out using DEPC (diethyl pyrocarbonate)-treated solutions or liquids containing no reactive amino groups. cDNA was then prepared from the extracted RNA in the presence of 1×TaqMan RT buffer (Applied Biosystems), 5.5 mM MgCl$_2$ (Perkin Elmer), 500 μM of each dNTP (Perkin Elmer), 2.5 μM of random hexamers (Perkin Elmer), 1.25 U/μl of MultiScribe Reverse Transcriptase (50 U/μl, Perkin Elmer), 0.4 U/μl RNase inhibitor (20 U/μl, Perkin Elmer), 20 μl of RNA (50 ng/μl) and DEPC-treated water (to 100 μl volume). After addition of the RNA and thorough mixing, the solution was divided in half and placed in 0.2 ml wells (50 μl each) in order to carry out the reverse transcription step in a thermocycler (10 min at 25° C.; 30 min at 48° C. and 5 min at 95° C.). The cDNA was subsequently quantified by means of quantitative PCR using SYBR green PCR master mixes (Perkin Elmer). A triplicate determination was made for each cDNA species (in each case with hoxD3 primers and cyclophilin primers). The stock solution for each cDNA quantitation contained 37.5 μl of 2×SYBR master mix, 0.75 μl of AmpErase UNG (1 U/μl) and 18.75 μl of DEPC-treated water (in a total volume of 57 μl). Per triplicate determination, 1.5 μl of each primer were added to 57 μl of stock solution in a previously optimized concentration ratio. The HoxD3 primers used included: hoxD3-Primer 1, 5'-GCT GCT TAC TAT GAA AAC CCA GG-3' (SEQ ID NO:5); and hoxD3-Primer2, 5'-CGT AAG TGT CCG TAG TTT TGC TGT-3' (SEQ ID NO:6). Sixty μl of the stock solution/HoxD3 primer solution was mixed with 15 μl of the cDNA solution (2 ng/μl) and subdivided into 3 reaction wells. Parallel to this, a stock solution with primers was prepared as a reference for the determination of cyclophilin. The cyclophilin primers used included: Cyclophilin-Primer 1, 5'-TCT TAA CCA CCA GAT CAT TCC TTC T-3' (SEQ ID NO:7); and Cyclophilin-Primer 2, 5'-CCA TAG TGC GAG CAA ATG GG-3' (SEQ ID NO:8). Sixty μl of the stock solution/cyclophilin primer solution was mixed with 15 μl of the same cDNA solution and subdivided into 3 reaction wells. Additionally, in order to set up a standard curve for the Cyclophilin-PCR, various cDNA solutions were prepared as a dilution series (4 ng/μl; 2 ng/μl; 1 ng/μl; 0.5 ng/μl and 0.25 ng/μl). Fifteen μl of each of these cDNA solutions were mixed with 60 μl of the stock solution/cyclophilin primer mixture and subdivided into 3 reaction wells for the determination of cyclophilin concentration. A standard curve for human HoxD3 was set up in the same manner. As a control, PCR reactions were run in the absence of cDNA by addition of 15 μl of DEPC water to 60 μl of both the stock solution/HoxD3 primer mixture and the stock solution/Cyclophilin primer mixture. Each solution was then subdivided into 3 reaction wells prior to thermocycling. The amplification of the batches was carried out in the GeneAmp 5700 (2 min at 50° C.; 10 min at 95° C., followed by 3 cycles of 15 sec at 96° C. and 2 min at 60° C.; then 37 cycles of 15 sec at 95° C. and 1 min at 60° C.). The analysis was carried out by the determination of the relative abundance of human HoxD3 with respect to the Cyclophilin reference. For this, a standard curve was first set up by plotting the $C_{T\text{ values}}$ of the dilution series, against the logarithm of the amount of cDNA in the PCR batch (ng of transcribed RNA) and the slopes (s) of the straight lines was subsequently determined. The efficiency (E) of the PCR results was calculated using the following equation:

$$E = 10^{-1/s} - 1 \quad \text{Equation 1:}$$

The relative abundance (X) of human HoxD3 (Y) was then determined in relation to Cyclophilin (cyc) using the following equation:

$$\text{Equation 2:} \quad X = \frac{(1 + E_{Cyc})^{C_T(Cyc)}}{(1 + E_Y)^{C_T(Y)}}$$

The numerical values were standardized by setting the amount of HoxD3 cDNA obtained from intact skin equal to 1. As is shown in Table 1, while a downregulation of HoxD3 expression was observed during the early phases of wound healing (e.g., 24 hours and 5 days after wounding), an upregulation appears to be necessary for the long-term processes of healing (e.g., 15 days after wounding). This demonstrates that the regulation of HoxD3 expression is critical for wound healing and that delivery of HoxD3 to wounds according to methods provided by the present invention will support wound healing especially in regard to long-term healing processes.

TABLE 1

HoxD3 Expression During Wound Healing

| Tissue From Healthy Individuals | Relative Amount of HoxD3 mRNA |
|---|---|
| intact skin | 1.0 |
| 1 hour after wounding | 1.3 |
| 24 hours after wounding | 0.6 |
| 5 days after wounding | 0.7 |
| 15 days after wounding | 2.1 |

EXAMPLE 14

Dysregulated HoxD3 Expression In Diabetic Human Ulcers

In order to demonstrate, that HoxD3 plays a role not only in normal wound healing but in diabetic wound healing as well, biopsies of 6 patients with chronic venous ulcers (*ulcera venosum*) and biopsies of 4 patients with diabetic foot ulcers were taken from intact skin, from the wound ground, and from the wound edge, for analysis of HoxD3 expression levels. For each group (intact skin, wound ground, wound edge) the biopsies of 6 subjects with venous ulcers were pooled. Accordingly, pools were generated for the different biopsy groups from the diabetic ulcer patients. RNA was isolated and cDNA was synthesized as described above in Example 13. Additionally, HoxD3 cDNA was quantified in relation to Cyclophilin cDNA as previously described, and again the amount of HoxD3 measured in intact skin was set equal to 1. As shown in Table 2, a dysregulation of HoxD3 expression was observed in diabetic ulcers as compared to normal healing wounds (See Table 1). In particular, while HoxD3 expression in venous foot ulcer biopsies was only slightly dysregulated as compared to intact skin, a profound lack of HoxD3 mRNA was observed in biopsies taken from the wounds of the diabetic ulcer patients.

These results demonstrate that HoxD3 is beneficial for wound healing in general, and moreover, that HoxD3 is especially suitable for treating diabetic wounds. Strikingly, during development of the present invention, a specific lack of HoxD3 was observed in diabetic wounds but not in wounds from healthy patients or in badly healing wounds from patients with venous ulcers.

TABLE 2

HoxD3 Expression In Ulcers

| Tissue From Ulcer Patients | HoxD3 mRNA in Diabetic Foot Ulcers | HoxD3 mRNA in Venous Ulcers |
|---|---|---|
| intact skin | 1.0 | 1.0 |
| wound edge | 0.2 | 0.8 |
| wound ground | 0.0 | 1.2 |

EXAMPLE 15

Cloning and Quantitation of HoxA3 by RT-PCR

Approximately 1 µg of total RNA was reverse transcribed using MMLV RT for 1 hour at 42° C. in a total volume of 25 µl. Various amounts of this RT reaction (e.g., 0.1, 1.0, 2.0 and 10.0 µl) were then amplified for 20, 30 or 35 cycles of PCR program of 30 sec at 95° C., 30 sec at 58° C. and 90 sec at 72° C. by using the following primers: forward primer 5'-TGC GAT CAA GAT CGT GAA ACA ACG C-3' (SEQ ID NO:17) corresponding to base pair numbers 93080–93056 of the genomic sequence contained in human PAC clone (RP-1167F23) given GenBank Accession No:AC004079, and the reverse primer 5'-AGA CTC TCC TGG CGC GTA GCC CCA A-3'(SEQ ID NO:18) corresponding to nucleotides 90277–90312 of the same genomic sequence. The expected 1.37 kb PCR product was visualized by electrophoresis on 1% agarose gels containing ethidium bromide. From this analysis it was determined that amplification of 1 µl of the total 25 µl RT reaction for 30 cycles gave optimal, reproducible results within the linear range for amplification. To normalize for total RNA, 1 µl of the same RT reaction was diluted 1:800 in water and amplified under the same conditions with commercially available primers sets for human GAPDH or β-actin (Stratagene). The full-length cDNA was cloned by isolating the 1.37 kb HoxA3 PCR product and inserting it into the TOPO II TA cloning vector (Invitrogen). The identity of the insert was confirmed to be HoxA3 by DNA sequencing performed at the UCSF Biomolecular Resource Center.

EXAMPLE 16

Construction of HoxA3 Expression Plasmid

In these experiments, construction of the HoxA3 expression plasmid is described. An EcoR1 fragment from the TOPO II HoxA3 vector described above, which lacks the last eight amino acids and stop codon, was ligated in frame into the pCR3.1 myc/his vector (Invitrogen), to generate a HoxA3 myc/his fusion clone under control of the CMV promoter. A HoxA3 anti-sense vector was prepared using the entire HoxA3 coding sequence ligated into the pCR3.1 vector (Invitrogen) in the anti-sense orientation. Transfections of the HMEC-1 cell line were performed using the Effectene reagent (Qiagen) and pools of stably transfected cells were selected using 35 µg/ml of G418.

EXAMPLE 17

Effects of HoxA3 on Angiogenesis in Chick Chorioallantoic Membranes

To produce replication defective retroviruses encoding HoxA3, the cDNA encoding the entire human HoxA3 sequence was excised with HindIII and PmeI and inserted into the proviral vector CK at the HindIII site and at the XbaI site, which had been blunted with Klenow polymerase. The viral packaging cell line Q4dh, derived from the QT6 quail fibrosarcoma cell line (Stoker and Bissell, J. Virol., 62:1008–1015 [1988]) was maintained in M199 containing 4% FCS, 1% chicken serum and 1× tryptose phosphate broth. Pools of stable transfectants expressing either a human HoxA3 proviral vector or an empty vector (CK) were generated by transfection using $CaPO_4$ and selected in the presence of 200 µg/ml G418 as described (Stoker and Bissell, supra [1988]; and Boudreau et al., J. Cell Biol., 139:257–264 [1997]). To induce angiogenesis, $5 \times 10^6$ transfected Q4dh cells in a volume of 50 µl of M199 medium were grafted onto chick chorioallantoic membranes (CAMs) from 10 day SPAFAS pathogen free chick embryos as previously described (Boudreau et al., supra 1997). After 72 hours CAMs were harvested and vascular density, morphology and immunohistochemical analysis were performed. Angiogenesis was quantitated by counting the number of branch points arising from the tertiary vessels in a 6 mm square area adjacent to the fibrosarcoma tumors. Measurements were made in 12 samples infected with control virus and in 12 samples infected with HoxA3 expressing virus from 3 separate experiments. Statistical significance was assessed using a paired t-test.

CAMs were fixed in situ in 4% paraformaldehyde, embedded in OCT medium, frozen in a dry ice/ethanol bath and stored at −70° C. Seven µm cryosections of the CAMs were used for immunohistochemistry. Following brief acetone fixation, sections were air-dried and subsequently blocked in PBS containing 2% BSA for one hour followed by staining with appropriate antibodies. A 1:200 dilution of a polyclonal rabbit-anti-human antibody against von Willebrand Factor was used followed by Texas Red conjugated goat anti-rabbit secondary antibody (Calbiochem).

Figure 6:
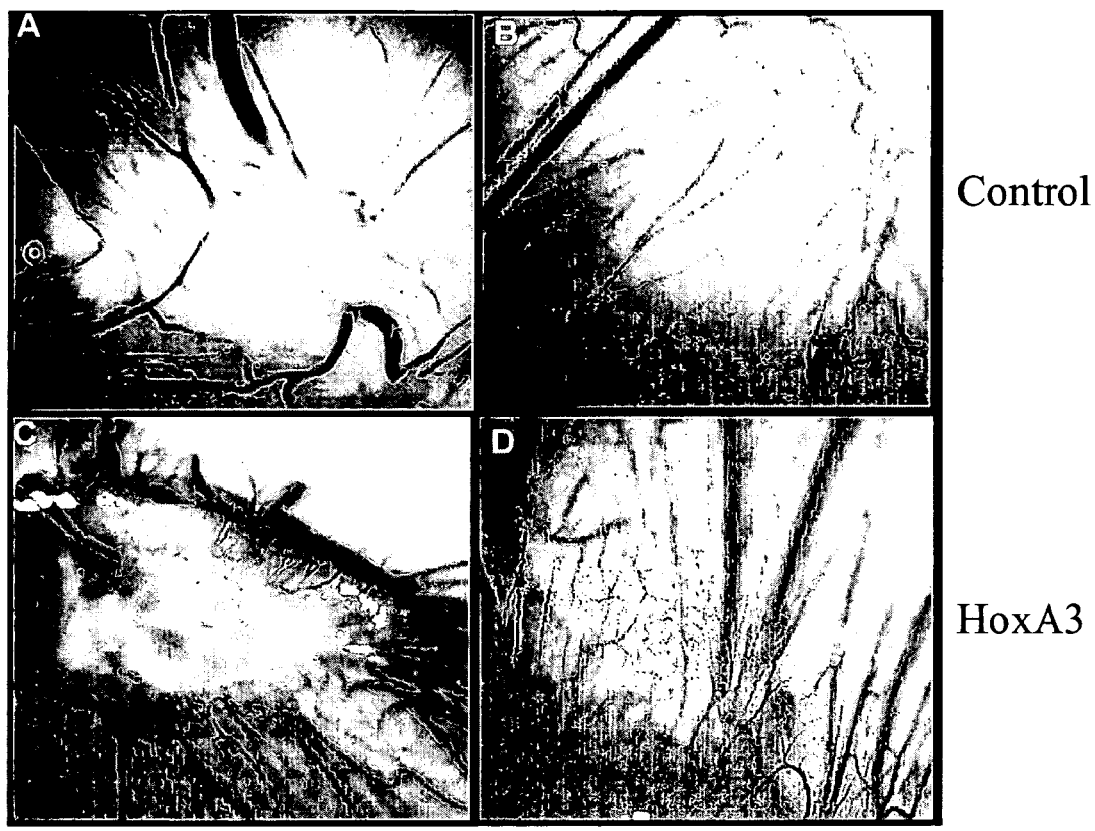
FIG. 6 provides photographs of chick CAM grafted with fibrosarcoma cells transfected with CK (control) or HoxA3. Panel A is a low power image of a chick CAM whole mount taken 72 hours after grafting with CK-transfected fibrosarcoma cells, while Panel B is a higher power photomicrograph which fails to reveal any significant branching or angiogenesis in the tissue adjacent to the tumor. Panel C is a low power photomicrograph of CAM tissue 72 hours after receiving fibrosarcoma cells shedding HoxA3 retrovirus, while Panel D is a higher power photomicrograph showing extensive branching of small microvessels adjacent to the tumor mass.
Figure 7:
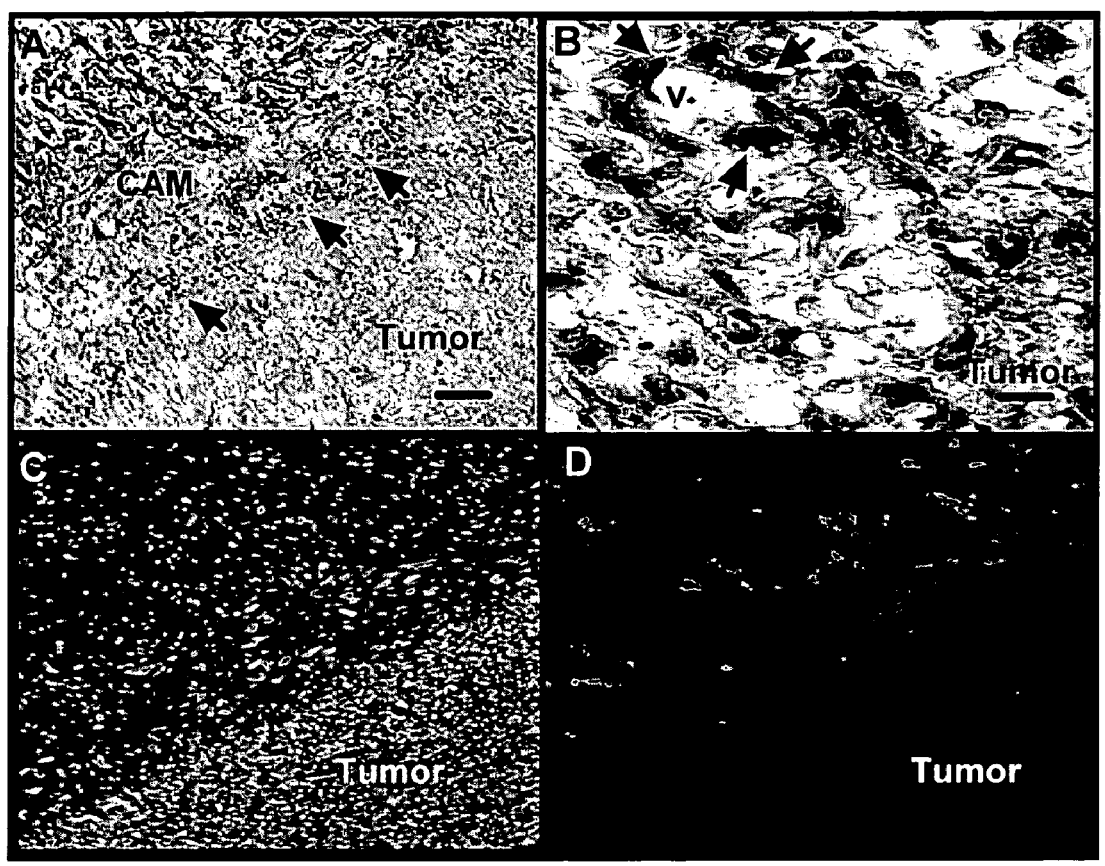
FIG. 7 provides photomicrographs of fibrosarcoma grafts infected with a recombinant retrovirus expressing human HoxA3. Panel A is an in situ hybridization image revealing the expression of retrovirally produced HoxA3 mRNA at the edge of the tumor (arrows) and extending into the adjacent CAM tissue. (Bar=100 µM). Panel B is a higher power photomicrograph showing HoxA3 mRNA in EC (arrows) of a small vessel (v) adjacent to the tumor. (Bar=20 µM). Panel C shows DAPI nuclear staining of a serial section taken from CAM tissue, which had been grafted with tumor cells shedding HoxA3 retrovirus. Panel D shows immunofluorescense staining of the same serial section as shown in panel C, with a polyclonal antibody against the endothelial cell marker, von Willebrand factor.

As shown in FIG. 6, significant increase in angiogenesis in the CAM was observed following infection with the HoxA3 retrovirus (panels C and D), but not with the control retrovirus (panels A and B). Subsequent sectioning of HoxA3-infected CAM tissues followed by in situ hybridization showed high levels of HoxA3 expression in both fibroblasts and endothelial cells adjacent to the virus producing fibrosarcoma cells (See, FIG. 7, panels A and B). Staining of serial sections with a von Willebrand Factor antibody confirmed an increase in vascular density in the HoxA3-infected areas (See, FIG. 7, panel C). Furthermore, of over 46 HoxA3 retrovirus-infected CAM tissues examined, less than 5% (e.g., 3/46) of the tissues showed evidence of hemorrhagic lesions.

EXAMPLE 18

Gelatin Zymography

Culture media was collected from equal numbers of control HMEC-1, HoxA3 or HoxD3 expressing HMEC-1, or from mixed cultures of HoxA3 and HoxD3 transfected HMEC-1 cultured in MCDB 131 media containing 5% FCS. Media was concentrated two-fold using Centricon 30 microconcentrators (Millipore) and 20 µl of concentrated media was mixed with non-denaturing sample loading buffer. Proteins were separated by 10% SDS-PAGE containing 0.1% gelatin (BioRad). Following electrophoresis, gels were washed for 60 minutes in 2.5% Triton X-100 in 50 mM Tris HCl, pH 7.6, and developed for 24 hours at 37° C. in 50 mM Tris HCl, pH 7.6, containing 5 mM $CaCl_2$, 200 mM NaCl and 0.02% Brij-35. The gels were stained with 0.25% Coomassie Blue in 50% methanol and 10% acetic acid. Gels were photographed using an Alpha Innotech Chemlmager 4000 system equipped with a CCD camera and densitometric software.

The majority of MMP-2, secreted by either control, HoxD3 or HoxA3 overexpressing cells migrated at approximately 70 kD corresponding with the latent form of this protease. However, when equal numbers of HoxA3 and HoxD3 overexpressing cells were co-cultured, an additional clear band at approximately 65 kD corresponding to the activated form of MMP-2 was observed (See, FIG. 8, panel D).

EXAMPLE 19

DNA Microarray Analysis

A Human Cell-Cell Interaction Array was purchased from Clontech. Approximately 60 µg of total RNA isolated from control or HoxA3 transfected HMEC-1 cells was labeled using the Atlas Pure Total RNA Labeling System (Clontech). Poly $A^+$ RNA enrichment was done using a streptavidin magnetic bead preparation. cDNA probes were synthesized following reverse transcription and amplification with the supplied primer mix and $\alpha^{32}P$ dATP. Membranes were hybridized according to manufacturers instructions. Following hybridization, membranes were exposed to BiomaxMS film (Kodak) for 1–4 days at −70° C. Quantification of signals was performed by scanning-densitometry and subsequent analysis was done using NIH Image 1.61 software. Microarray analysis was performed on at least two independent samples of RNA harvested from either HoxA3 or control transfected cells.

Densitometric analysis revealed at least a two-fold upregulation of a number of genes in HoxA3-expressing EC in comparison to control-transfected cells. Of note was the increased expression of MMP-14 (MT-1MMP), the cell surface receptor for the serine proteinase uPA (uPAR), as well as tenascin, cdc42GTPase and alpha 3 integrin, each of which have been implicated in promoting angiogenesis or cell migration (Hiroaka et al., Cell, 95:365–377 [1998]; Kroon et al., Am. J. Pathol., 154:1731–1742 [1999]; Ridley, J. Cell Biol., 150:107–109 [2000]; Schenk et al., Mol. Biol. Cell, 10:2933–2943 [1999]; and Gonzales et al., Mol. Biol. Cell, 10:259–270 [1997]).

Figure 8:
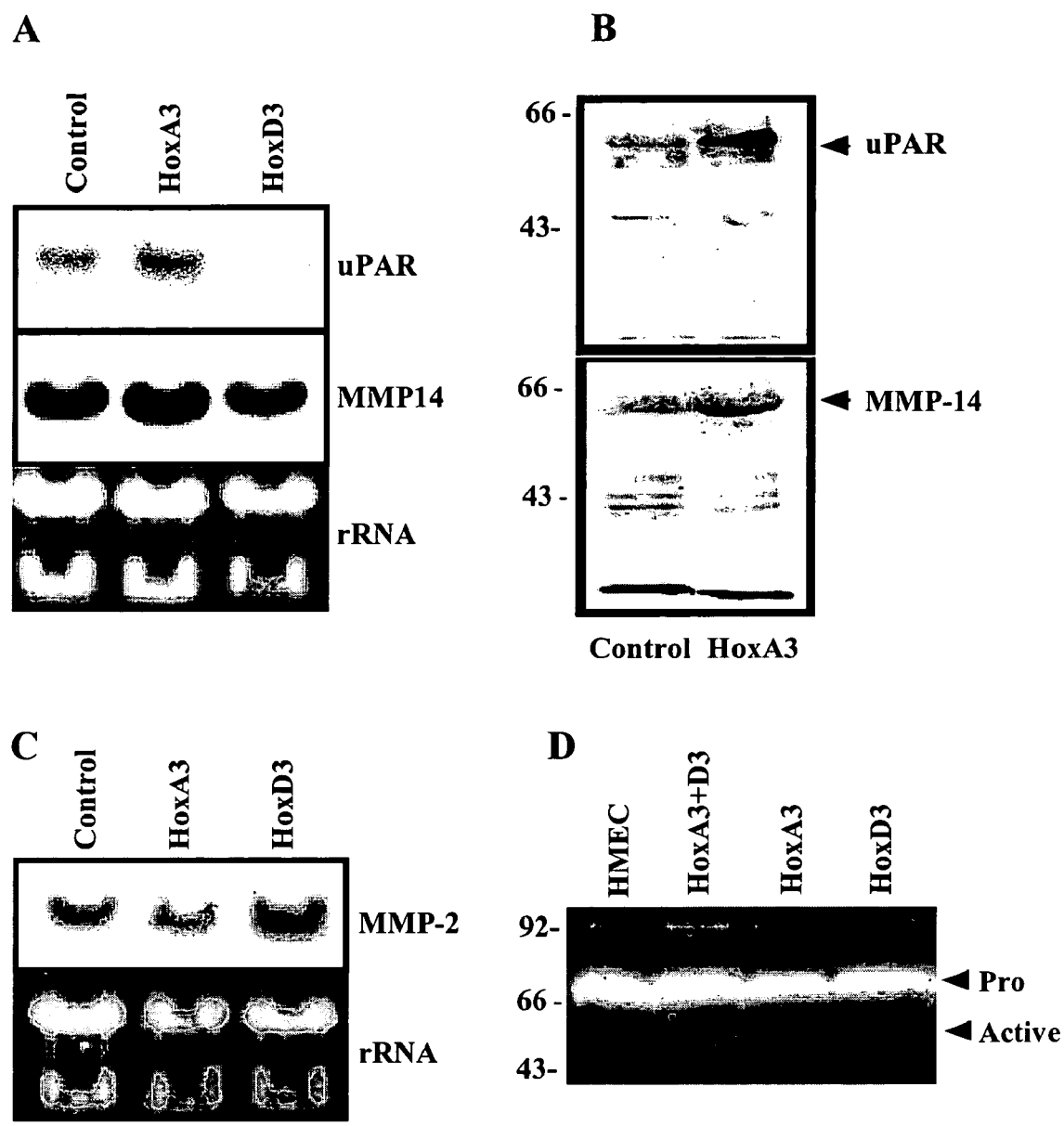
FIG. 8 depicts the influence of HoxA3 on gene expression in endothelial cells. Panel A (top) shows northern blot analysis of urokinase plasminogen activator receptor (uPAR) mRNA levels in HMEC-1 transfected with control plasmid or with HoxA3 or HoxD3 expression vectors. The blot was stripped and reprobed for expression of MMP-14 (middle), while the relative loading of each sample as visualized by ethidium bromide staining of total ribosomal RNA (bottom). Panel B shows a western blot analysis of uPAR (upper) and MMP-14 (lower) protein expression in total cell lysate harvested from control or HoxA3 transfected cells. Panel C (top) shows a northern blot analysis of MMP-2 expression in control, HoxA3, and HoxD3 transfected HMEC-1, and relative RNA loading (bottom). Panel D is a gelatin zymograph of conditioned media collected from control transfected cells (HMEC), co-cultures of HoxA3 and HoxD3 transfected cells (HoxA3+D3), HMEC and HoxA3 transfected cells (HoxA3) or HMEC and HoxD3 (HoxD3) co-cultures. The stronger upper band corresponds to the 68 kD inactive pro-MMP-2 and the lower band shows proteolysis arising from the approximately 62 kD active form of MMP-2.

Northern Blot analyses were subsequently performed as described above in Example 5, to provide independent confirmation that the mRNAs corresponding to uPAR and MMP-14 were upregulated in HMEC-1 transfected with HoxA3, as compared to control transfected EC (See, FIG. 8, panel A). The expression of uPAR and MMP-14 in HoxD3 transfected HMEC-1 was also examined. Interestingly, uPAR and MMP-14 expression was not significantly upregulated in HoxD3-transfected cells, underscoring the distinct phenotypes induced by expression of each of these Hox genes. Western blot analysis of control or HoxA3- transfected HMEC-1 lysates, confirmed that the HoxA3-induced increases in mRNA for both uPAR and MMP-14 were accompanied by increased expression of the respective proteins (See, FIG. 8, panel B). Because MMP-14 acts primarily to activate latent MMP-2, the expression of MMP-2 in HoxA3 and HoxD3-transfected EC was examined. While levels of MMP-2 RNA were unchanged in HoxA transfected cells, overexpression of the paralogous HoxD3 gene, strongly upregulated expression of MMP-2 (See, FIG. 8, panel C). Together these results indicate that HoxA3 and HoxD3 genes act cooperatively in EC to regulate both metallo- and serine proteinase activity during angiogenesis.

EXAMPLE 20

Fibrin and Fibrinogen Migration Assays

In this example, the methods used to assess the effects of HoxA3 and HoxD3 on cell migration in three-dimensional fibrin matrices are described. Specifically, migration of control HMEC-1 or HMEC-I transfected with a HoxA3 antisense construct was examined. Five hundred μl of a solution containing 1 mg/ml Cytodex-3 gelatin coated microcarrier beads (Pharmacia) in PBS were seeded with $5\times10^5$ HMEC-1 cells and maintained in suspension culture in bacterial plates in MCDB 131 media containing 10% FCS until the cells reached confluency. The cells cultured with microcarriers were subsequently embedded into three-dimensional fibrin gels prepared as described (Nehls and Drenckhahn, Microvasc. Res., 50:311–322 [1995]). Briefly, 0.5 ml of beads/HMEC-1 cells, were suspended in a mixture containing 800 μl of a 5.45 mg/ml fibrinogen solution (in PBS, pH 7.2) and 300 μl of a 2 U/ml thrombin solution (both obtained from Sigma) and incubated at 37° C. for 30 minutes to allow fibrin clotting. At the indicated times, 50 ng of recombinant human bFGF (R&D Systems) or 25 μg/ml of control IgG or function blocking antibodies were also included in the gel mixture. The function blocking antibodies tested included antibodies against human uPAR (#399R from American Diagnostica), αvβ3 integrin (LM609 from D. Cheresh of Scripps), and GM6001 (Chemicon International). Following gel clotting, 1 ml of MCDB 131 media containing 5% FCS was added. Fresh media (with or without soluble factors) was added to the fibrin matrices at 48 hour intervals. Cell migration was observed by phase contrast microscopy using a Nikon TE300 inverted microscope and photographed using a Hamamatsu Orca digital camera and Open Lab Improvision software. Migration on fibrinogen substrates was measured as previously described (Myers et al., J. Cell Biol., 148:343–352 [2000]).

Whereas unstimulated control transfected HMEC-1 display a limited ability to invade the fibrin gels, addition of bFGF enhanced migration, which in turn was completely blocked by addition of function blocking antibodies against uPAR (See, FIG. 9, panel A). Importantly, even in the presence of bFGF, HMEC-1 transfected with a HoxA3 antisense construct failed to invade the fibrin gels.

In contrast, overexpression of HoxA3 in HMEC-1 induced extensive spontaneous invasion into fibrin gels even in the absence of exogenous bFGF (See, FIG. 9, panel B). The HoxA3-induced migration could subsequently be attenuated by addition of anti-uPAR antibodies. The addition of the metalloproteinase inhibitor GM6001, had no significant effect on either bFGF or HoxA3-stimulated migration in this system. HoxD3-transfected HMEC-1 also spontaneously migrated into the fibrin gels with out addition of bFGF, but to a lesser degree than that observed for HoxA3-transfected HMEC-1 (See, FIG. 9, panel B). HoxD3-induced migration was also attenuated by addition of anti-uPAR antibodies.

The ability of HoxD3 and HoxA3-transfected EC to migrate on a fibrinogen substratum was then compared. Although HoxA3-transfected EC displayed an enhanced ability to migrate as compared to control transfected EC, this migration was significantly less than migration induced by transfection of HoxD3 (See, FIG. 9, panel C). Together these results indicate that HoxA3 and HoxD3 selectively facilitate EC migration in different microenvironments.

EXAMPLE 21

Modulation of HoxA3 Expression by EC Microenvironment

Figure 10:
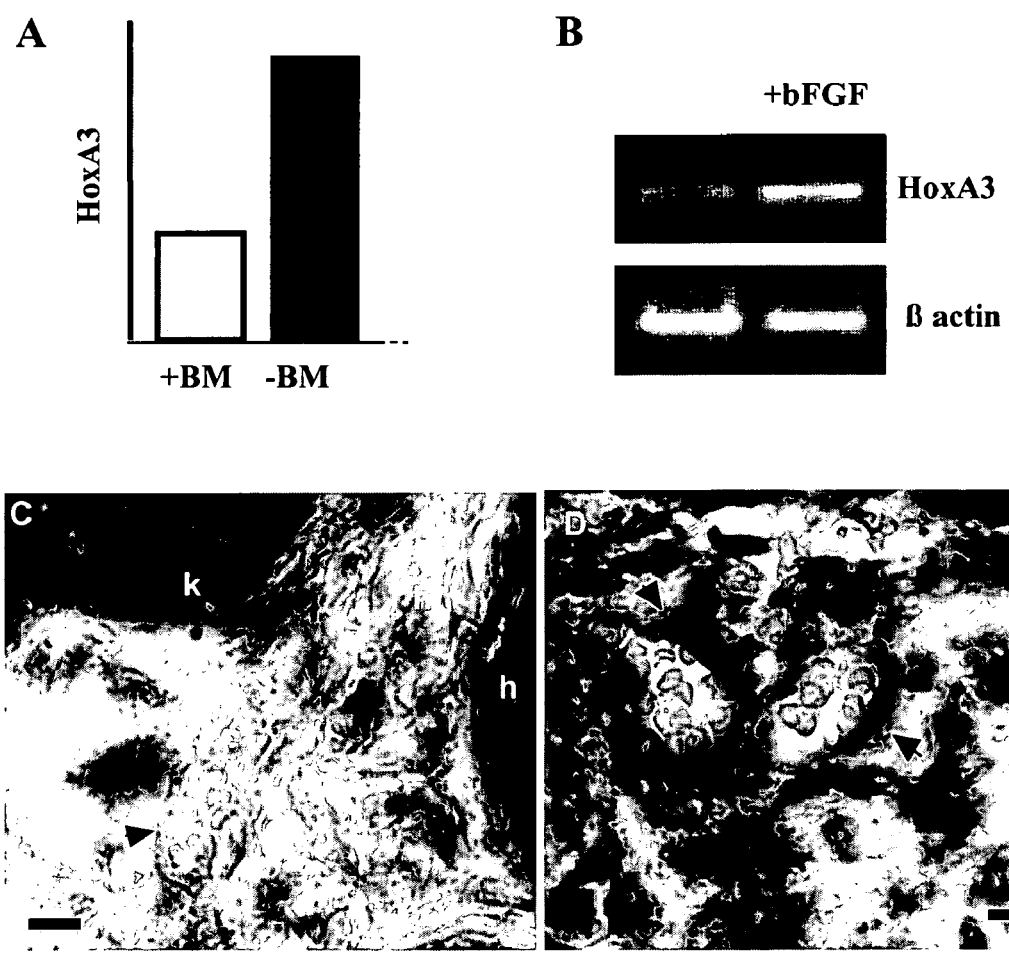
FIG. 10 depicts the relationship between basement membrane contact (panel A), bFGF treatment (panel B), and wounding (panels C and D) on HoxA3 expression (Bar=10 µM).

HMEC-1 was cultured on tissue culture plastic, or on top of thick layers of reconstituted basement membranes (e.g., Matrigel), where cells undergo morphological reorganization into tube-like structures and become growth arrested within 24 hours (Kubota et al., J. Cell Biol., 107:1589–98 [1988]; and Boudreau et al., J. Cell Biol., 139:257–264 [1997]). As shown in FIG. 10, panel A, whereas Hox A3 was expressed at relatively low levels by in EC made quiescent by culturing on basement membranes (BM), expression was significantly higher in activated EC cultured on tissue culture plastic. Treatment of quiescent EC with 30 ng/ml bFGF for 18 hours also increased expression of HoxA3 (See, FIG. 10, panel B).

EXAMPLE 22

HoxA3 Expression During Wound-Induced Angiogenesis In Vivo

C57BL mice obtained from Jackson Laboratories were anaesthetized with ketamine/xylazine and a 1 cm linear full thickness wound was made through the skin. Tissues were harvested after 4 or 7 days, fixed in formalin and embedded in paraffin. Seven μm sections were prepared and deparaffinized by heating at 80° C. for 30 minutes followed by two washes in xylenes for 5 min as described (Uyeno et al., J. Surg. Res., 100:46–56 [2001]). Sections were rehydrated through an ethanol series, post-fixed for 5 minutes with 4% paraformaldehyde, digested with 1 μg/ml Proteinase K (Sigma) for 10 minutes and hybridized using 800 ng/ml of digoxigenin-labelled riboprobes as described (Boudreau et al., J. Cell Biol., 139:257–264 [1997]). Riboprobes against HoxA3 were generated using a RNA Dig labelling kit (Boehringer) with either T7 or Sp6 RNA polymerase from a 395 bp KpnI/EcoRI fragment of the 3' end of human HoxA3 subcloned into the TOPO II PCR cloning vector (See, Example 15).

Hox A3 expression in angiogenic or quiescent endothelial cells in vivo was assessed by in situ hybridization on control or wounded dermal tissue. While levels of HoxA3 were observed to be low in resting vessels in unwounded skin (See, FIG. 10, panel C), HoxA3 was upregulated in EC 4 days following administration of a full thickness linear wound (See, FIG. 10, panel D). These results indicate that like HoxD3, HoxA3 is upregulated in angiogenic environments and also contributes to angiogenesis during wound repair.

EXAMPLE 23

Effects of HoxA3 DNA Application on Wound Closure In Vivo

Genetically diabetic (db/db) mice were anesthetized with 0.04 cc of a ketamine:xylazine mixture (50 mg/cc:2.5 mg/cc), and the dorsum of the mouse was shaved prior to creation of a 2.5 cm wound by excision of the *panniculus carnosus* layer. Immediately following wounding 4 pellets consisting of a mixture of 1% methylcellulose and 25 µg of either βgal cDNA or HoxA3 cDNA were applied to the wounds. The diameter of the wounds was measured immediately following wounding and then every 7 days until the wounds were completely healed. The NIH Image J analyzer was used to determine the area of the wound tracing, the size of which was compared by student's t test.

Figure 11:
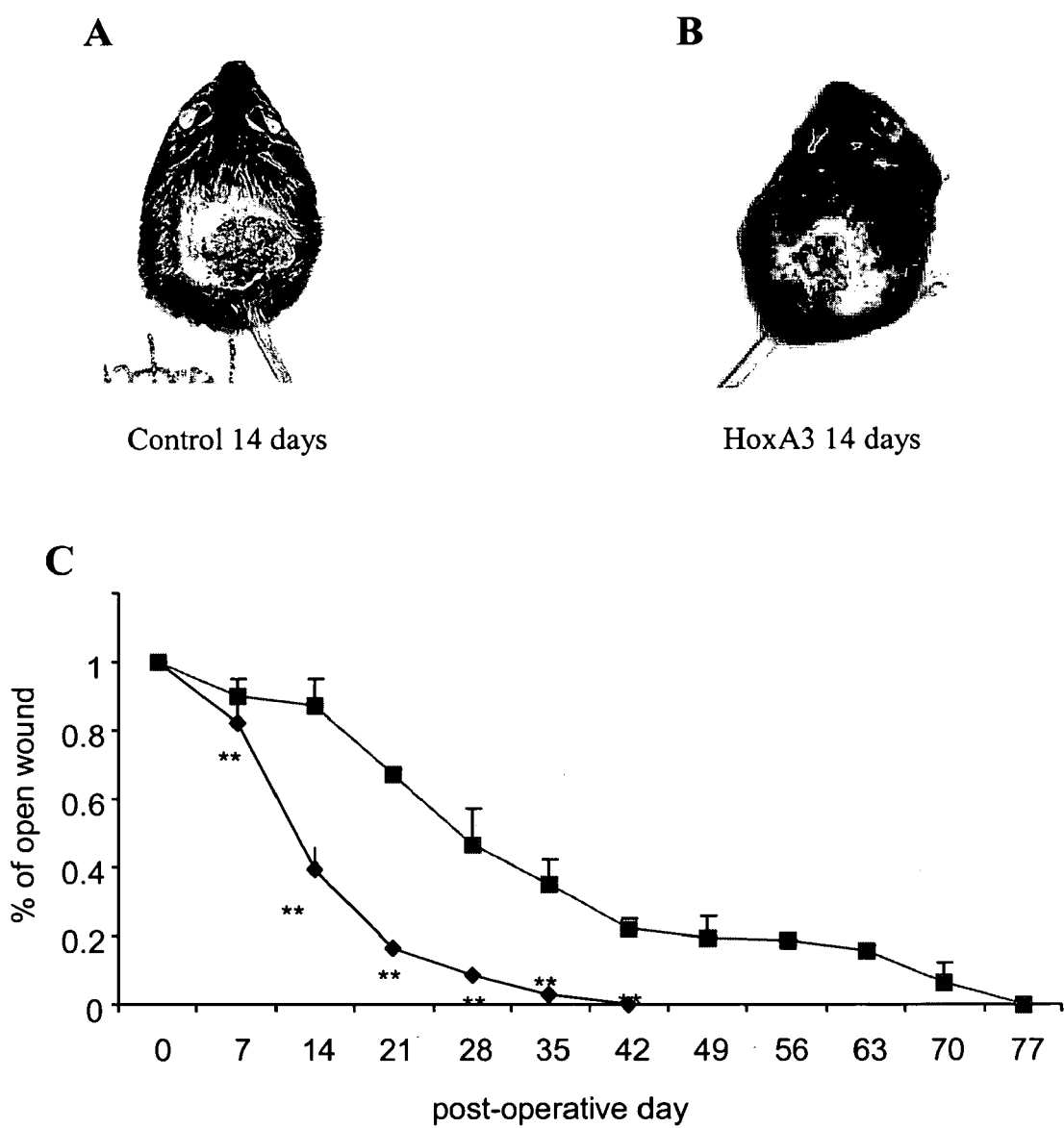
FIG. 11 demonstrates that HoxA3 expression promotes wound repair in diabetic mice. Panels A and B show the appearance of 2.5 cm wounds, 14 days following application of control cDNA or HoxA3 expression plasmids, respectively. Panel C provides a graph demonstrating that HoxA3 treatment enhances wound closure rate in diabetic mice. Squares represent the diameter of control-treated wounds over time, whereas the diamonds represent the diameter of HoxA3-treated wounds over time. Mice treated with HoxA3 showed a significantly greater (**p<0.05) degree of closure at days 7 through 42, as compared to control DNA treated wounds (n=10).
Figure 12:
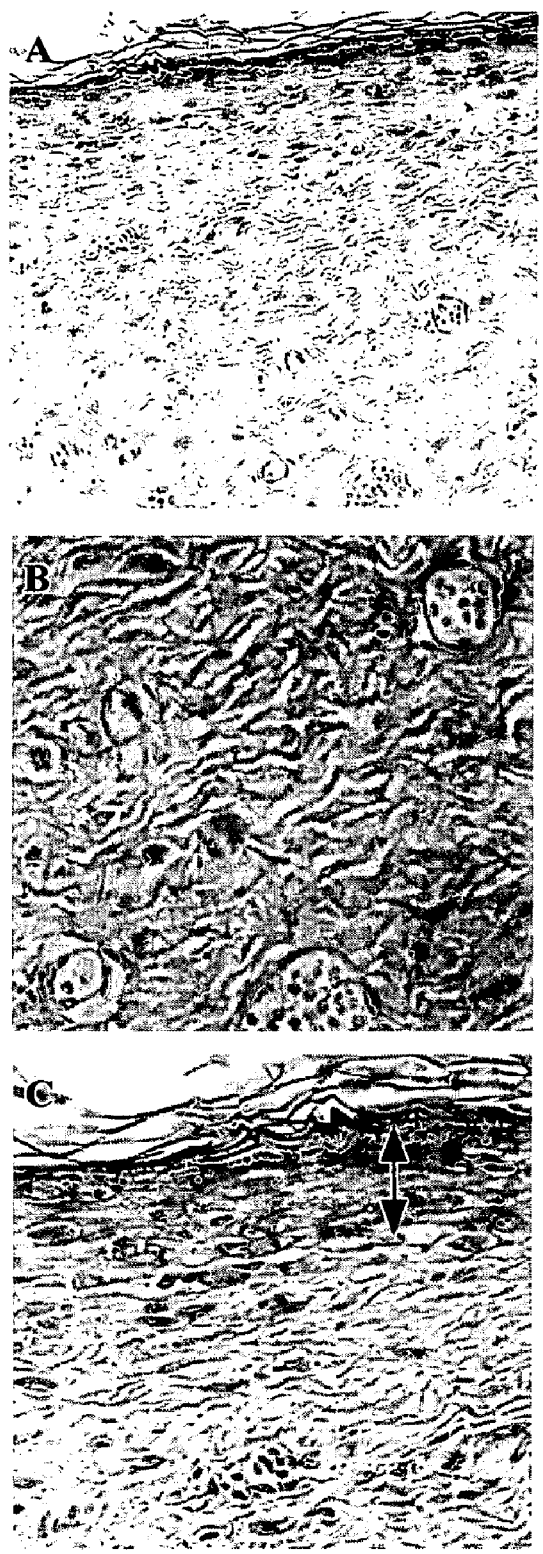
FIG. 12, panels A–C, provide photomicrographs of H and E stained healed tissue sections 21 days after HoxA3 application.

Strikingly, within 14 days, the HoxA3 cDNA treated wounds appeared smaller than those treated with control cDNA (See, FIG. 11, panels A and B). Application of HoxA3 also significantly improved the rate of wound closure, with HoxA3-treated wounds closing at approximately 28–35 days, as compared to wounds treated with control DNA which take 77 days to close (See, FIG. 11, panel C). An increase in the number of blood vessels present in the HoxA3 treated mice, as compared to control treated animals was also observed. Thus although both HoxA3 and HoxD3 can induce angiogenesis and wound closure, HoxA3 was even more effective than HoxD3 in accelerating wound closure.

EXAMPLE 24

Effects of HoxA3 Expression on Wound Closure In Vitro

This example describes methods suitable for assessment of the effects of HoxA3 expression on closure of a scratch wound in a tissue culture assay. The cDNA encoding the human HoxA3/myc-his fusion protein is cloned into the retroviral vector, pLXSN (Clontech). The MK line of immortalized mouse keratinocytes (obtained from D. Morris of UCSF) are then infected with either a HoxA3 retrovirus or a PLXSN/GFP retrovirus. Stable colonies are selected using G418. Cultures of keratinocytes expressing HoxA3 or GFP are then grown to confluence and scratch wounds are administered using a 1 cc syringe. Cells are examined and photographed at 24, 48 and 72 hours following wounding. The number of cells migrating into the wounded area (e.g., scratched), are then counted and compared using a student's t test. In addition, RNA is harvested from the cells, 72 hours following administration of the scratch wounds. RT-PCR and Northern blot analysis are performed using the RNA from the HoxA3 and GFP expressing keratinocytes.

Figure 13:
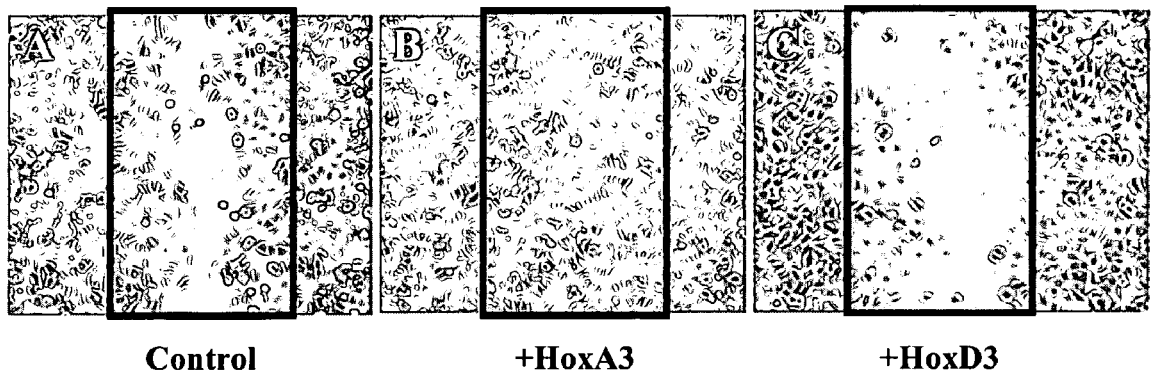
FIG. 13 provides images of control (panel A), HoxA3+ (panel B), and HoxD3+ (panel C) keratinocytes 48 hours after application of scratch wounds. Panel D is a quantitative analysis of relative numbers of cells migrating into the wound area 72 hours after scratch wounding.
Figure 13:
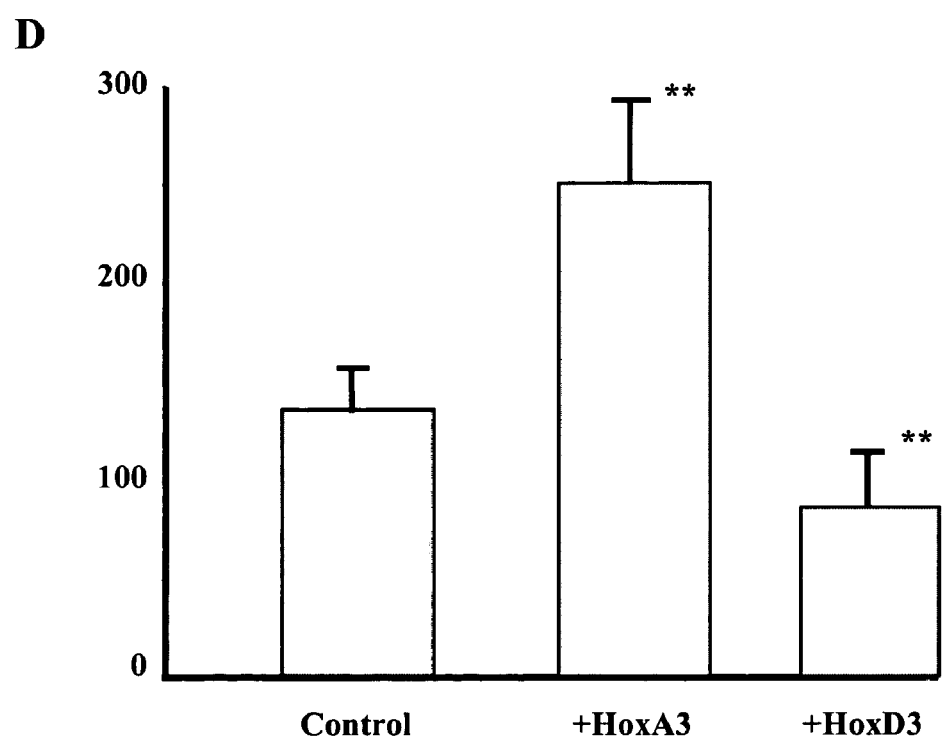

The expression of HoxA3 is contemplated to result in an increased number of keratinocytes migrating into the wound area as compared to control cells. As shown in FIG. 13, panels A–D, a significantly greater number of HoxA3+ cells migrated into the wound area as compared to both the control cells and HoxD3+ cells. Additionally, HoxA3 retrovirus infected keratinocytes are contemplated to express greater amounts of alpha 3 integrin (as was observed in endothelial cells which overexpress HoxA3).

EXAMPLE 25

Cloning and Expression of HoxB3

Approximately 1 µg of total RNA was reverse transcribed using MMLV RT for 1 hour at 42° C. in a total volume of 25 µl. Various amounts of this RT reaction (e.g., 0.1, 1.0, 2.0 and 10.0 µl) were then amplified for 20, 30 or 35 cycles of PCR program of 30 sec at 95° C., 30 sec at 58° C. and 90 sec at 72° C. by using the following primers: forward primer 5'-CGATGCAGAA AGCCACCTAC TACGAC-3' (SEQ ID NO:19) corresponding to base pair numbers 362–387 of human HoxB3; and reverse primer 5'-CGCCGACCCC GGGGGGCTCT TCT-3' (SEQ ID NO:20) corresponding to nucleotides 1,666–1,682 of the published sequence. The expected 1.32 kb PCR product was visualized by electrophoresis on 1% agarose gels containing ethidium bromide. From this analysis it was determined that amplification of 1 µl of the total 25 µl RT reaction for 30 cycles gave optimal, reproducible results within the linear range for amplification. To normalize for total RNA, 1 µl of the same RT reaction was diluted 1:800 in water and amplified under the same conditions with commercially available primers sets for human GAPDH or β-actin (Stratagene). The 1.32 kb HoxB3 PCR product was subsequently ligated into the TOPO II TA cloning vector (Invitrogen), and the identity confirmed by dideoxy sequencing.

The HoxB3 insert containing the entire cDNA encoding human HoxB3 was subcloned into the expression vector PCR3.1 (Invitrogen) in both sense and antisense directions. The orientation was confirmed by restriction digestion. High levels of translation and expression of HoxB3 was achieved by introduction of a Kozak consensus sequence on the 5' end by re-amplifying the cDNA with the primer 5'-GGAAT-TCGGC CACCATGCAG A-3' (SEQ ID NO:21). The resulting cDNA was religated into the PCR3.1 vector. HoxB3 transgene expression was distinguished from endogenous HoxB3 expression via a C-terminal His tag introduced by deletion of the HoxB3 stop codon, and subcloning into the PCR3.1mycHis vector. Sense and antisense HoxB3 clones were transfected into the HMEC-1 cell line by using a calcium phosphate method, and stable transfectants were subsequently selected in the presence of 50 µg/ml of G418.

EXAMPLE 26

Effects of HoxB3 DNA Application on Wound Closure In Vivo

Genetically diabetic (db/db) mice were anesthetized with 0.04 cc of a ketamine:xylazine mixture (50 mg/cc:2.5 mg/cc), and the dorsum of the mouse was shaved prior to creation of a 2.5 cm wound by excision of the panniculus carnosus layer. Immediately following wounding 4 pellets consisting of a mixture of 1% methylcellulose and 25 µg of either βgal cDNA or HoxB3 cDNA were applied to the wounds. The diameter of the wounds was measured immediately following wounding and then every 7 days until the wounds were completely healed. The NIH Image J analyzer was used to determine the area of the wound tracing, the size of which was compared by student's t test.

Strikingly, within one week, the HoxB3 cDNA treated wounds appeared smaller than those treated with control cDNA. Application of HoxB3 also significantly improved the rate of wound closure, with HoxB3-treated wounds closing at approximately 28 days, as compared to wounds treated with control DNA which take 77 days to close (See, FIG. 14).

In summary, the present invention provides numerous advances and advantages over the prior art, including methods and compositions for the improvement of wound healing. All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in diagnostics, cell culture, and/or related fields are intended to be within the scope of the present invention.

We claim:

1. A method comprising:
   a) providing;
      i) a subject with a diabetic skin wound, and
      ii) a composition comprising a gene delivery vehicle and an expression vector comprising HoxB3 nucleic acid encoding a HoxB3 protein, wherein said HoxB3 protein is the protein set forth in SEQ ID NO:23 or a biologically active variant thereof that differs from SEQ ID NO:23 by less than 1%; and
   b) applying said composition to said wound under conditions suitable for transfecting at least one cell of said wound with said expression vector.

2. The method of claim 1, wherein said HoxB3 protein is the protein set forth in SEQ ID NO:23.

3. The method of claim 1, wherein said applying is under conditions such that wound closure is accelerated.

4. The method of claim 1, wherein said applying is under conditions such that angiogenesis in said wound is enhanced.

5. The method of claim 1, wherein said composition further comprises a cellulosic material.

6. The method of claim 1, wherein said wound has a reduced level of expression of HoxD3.

7. The method of claim 1, wherein said expression vector further comprises one or both of HoxD3 nucleic acid encoding a HoxD3 protein and HoxA3 nucleic acid encoding a HoxA3 protein, wherein said HoxD3 protein is the protein set forth in SEQ ID NO:2 or a biologically active variant thereof that differs from SEQ ID NO:2 by less than 1%, and said HoxA3 protein is the protein set forth in SEQ ID NO:15 or a biologically active variant thereof that differs from SEQ ID NO: 15 by less than 1%.

8. The method of claim 1, wherein said HoxB3 nucleic acid comprises a nucleic acid set forth in SEQ ID NO:22.

9. The method of claim 1, wherein said composition is located in a wound care device.

10. The method of claim 1, wherein said wound is an ulcer.

11. The method of claim 7, wherein said HoxD3 protein is the protein set forth in SEQ ID NO:2.

12. The method of claim 7, wherein said HoxD3 nucleic acid comprises the nucleic acid set forth in SEQ ID NO:1.

13. The method of claim 7, wherein said HoxA3 protein is the protein set forth in SEQ ID NO:15.

14. The method of claim 7, wherein said HoxA3 nucleic acid comprises the nucleic acid set forth in SEQ ID NO:14.

15. The method of claim 1, wherein said gene delivery vehicle is selected from the group consisting of gel matrices, liposomes, virosomes, cationic lipids, polylysine, adenoviral vectors, retroviral vectors and gold particles.

16. A method comprising:
   a) providing;
      i) a subject with a diabetic skin wound, and
      ii) a composition comprising a cellulosic material and an expression vector comprising HoxB3 nucleic acid encoding the HoxB3 protein set forth in SEQ ID NO:23; and
   b) applying said composition to said wound under conditions suitable for transfecting at least one cell of said wound with said expression vector.

17. The method of claim 16, wherein said cellulosic material comprises methyl cellulose pellets comprising said expression vector.

18. The method of claim 17, wherein said HoxA3 nucleic acid comprises the nucleic acid set forth in SEQ ID NO:22.

* * * * *